US007270733B2

(12) United States Patent
Wikiel et al.

(10) Patent No.: US 7,270,733 B2
(45) Date of Patent: *Sep. 18, 2007

(54) METHOD AND APPARATUS FOR REAL TIME MONITORING OF INDUSTRIAL ELECTROLYTES

(75) Inventors: Kazimierz J. Wikiel, South Kingstown, RI (US); Aleksander Jaworski, Warwick, RI (US); Hanna Wikiel, South Kingstown, RI (US); Denis P. Hazebrouck, Chepachet, RI (US)

(73) Assignee: Technic, Inc., Cranston, RI (US)

( * ) Notice: Subject to any disclaimer, the term of this patent is extended or adjusted under 35 U.S.C. 154(b) by 345 days.

This patent is subject to a terminal disclaimer.

(21) Appl. No.: 10/621,247

(22) Filed: Jul. 16, 2003

(65) Prior Publication Data

US 2005/0183958 A1    Aug. 25, 2005

Related U.S. Application Data

(60) Provisional application No. 60/397,120, filed on Jul. 19, 2002.

(51) Int. Cl.
*G06N 3/08* (2006.01)
*G01N 27/27* (2006.01)
*C25D 21/12* (2006.01)
(52) U.S. Cl. .................... 205/82; 205/775; 205/787; 205/789; 205/793.5; 705/10
(58) Field of Classification Search ................ None
See application file for complete search history.

(56) References Cited

U.S. PATENT DOCUMENTS

| | | | |
|---|---|---|---|
| 4,631,116 A | 12/1986 | Ludwig | 204/1 T |
| 4,812,210 A | 3/1989 | Bonivert et al. | 204/1 T |
| 4,917,774 A | 4/1990 | Fisher | 204/153.1 |
| 5,192,403 A | 3/1993 | Chang et al. | 204/153.1 |
| 5,196,096 A | 3/1993 | Chang et al. | 204/153.1 |
| 5,223,118 A | 6/1993 | Sonnenberg et al. | 205/81 |
| 5,298,129 A | 3/1994 | Eliash | 204/153.1 |
| 5,298,131 A | 3/1994 | Eliash et al. | 204/153.1 |
| 5,336,380 A | 8/1994 | Phan et al. | 204/153.1 |
| 5,755,954 A | 5/1998 | Ludwig et al. | 205/794 |
| 6,331,244 B1 * | 12/2001 | Lewis et al. | 205/777.5 |
| 6,365,033 B1 * | 4/2002 | Graham et al. | 205/775 |
| 2005/0183958 A1 * | 8/2005 | Wikiel et al. | 205/82 |

OTHER PUBLICATIONS

Schneider, J., "Cross Validation" Feb. 1997, http://www.cs.cmu.edu/~schneide/tut5/node42.html.*
E. Richards et al, "Multivariate Data Analysis in Electroanalytical Chemistry", Electroanalysis, vol. 14, Issue 22, Nov. 2002, pp. 1533-1542.*
Haak, et al. "Cyclic Voltammetric Stripping Analysis of Acid Copper Sulfate Plating Baths, Part One Polyether-Sulfate-Based Additives", Tench Plating and Surface Finishing, 68 (4) 1981, 52.
Haak, et al. "Cyclic Voltammetric Stripping Analysis of Acid Copper Sulfate Plating Baths, Part Two, Sulfoniumalkanesulfonate-Based Additives", Tench Plating and Surface Finishing, 69 (3) 1982, 62.
Graham & Lindberg, "Steady-State Chemical Analysis of Organic Suppressor Additives used in Copper Plating Baths", ECS Meeting Honolulu, 1999, Abstract # 729.
Freitag, et al. "Determination of the Individual Additive Components in Acid Copper Plating Baths", Plating and Surace Finishing, 70, 10, 1983, 55.
Tench & White, "Cyclic Pulse Voltammetric Stripping Analysis Of Acid Copper Plating Baths", J. Electrochem. Soc., 132, 4, 1985, 831.
Krafcik, et al. "An In-Situ Sensor for Monitoring Organic Additives in Copper Plating Solutions", Proceedings of the World Congress on Metal Finishing, Interfinish 92, International Union of Surface Finishing, Brasil, Oct. 1992.
Newton & Kaiser, "Analysis of Copper Plating Baths—New Developments", ECS Meeting Toronto, 1999, Abstract # 357.
Horkans & Dukovic, "Monitoring of SPS-Based Additives in Cu Plating", ECS Meeting Toronto, 1999, Abstract # 360.
Brown & Bear, "Chemometric Techniques in Electrochemistry: A Critical Review", Critical Reviews in Analytical Chemistry, 24(2):99-131, 1993.
Ni, et al. "Simultaneous Polarographic Analysis of Pyrazine and its Methyl Derivatives by Iterative Target Transformation Factor Analysis", Analytica Chimica Acta 316 (1995) 233-238.
Ni, et al. "Simultaneous Adsorptive Voltammetric Analysis of Mixed Colorants by Multivariate Calibration Approach", Analytica Chimica Acta 329, 1996, 65-72.
Ni, et al "Multicomponent Chemometric Determination of Colorant Mixtures by Voltammetry", Analytical Letters, 30(9), 1761-1777, 1997.
Ni, et al. "Voltammetric Determination of Butylated Hydroxyanisole, Butylated Hydroxytoluene, Propyl Gallate and Tert-Butylhydroquinone by use of Chemometric Approaches", Analytica Chimica Acta 412, 2000, 185-193.
Ni, et al. "Voltammetric Determination of Chlorpromazine Hydrochloride and Promethazine Hydrochloride with the Use of Multivariate Calibration", Analytica Chimica Acta 439, 2001, 159-168.

(Continued)

*Primary Examiner*—Harry D Wilkins, III

(57) ABSTRACT

The present invention relates generally to any electrolyte and methods for monitoring the constituents contained therein. More specifically, the present invention relates to plating baths and methods for monitoring the constituents contained therein based on chemometric analysis of voltammetric data obtained for these baths. More particularly, the method of the present invention relates to application of numerous chemometric techniques of modeling power, outlier detection, regression and calibration transfer for analysis of voltammetric data obtained for various plating baths.

54 Claims, 20 Drawing Sheets

OTHER PUBLICATIONS

Lomillo, et al. "Resolution of Ternary Mixtures of Rifampicin, Isoniazid and Pyrazinamide by Differential Pulse Polarography and Partial Least Squares Method", Analytica Chimica Acta 449, 2001, 167-177.

Allus and Brereton, "Determination of Thallium in Cement Dust and Sediment Samples by Differential-Pulse Anodic Stripping Voltammetry: A Chemometric Approach to Linear Calibration", Analyst, Jul. 1992, vol. 117.

Cabanillas, et al. "Resolution of Ternary Mixtures of Nitrofurantoin, Furzolidone and Furaltadone by Application of Partial Least Squares Analysis to the Differential Pulse Polarographic Signals", Talanta, vol. 41, No. 11, pp. 1821-1832, 1994.

Cabanillas, et al. "Abilities of Differentiation and Partial Least Squares Methods in the Analysis by Differential Pulse Polarography Simultaneous Determination of Furazolidone and Furaltadone", Analytica Chimica Acta 302, 1995, 9-19.

Diaz, et al. "Polarographic Behaviour of Sulfadiazine, Sulfamerazine, Sulfamethazine and Their Mixtures. Use of Partial Least Squares in the Resolution of the Non-additive Signals of These Compounds", Analyst, Apr. 1996, vol. 121, 547-552.

Guiberteau, "Indirect Voltammetric Determination of Carbaryl and Carbofuran Using Partial Least Squares Calibration", Analytica Chimica Acta, 305, 1995, 219-226.

Diaz, "Voltammetric Behavior and Simultaneous Determination of the Antioxidants Propyl Gallate, Butylated Hydroxyanisole, and Butylated Hydroxytoluene in Acidic Acetonitrile-Water Medium Using PLS Calibration", Electroanalysis, 1998, 10, No. 7.

Cabanillas, et al. "Resolution by Polarographic Techniques of Atrazine-Simazine and Terbutryn-Prometryn Binary Mixtures by Using PLS Calibration and Artifical Neural Networks", Analyst, 2000, 125, 909-914.

Lastres, et al. "Use of Neural Networks in Solving Interferences Caused by Formation of Intermetallic Compounds in Anodic Stripping Voltammetry", Electroanalysis, 1997, 9, No. 3.

Chan, et al. "Artificial neural network Processing of Stripping Analysis Responses for Identifying and Quantifying Heavy Metals in the Presence of Intermetallic Compound Formation", Anal. Chem, 1997, 69, 2373-2378.

Richards, et al. "Optimisation of a Neural network Model for Calibration of Voltammeric Data", Chemometrics and Intelligent Laboratory Systems, 61, 2002, 35-49.

Wehrens, et al. "Calibration of an Array of Voltammetric Microelectrodes", Analytica Chimica Acta 334, 1996, 93-101.

Matos, et al. "Modified Microelectrodes and Multivariate Calibration for Flow Injection Amperometric Simultaneous Determination of Ascorbic Acid, Dopamine, Epinephrine and Dipyrone", Analyst, 125, 2011-2015, 2000.

Diaz-Cruz, et al. "Application of Multivariate Curve Resolution to Voltammetric Data. Part 1. Study of Zn(II) Complexation with Some Polyelectrolytes", Journal of Electroanalytical Chemistry 393, 7-16, 1995.

Mendieta, et al. "Application of Multivariate Curve Resolution to Voltammetric Data", Analytical Biochemistry, 240, 134-141, 1996.

Diaz-Cruz, et al. "Cadmium-Binding Properties of Glutathione: A Chemometrical Analysis of Voltammetric Data", Electroanal. Chem., 393, 1995, 7.

Diaz-Cruz, et al. "Study of the Zinc-Binding Properties of Glutathione by Differential Pulse Polarography and Multivariate Curve Resolution", Journal of Inorganic Biochemistry, 70, 1998, 91-98.

Diaz-Cruz, et al. "Zinc-binding properties of the C-Terminal Hexapeptide Lys-Cys-Thr-Cys-Cys-Ala from Mouse Metallothionein: Analysis by Differential Pulse Polargraphy and Multivariate Curve Resolution", Analytica Chimica Acta 385, 1999, 353-363.

Diaz-Cruz, et al. "Complexation of Cadmium by the C-terminal hexapeptride Lys-Cys-Thr-Cys-Cys-Ala from Mouse Metallothionein: Study by differential pulse polarography and circular dichroism spectroscopy with multivariate curve resolution analysis", Analytica Chimica Acta 390, 1999, 15-25.

Diaz-Cruz, et al. "Differential Pulse Polarographic Study of the Pb(II) Complexatin by Glutathione", Journal of Electroanalytical Chemistry, 516, 2001, 110-118.

Grabaric, et al. "Application of Multivariate Curve Resolution to the Voltammetric Data Factor Analysis Ambiguities in the Study of Weak Consecutive Complexation of Metal Ion with Ligand", Analytica Chimica Acta, 341, 1997, 105-120.

Torres, et al. "Multivariate Curve Resolution Analysis of Voltammetric Data Obtained at Different Time Windows: Study of the System $Cd^{2+}$-nitrilotriacetic Acid", Analytica Chimica Acta 371, 1998, 23-37.

Esteban, et al. "Camium Binding Properties of the C-Terminal Hexapeptide from Mouse Metallothionein: Study by Linear Sweep Voltammetry and Multivariate Curve Resolution Analysis", Journal of Electroanalytical Chemistry, 468, 1999, 202-212.

Diaz-Cruz, et al. "Multivariate Curve Resolutin of Cyclic Voltammetric Data: Application to the Study of the Cadmium-Binding Properties of Glutathione", Anal. Chem., 1999, 71, 4629-2636.

Fernandez, "Voltammetric Soft Modelling Approach for Systems with Both Electrochemically Labile and Inert Compleses: the Zn-Glycine Case", Electroanalysis, 2001, 13, No. 17.

Diaz-Cruz, et al. "Soft- and Hard-Modeling Approaches for the Determination of Stability Constants of Metal-Peptide Systems by Voltammetry", Analytical Biochemistry 279, 189-201, 2000.

Fernandez, et al. "Soft Modelling Approach Applied to Voltammetric Data: Study of Electrochemically Labile Metal-Glycine Complexes", Journal of Electroanalytical Chemistry, 505, 2001, 44-53.

Cruz, et al. "Mutivariate Curve Resolution of Polarographic Data Appled to the Study of the Copper-Binding Ability of Tannic Acid", Analytica Chimica Acta, 424, 2000, 203-209.

Esteban, et al. "Multivariate Curve Resolution with Alternating Least Squares Optimisation: A Soft-Modelling Approach to Metal Complexation Studies by Voltammetric Techniques", Trends in Analytical Chemistry, vol. 19, No. 1, 2000.

Berzas, et al. "Partial Least Squares Method in the Analysis by Square Wave Voltammetry. Simultaneous Determination of Sulphamethoxypyridazine and Trimethoprim", Analytica Chimica Acta 349, 1997, 303-311.

Saurina, et al. "Cyclic Voltammetric Simultaneous Determination of oxidizable Amino Acids Using Multivariate Calibration Methods", Analytica Chimica Acta, 405, 2000, 153-160.

Herrero, et al. "Multivariate Calibration Transfer Applied to the Routine Polargraphic Determination of Copper, Lead, Cadmium and Zinic", Analytica Chimica Acta, 348, 1997, 51-59.

Herrero, et al. "Modelling the Background Current with Partial Least Squares Regression and transference of the Calibration Models in the Simultaneous Determination of Tl and Pb by Stripping Voltammetry", Talanta, 46, 1998, 129-138.

Herrero, et al. "Solving the Interference Due to Coupled Reactions in the Polargraphic Determination of Benzaldehyde with Soft Modelling", Journal of Electroanalytical Chemistry, 432, 1997, 223-227.

Herrero, et al. "Modelling the Matrix Interference of Iron in the Multivariate Determination of Copper by Stripping Voltammery Instrument Standardization", Talanta, 29, 1999, 801-811.

Herrero, et al. "Qualitative and quantitative Aspects of the Application of Genetic Algorithm-based Variable Selection in Polargraphy and Stripping Voltammetry", Analytica Chimica Acta, 378, 1999, 245-259.

Sanz, et al. "Capability of Discrimination: Application to Soft Calibration Methods", Analytica Chemica Acta, 446, 2001, 297-311.

Engbolm, "Fourier Transform of a Reversible Linear Sweep Voltammogram", Anal. Chem., 1992, 64, 2530-2538.

Engbolm, "Properties and Application of the Fourier Transform of a Voltammetric Wave", J. Electroanal. Chem., 332, 1992, 73-99.

Simons, et al. "Data Processing for Amperometric Signals", Analyst, Apr. 1995, vol. 120.

Chow, et al. "Signal Enhancement of Potentiometric Stripping Analysis Using Digital Signal Processing", Analytica Chimica Acta, 307, 1995, 15-26.

Economou, et al. "Data Enhancement in Adsorptive Stripping Voltammery by the Application of Digial Signal Processing Techniques", Analyst, 119, 1994, 847.

Economou & Fielden, "Digital Filtering in Stripping Analysis", Analytica Chimica Acta, 305, 1995, 165-175.

Do Lago, et al. "Applying Moving Median Digital Filter to Mass Sepctrometry and Potentiometric Titration", Analytica Chimica Acta, 310, 1995, 281-288.

Zou & Mo, "Spline Wavelet Analysis for Volatmmetric Signals", Analytica Chimica Acta, 340, 1997, 115-121.

Zheng & Mo, "The Coupled Application of the B-Spline Wavelet and RLT Filtration in Staircase Voltammetry", Chemometrics and Intelligent laboratory Systems, 45, 1999, 157-161.

Chow, et al. "Signal Filtering of Potentiometric Stripping Analysis Using Fourier Techniques", Analytica Chimica Acta, 338, 1997, 167-178.

Bos & Linden, "Automatic Polarographic Elucidation of Electrode Mechanisms by Means of a Knowledge-Based System", Anal. Chim. Acta., 231, 1990, 59.

Palys, et al. "Automatic Polarograpic Elucidation of Electrode Mechanisms by Means of a Knowledge-Based System", Anal. Chim. Acta., 248, 1991, 429.

Palys, et al. "Automatic Polargraphic Elucidation of Electrode Mechanisms by Means of a Knowledge-Based System", Analytica Chimica Acta., 283, 1993, 811-829.

Palys, et al. "Automatic Polarographic Elucidation of Electrode Mechanisms by Means of a Knowledge-Based System", Analytica Chimica Acta, 284, 1993, 107-118.

Esteban, et al. " Expert System for the Voltammetric Determination of Trace Metals", Analytica Chimica Acta, 268, 1992, 95.

Esteban, et al. "Expert System for the Voltammetric Determination of Trace Metals", Analytica Chimica Acta, 268, 1992, 107.

Esteban, et al. "Expert System for the Voltammetric Determination of Trace Metals", Analytica Chimica Acta, 284, 1993, 435-443.

Esteban, et al. "Expert System for the Voltammetric Determination of Trace Metals", Analytica Chimica Acta, 285, 1994, 193-208.

Esteban, et al. "Expert System for the Voltammetric Determinatin of Trace Metals", Analytica Chimica Acta, 285, 1994, 377.

Garcia-Armada, et al. "Knowledge-Based System for the Provision of an Analytical Strategy for Simultaneous Determination of Metals by Differential-Pulse Polarography", Analytica Chimica Acta, 316, 1995, 47.

Geladi & Knowalski, "Partial Least-Squares Regression: A Tutorial", Analytica Chimica Acta, 185, 1986, 1.

Wold, "Principal Component Analysis", Chemometrics and Intelligent Laboratory Systems, 2, 1987, 37-52.

Donahue & Brown, "Successive Average Orthogonalization of Spectral Data", Anal. Chem., 1991, 63, 980-985.

Shah & Gemperline, "Combination of the Mahalanobis Distance and Residual Variance Pattern Recognition Techniques for Classification of Near-Infrared Spectra", Anal. Chem., 62, 1990, 465.

Rousseeuw & Driessen, "A Fast Algorithm for the Minimum Covariance Determinant Estimator", Technometrics, 41, 1999, 212.

Egan & Morgan, "Outlier Detection in Multivariate Analytical Chemical Data", Anal. Chem., 1998, 70, 2372-2379.

Haaland & Thomas, "Partial Least-Squares Methods for Spectral Analyses. 1. Relation to Other Quantitative Calibration Methods and the Extraction of Qualitative Information", Anal. Chem., 1998, 60, 1193-1208.

Kindsvater, et al. "Correlation of Retention Volumes of Substituted Carboranes with Molecular Properties in High Pressure Liquid Chromatography Using Factor Analysis", Analytical Chemistry, vol. 46, No. 8, Jul. 1974.

Exner, "Additive Physical Properties, I. General Relationships and Problems of Statistical Nature", Collection Czechoslov. Chem. Commun., vol. 31, 1966.

Wang, et al. "Multivariate Instrument Standardization", American Chemical Society, Anal. Chem., 1991, 63, 2750-2756.

Wang, et al. "Additive Background Correction in Multivariate Instrument Standarization", Anal. Chem., 1995, 67, 2379-2385.

Lee et al., "Design Analysis of an Electroless Plating Bath Using CFD Technique", IEEE Transactions on Eletronics Packaging Manufacturing, Oct. 2000, vol. 23, No. 4, pp. 306-313, especially pp. 30, 307 and 309.

Thomas et al., "Issues Associated with the use of Electroless Copper Films for Submicron Multilevel Interconnection", Proceedings of the 7th International IEEE VLSI Multilevel Interconnection Conference, Jun. 1990, pp. 335-337.

Ho et al., "High Current Encapsulated Target System for Radioistope Production", Proceedings of the 1997 Particle Accelerator Conference, May 1997, vol. 3, pp. 3485-3487.

* cited by examiner

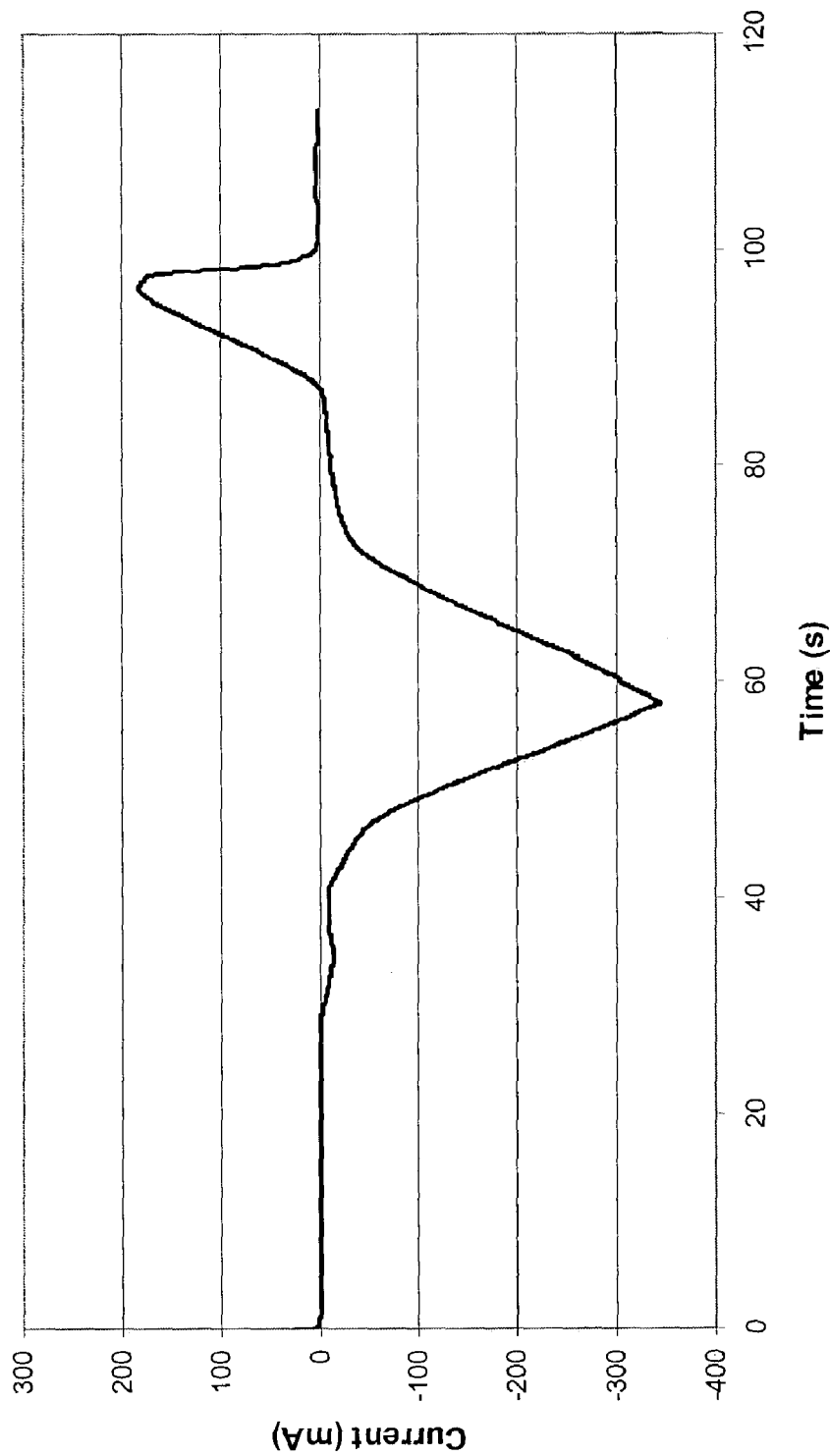
Figure 1. An example cyclic DC voltammogram scan dq21b26, ch2 for CUBATH® ViaForm™ (Enthone) copper plating bath.

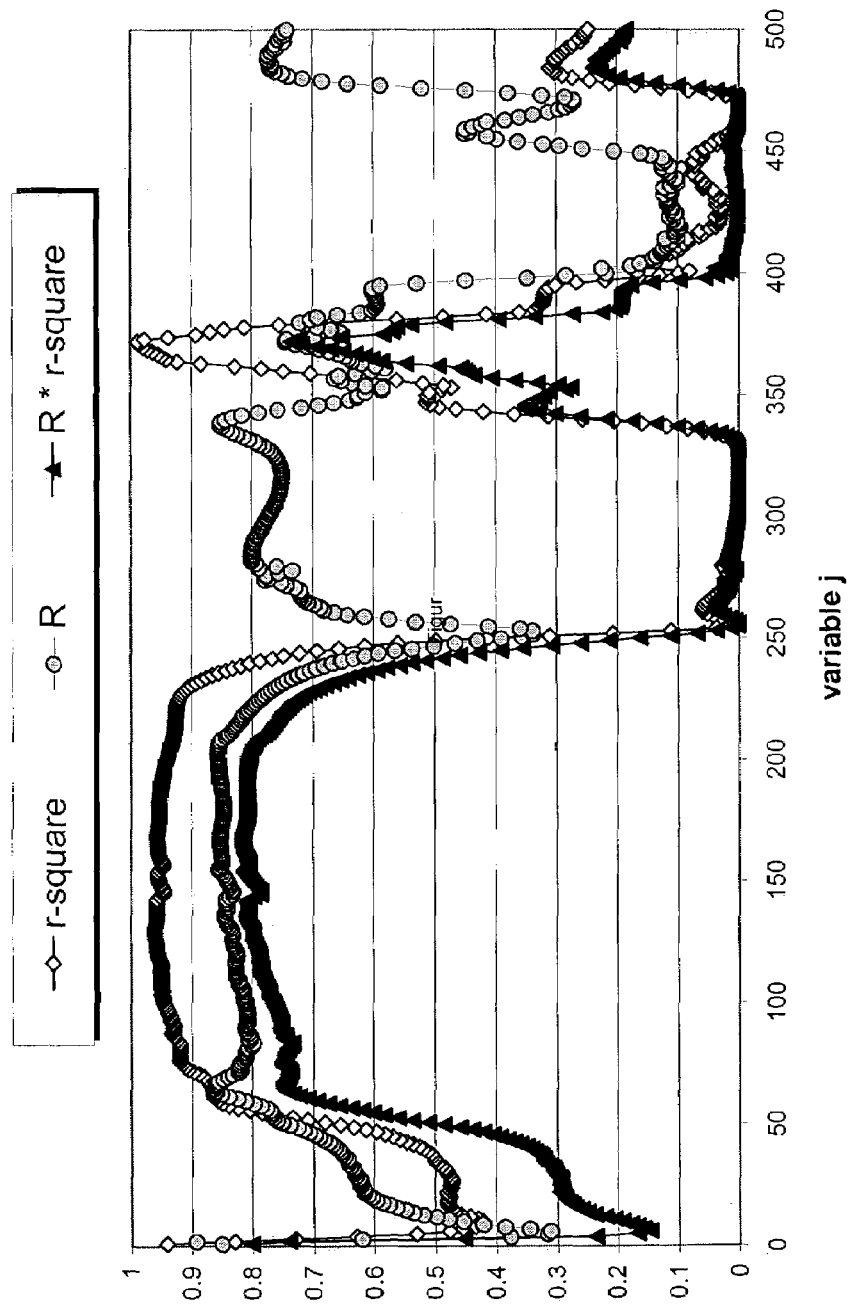
Figure 2. The squared correlation coefficients (Equation 7), $r^2$, for selfpredicted autoscaled tin concentrations obtained via least squares regression for each point of the voltammogram, variable j, (scan dq21x10, channel 2). The modeling power (Equation 11), R, calculated for same data.

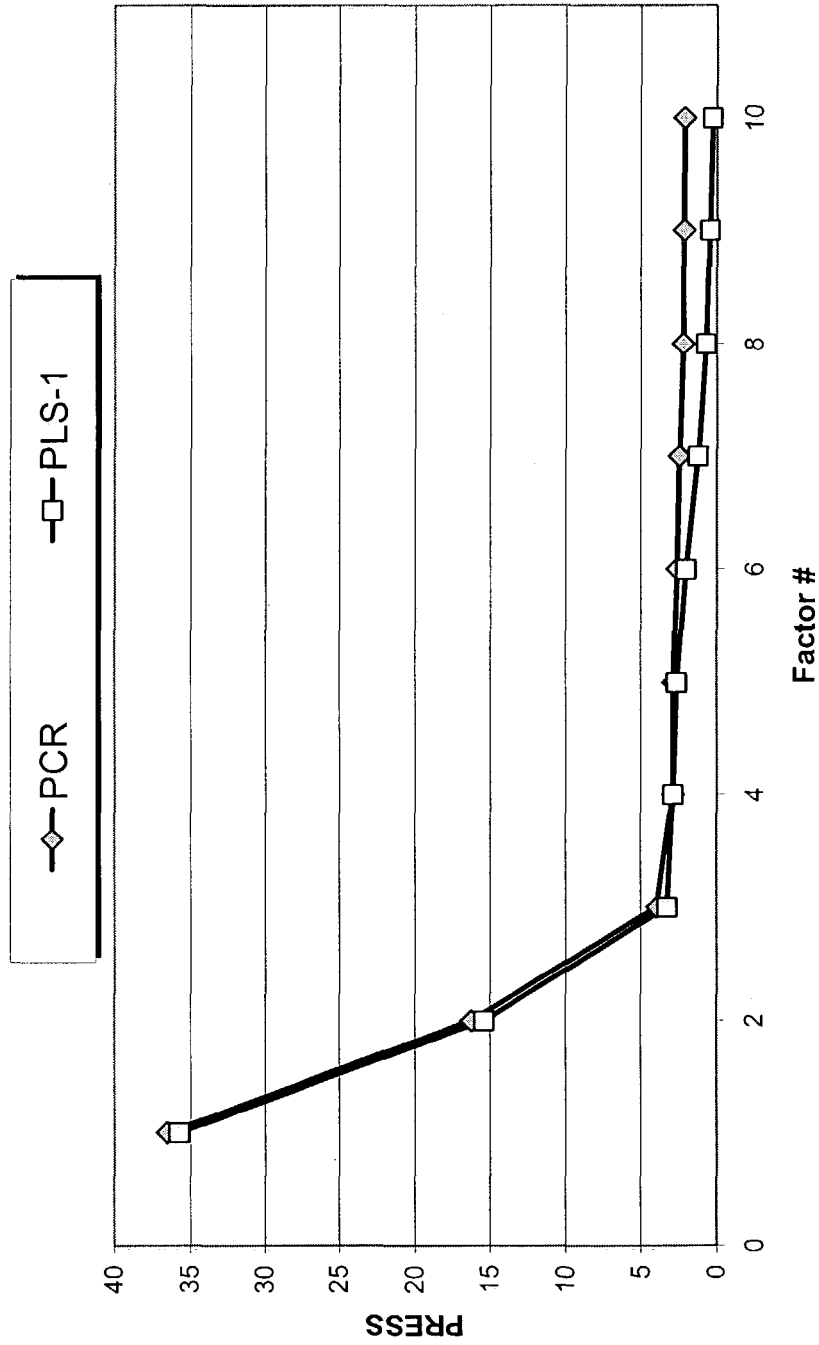
Figure 3a. PRESS (Equation 25) calculated for various number of factors for selfpredicted by PCR and PLS-1 for brightener concentrations (scan dq21cu, channel 2, range 670-765).

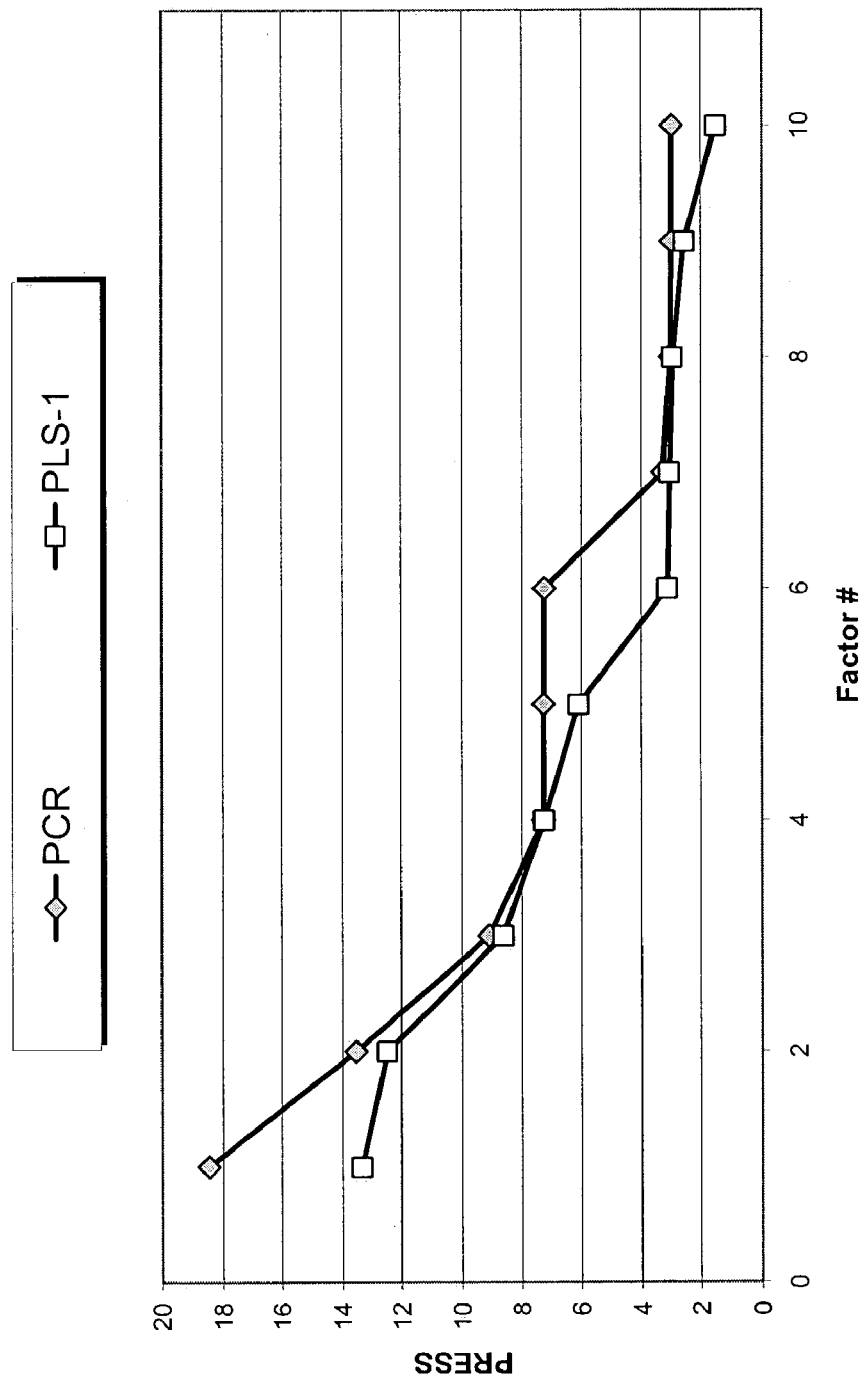
Figure 3b  PRESS (Equation 25) calculated for various number of factors for selfpredicted by PCR and PLS-1 carrier concentrations (scan dq21s4, ch 5, range 440-470).

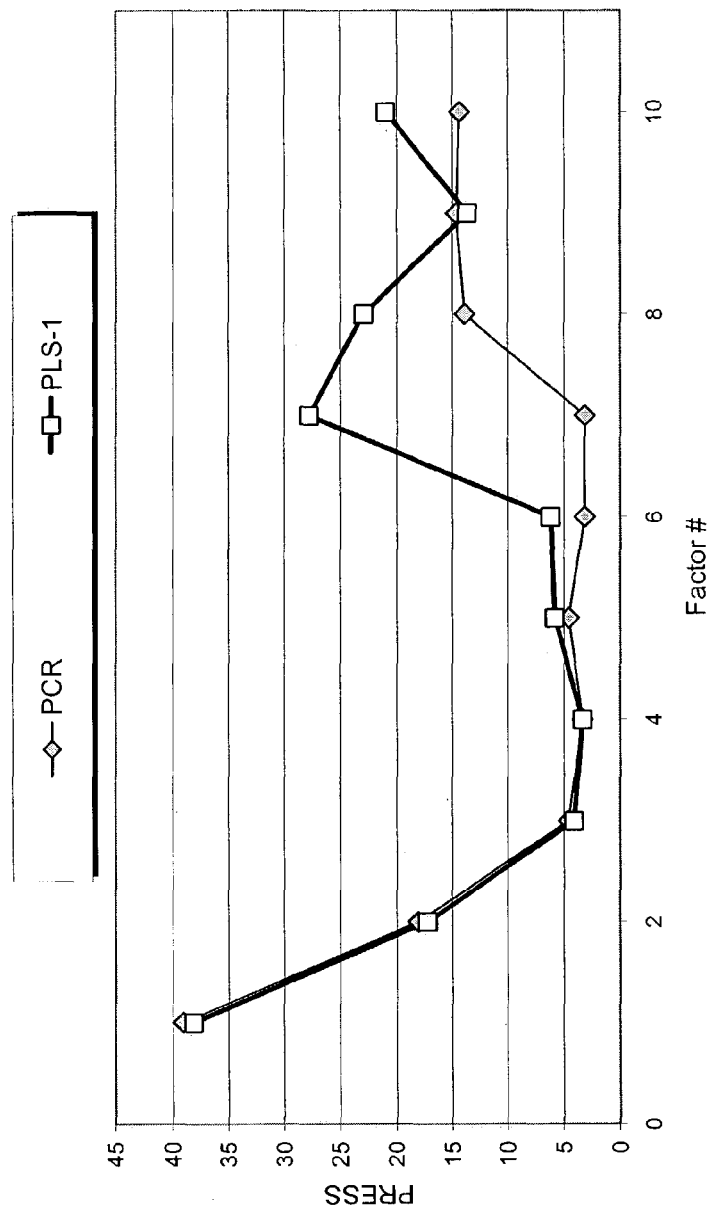
Figure 4a  PRESS (Equation 25) calculated for various number of factors for cross-validated by PCR and PLS-1 brightener concentrations (scan dq21cu, channel 2, range 670-765).

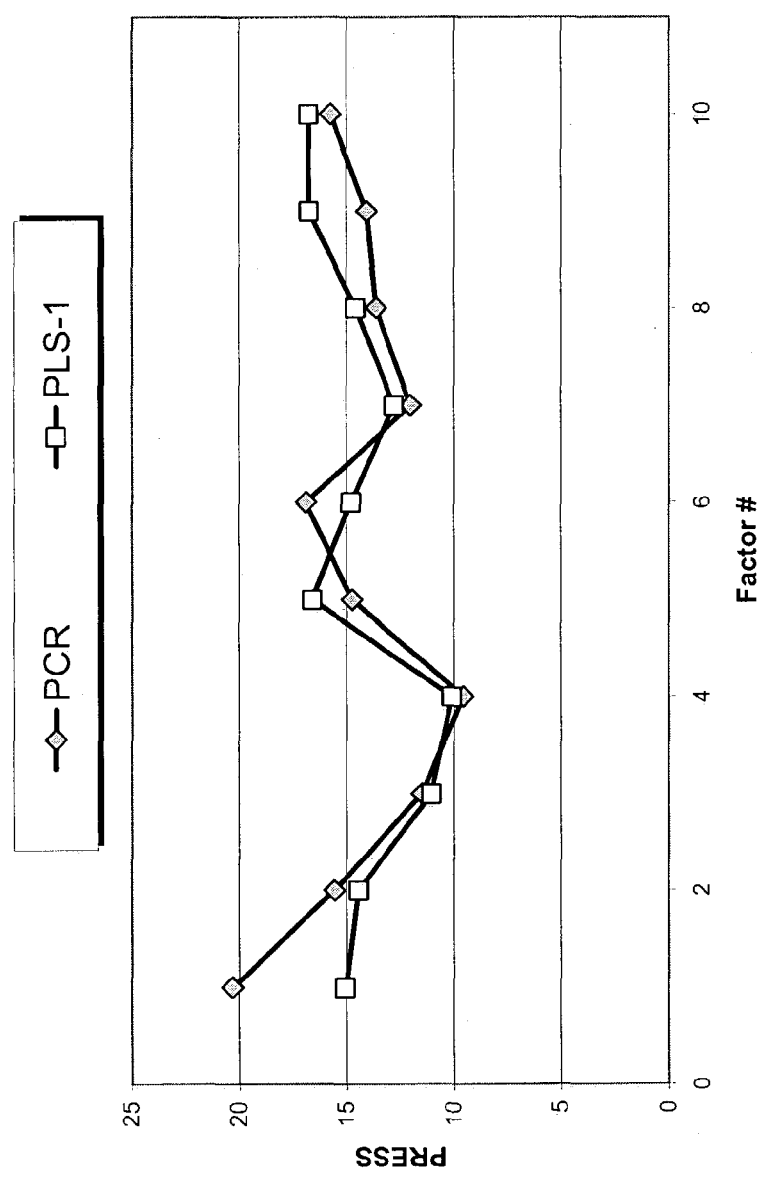
Figure 4b  PRESS (Equation 25) calculated for various number of factors for cross-validated by PCR and PLS-1 carrier concentrations (scan dq21s4, ch 5, range 440-470).

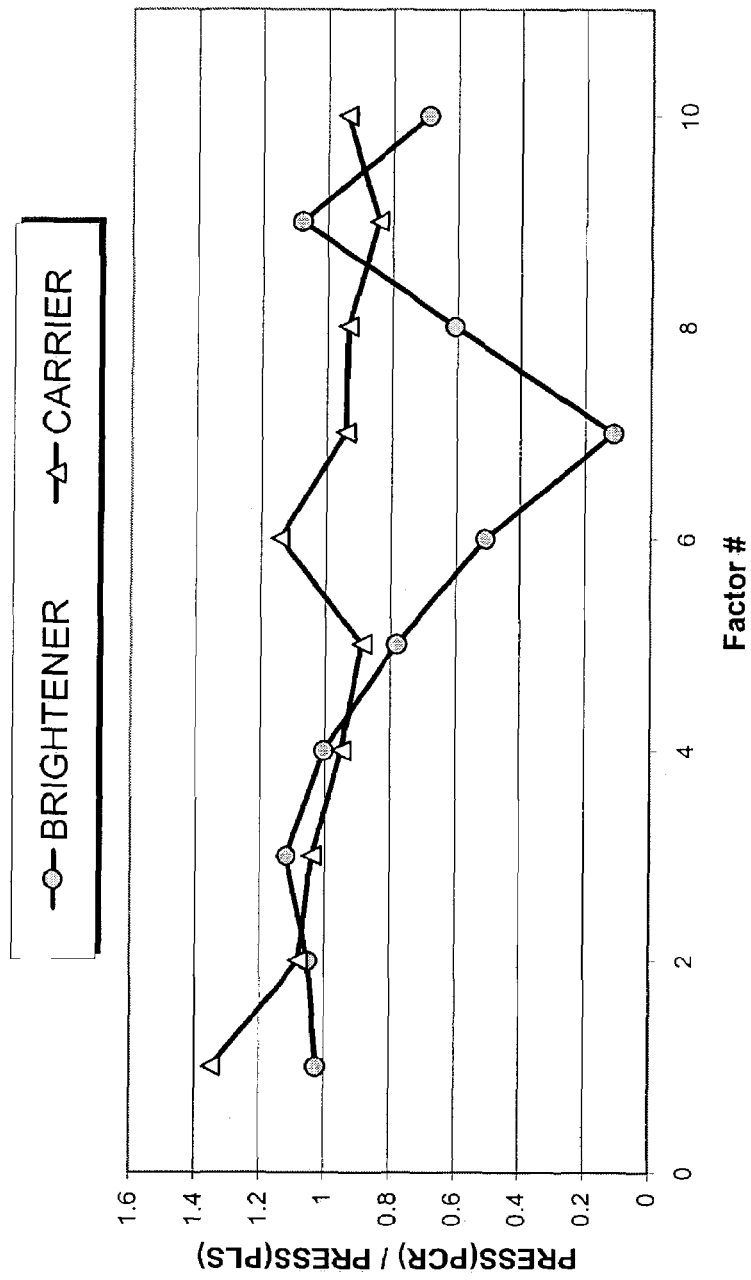
Figure 5  $F_{PRESS}$ (Equation 28) calculated for various number of factors for cross-validated brightener concentrations (scan dq21cu, channel 2, range 670-765) and carrier concentrations (scan dq21s4, ch 5, range 440-470).

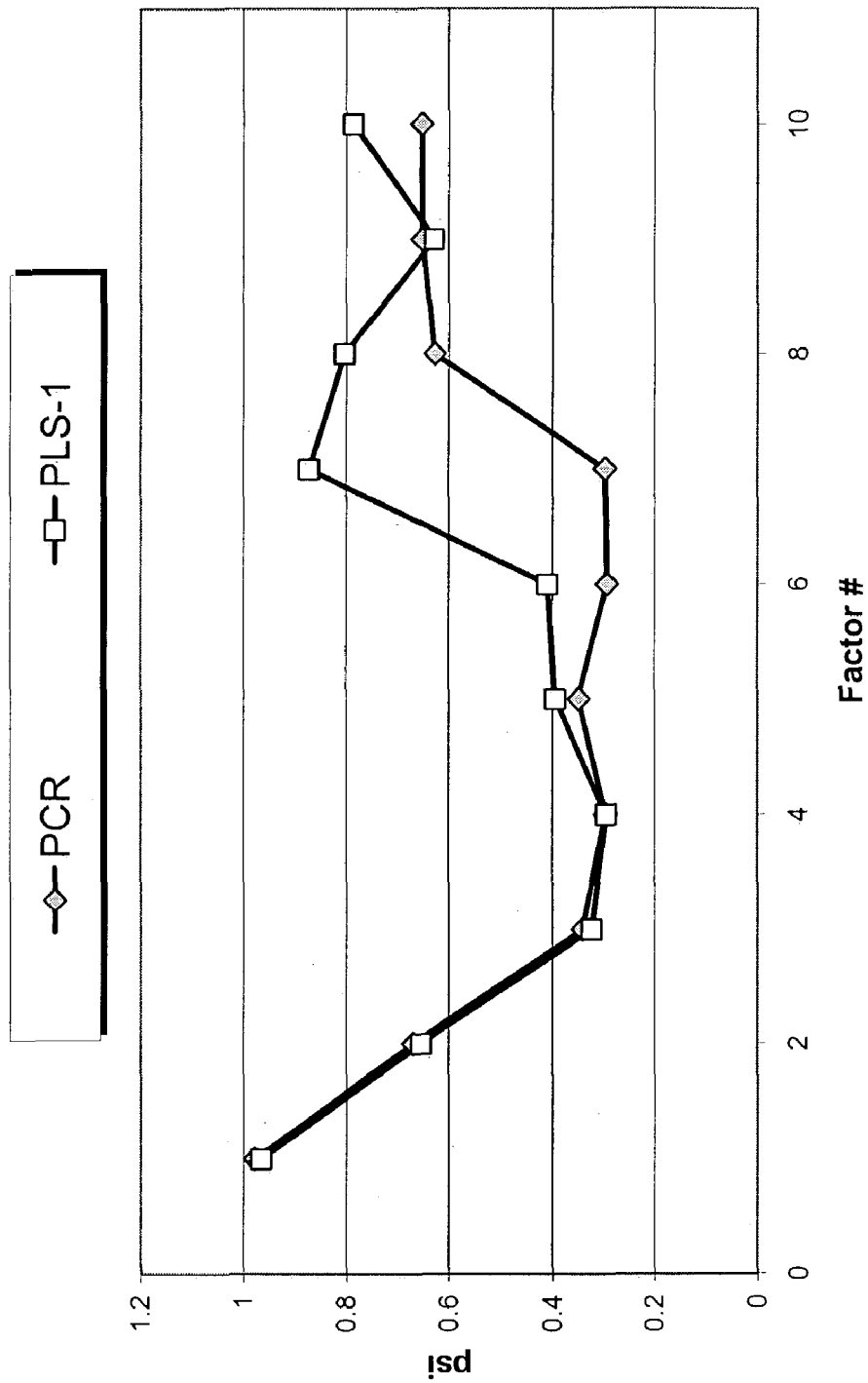
Figure 6a    Exner ψ function (Equation 29) calculated for the same concentration data as that of Figure 4a.

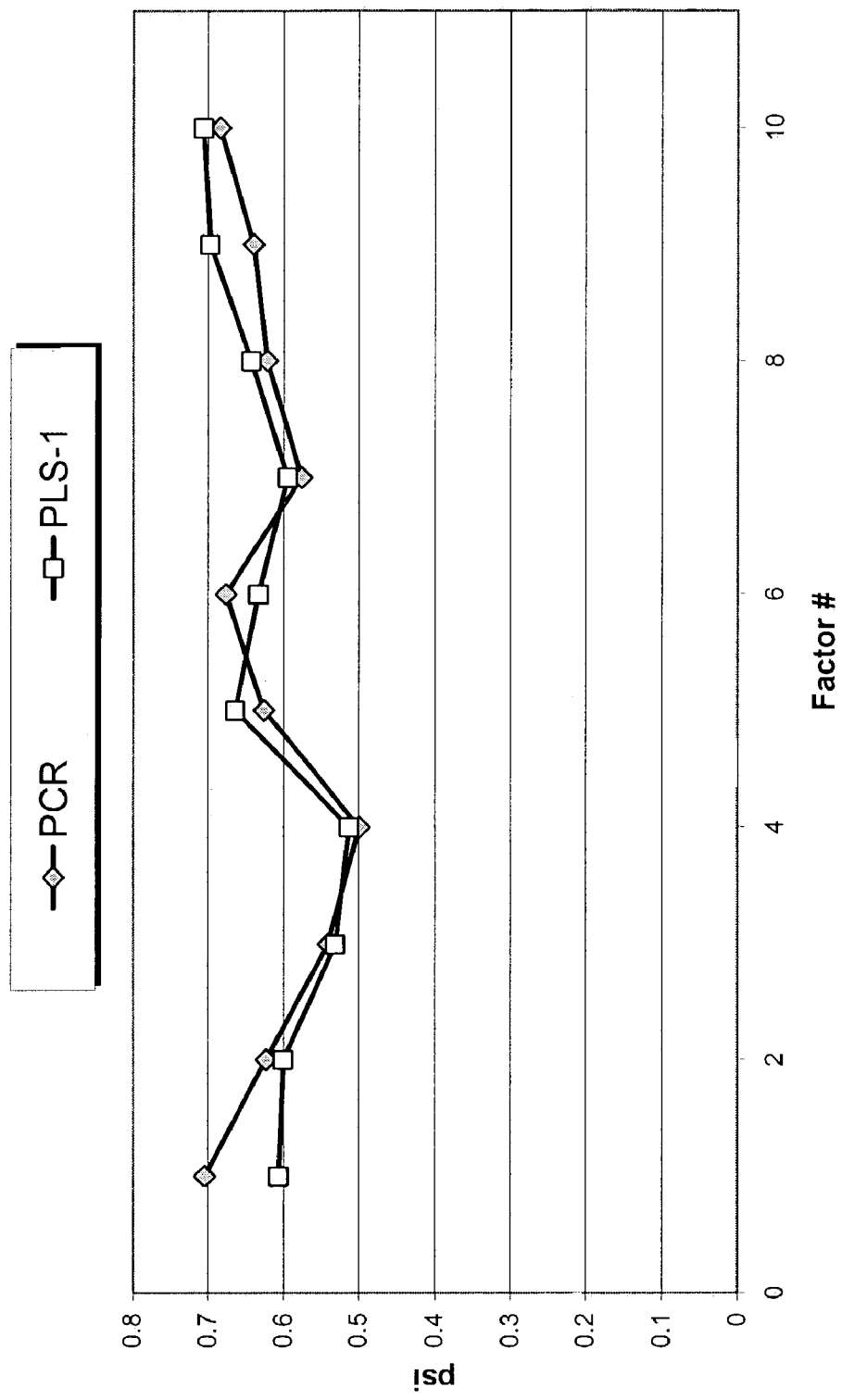
Figure 6b. Exner ψ function (Equation 29) calculated for the same concentration data as that of Figure 4b.

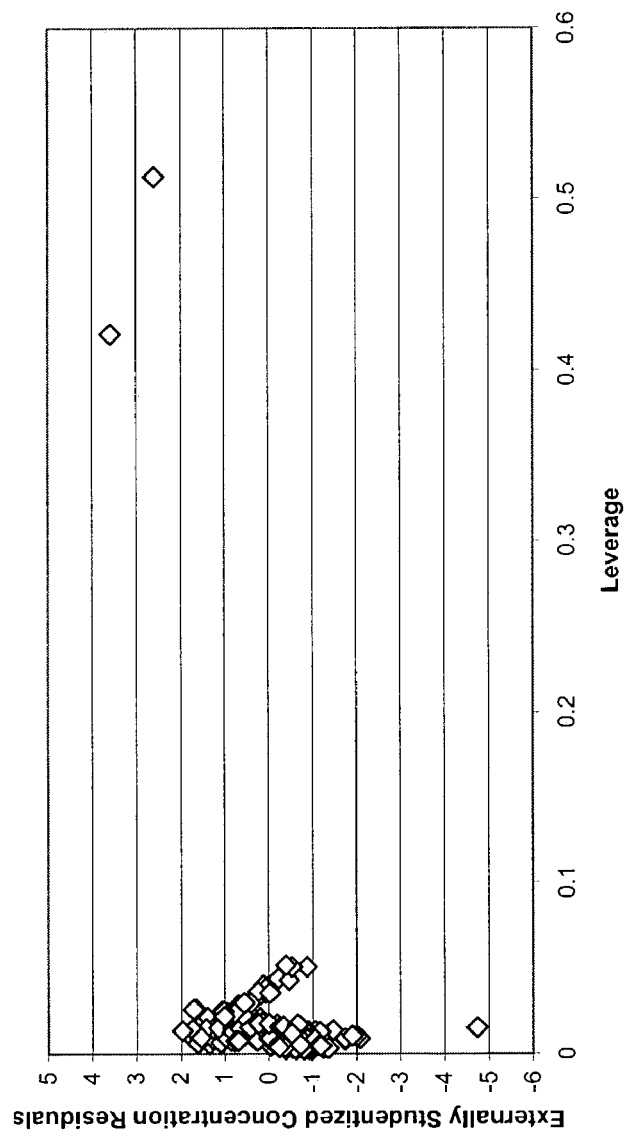
Figure 7. Plot of leverages versus externally Studentized concentration residuals for brightener (scan dq21ba2, channel 5, range 300-860, 4 factors).

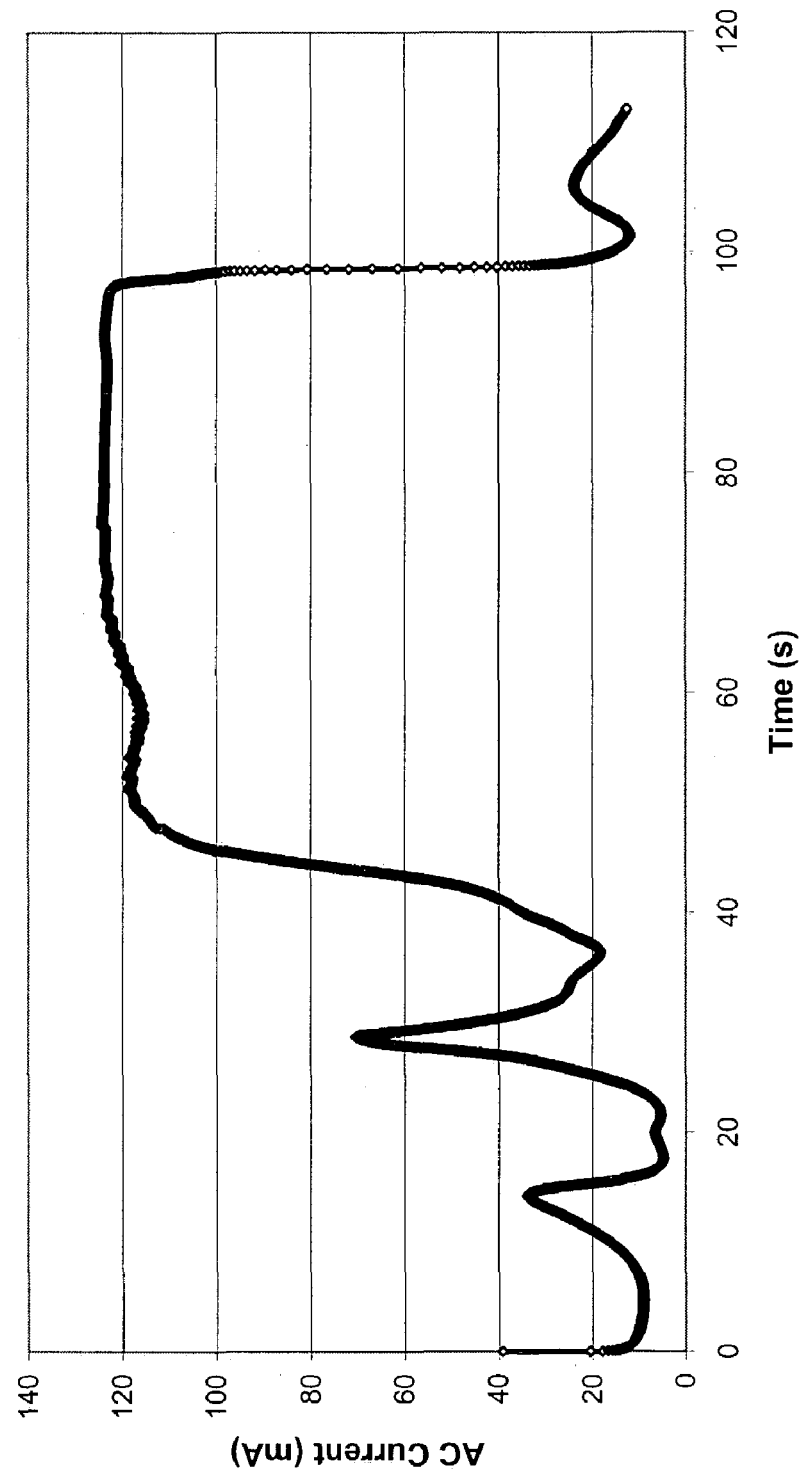
Figure 8. An example cyclic AC (X first harmonic) voltammogram scan dq21b26, ch3 for PC75 plating bath.

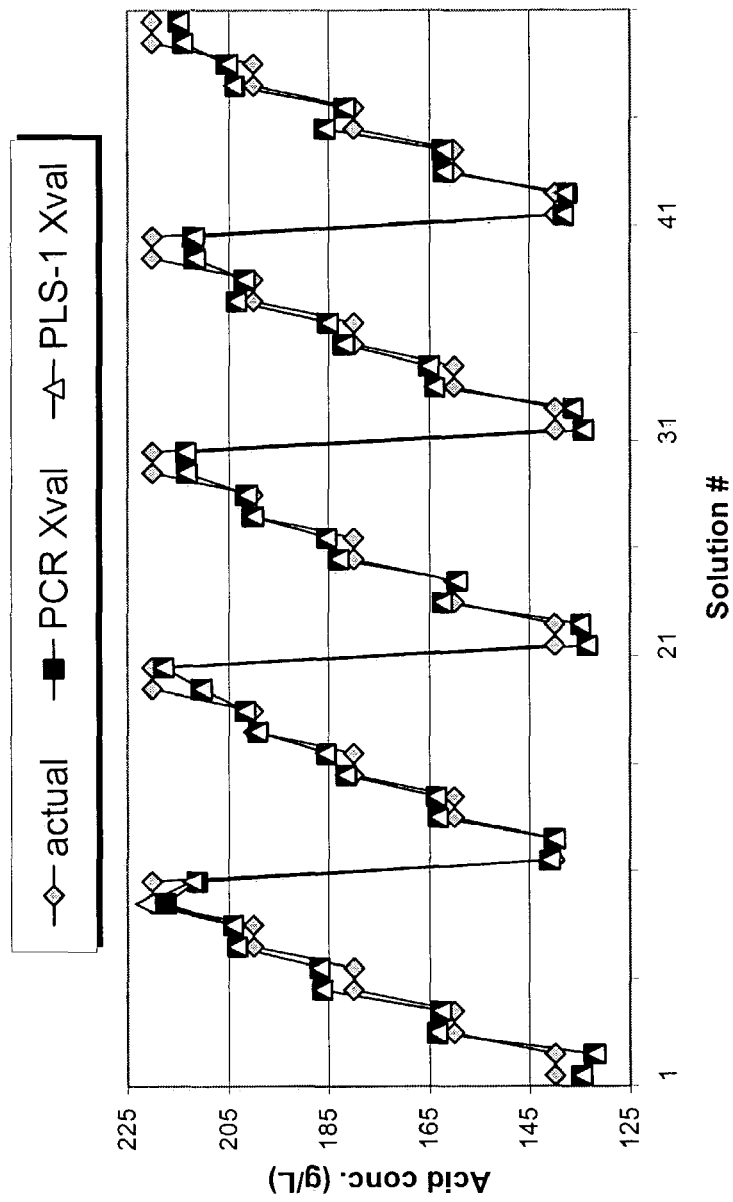
Figure 9  Actual (blue) and crossvalidated by PCR (green) and by PLS-1 (red) acid concentration values for PC75 plating bath calibration; scan dq21b26, ch 3, range 4000-4800, 3 factors.

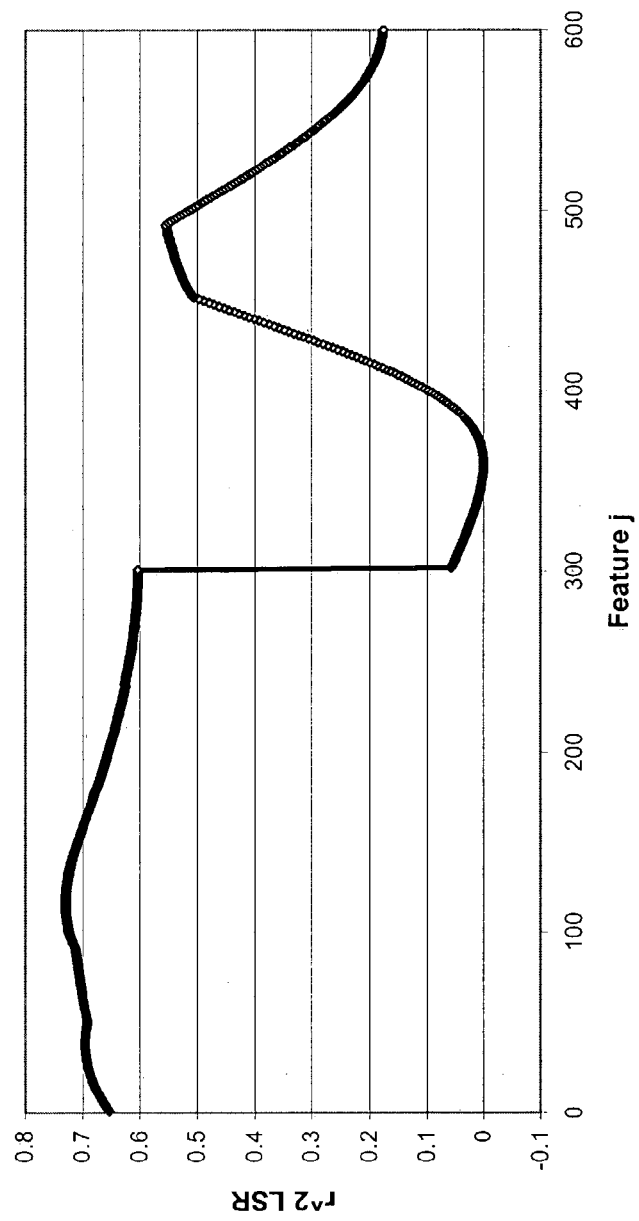
Figure 10. The squared correlation coefficients (Equation 36), $(r^o)^2$, for selfpredicted brightener concentrations. PC75 plating bath calibration obtained via least squares regression for part of the scan dq21ba2, channel 3, range 401-701 (first 301 points) glued with scan dq21ba2, channel 4, range (301-601) (last 301 points)

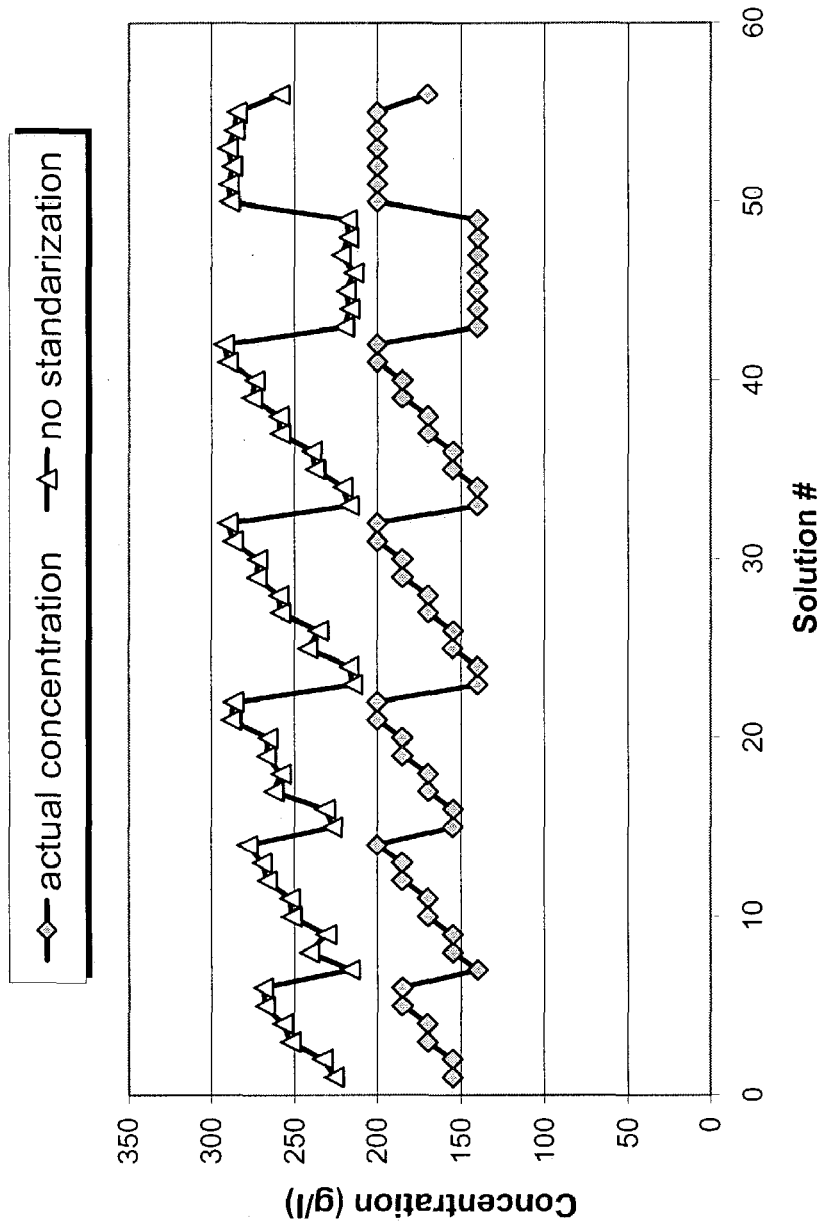
Figure 11a. Prediction of acid concentration on the secondary instrument calculated employing regression equation from the primary instrument without any standardization (scan dq21b26, channel 3, 3600-4350, 4 factors).

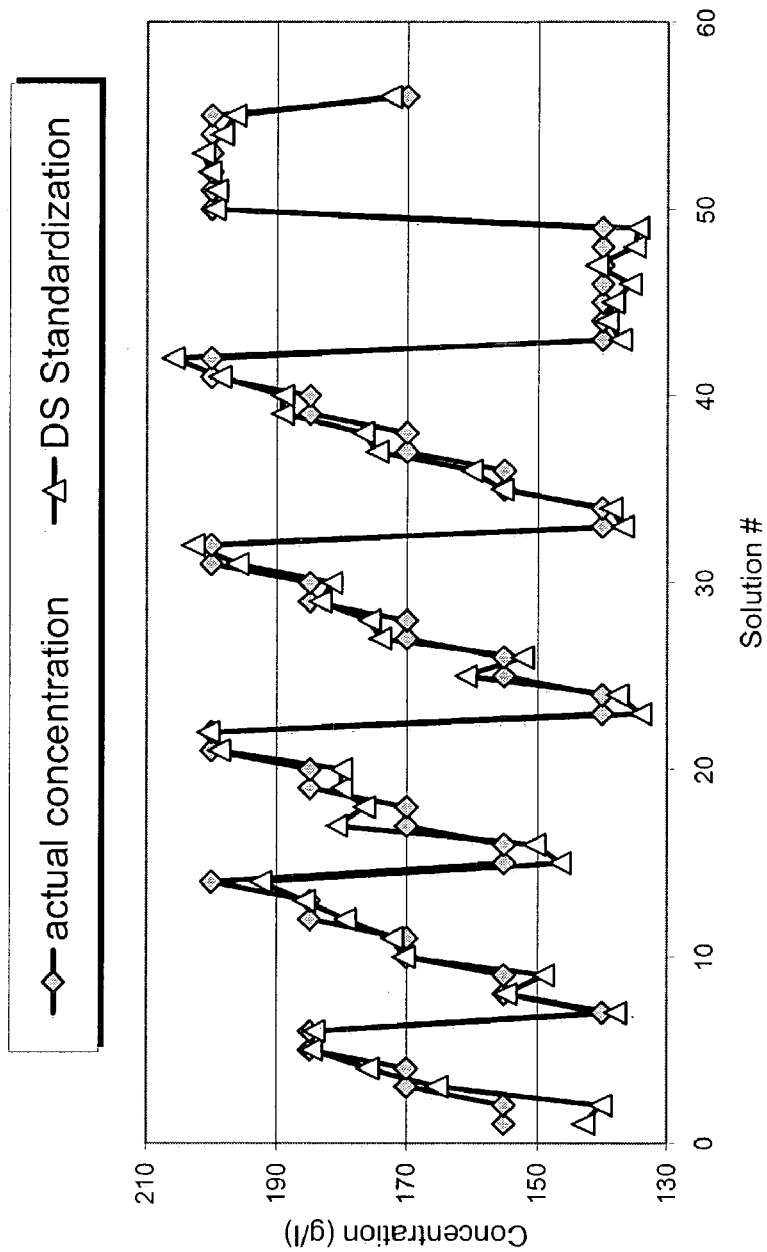
Figure 11b. Prediction of acid concentration on the secondary instrument calculated employing regression equation from the primary instrument standardized with DS (scan dq21b26, channel 3, 3600-4350, 4 factors).

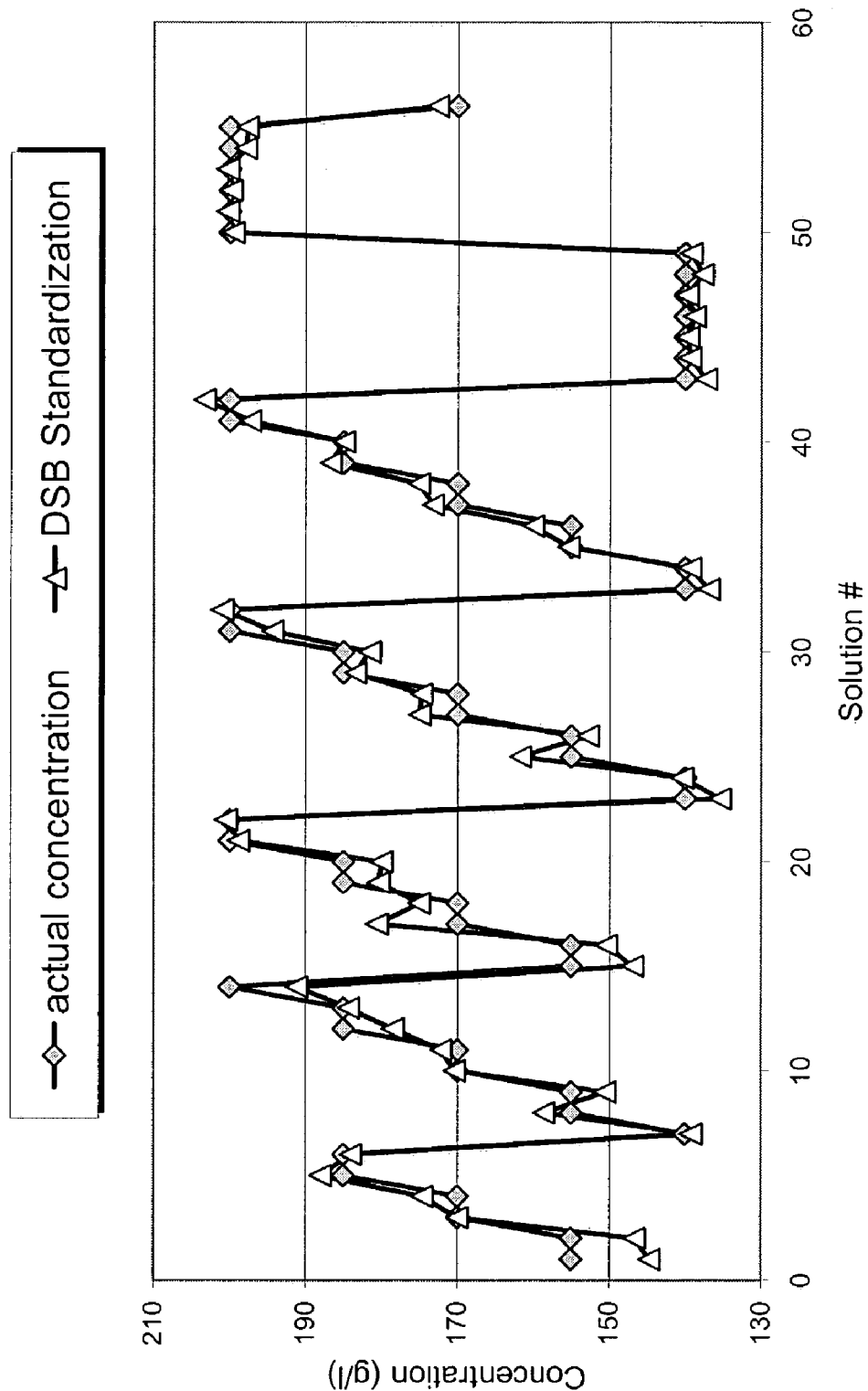
Figure 11c. Same as Figure 11b but standardized with DSB.

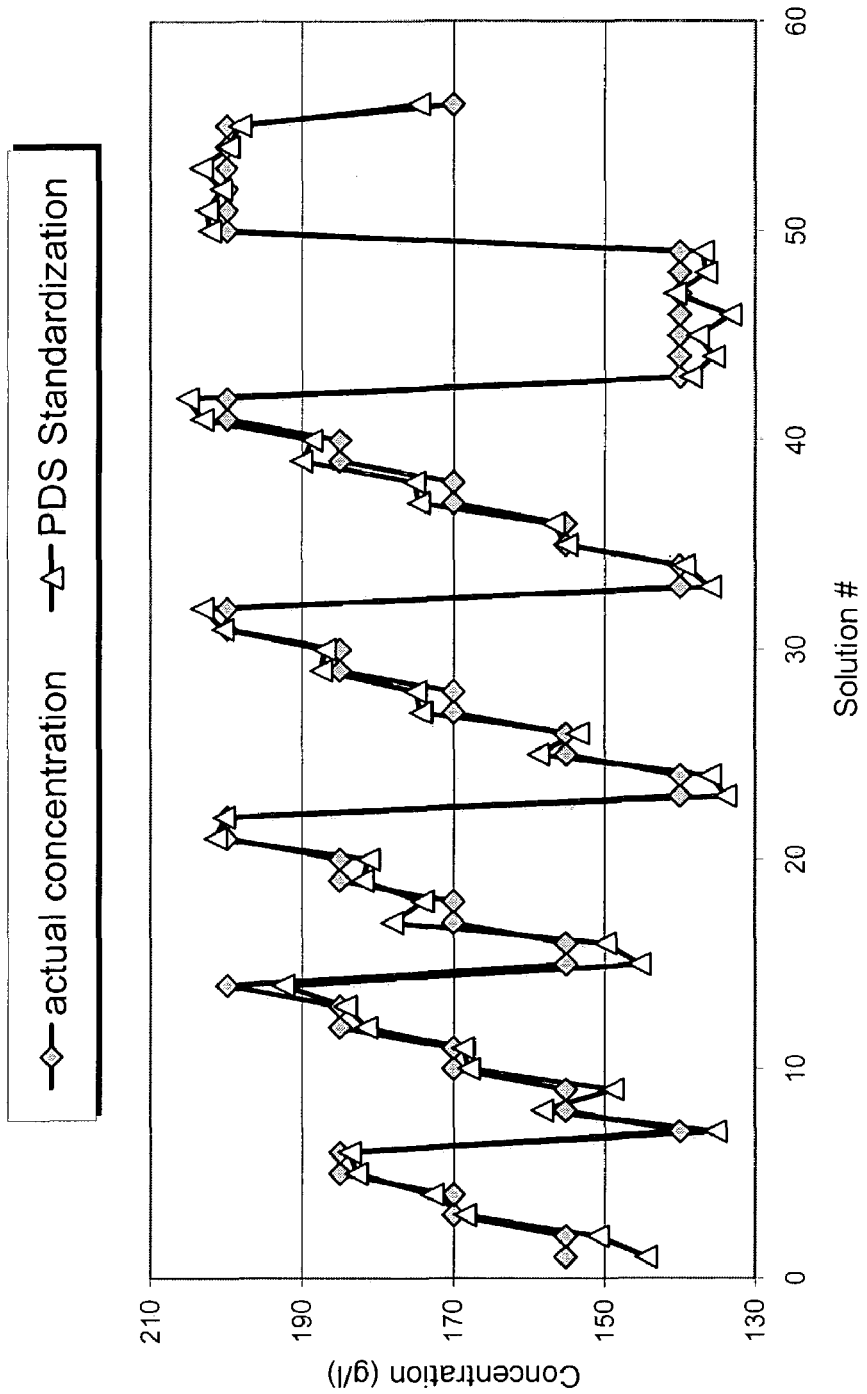
Figure 11d. Same as Figure 11b but standardized with PDS.

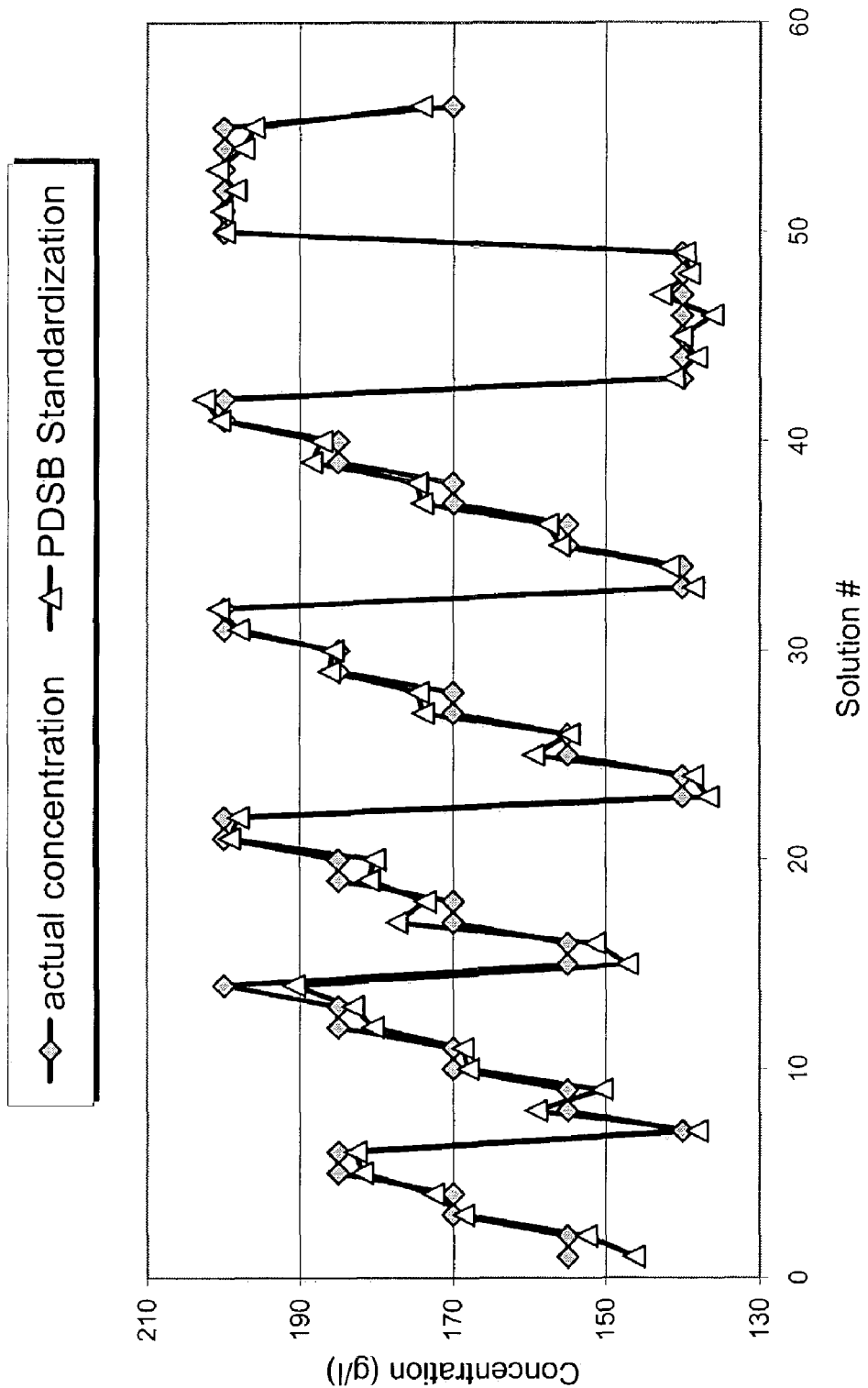
Figure 11e. Same as Figure 11b but standardized with PDSB.

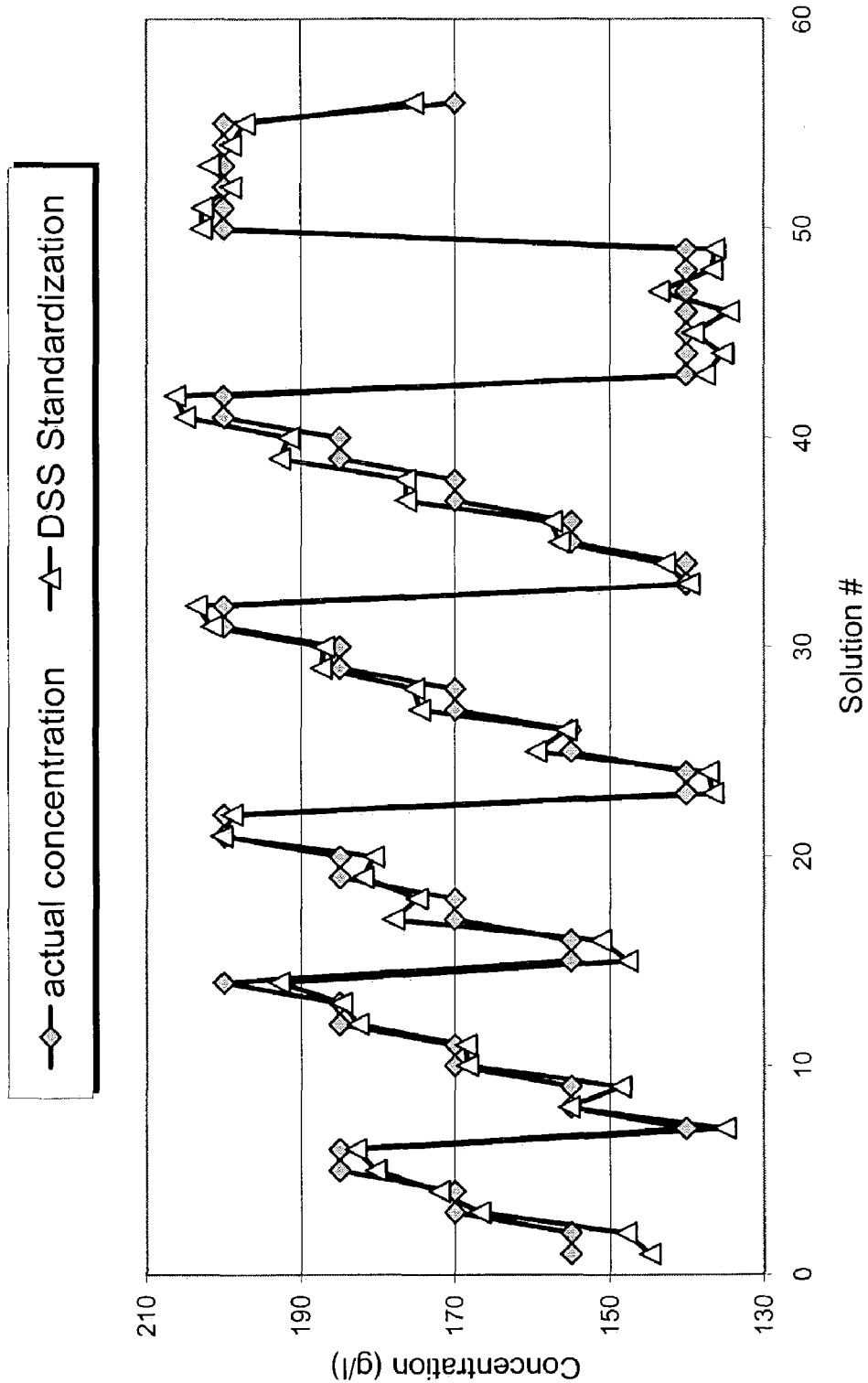
Figure 11f. Same as Figure 11b but standardized with DSS.

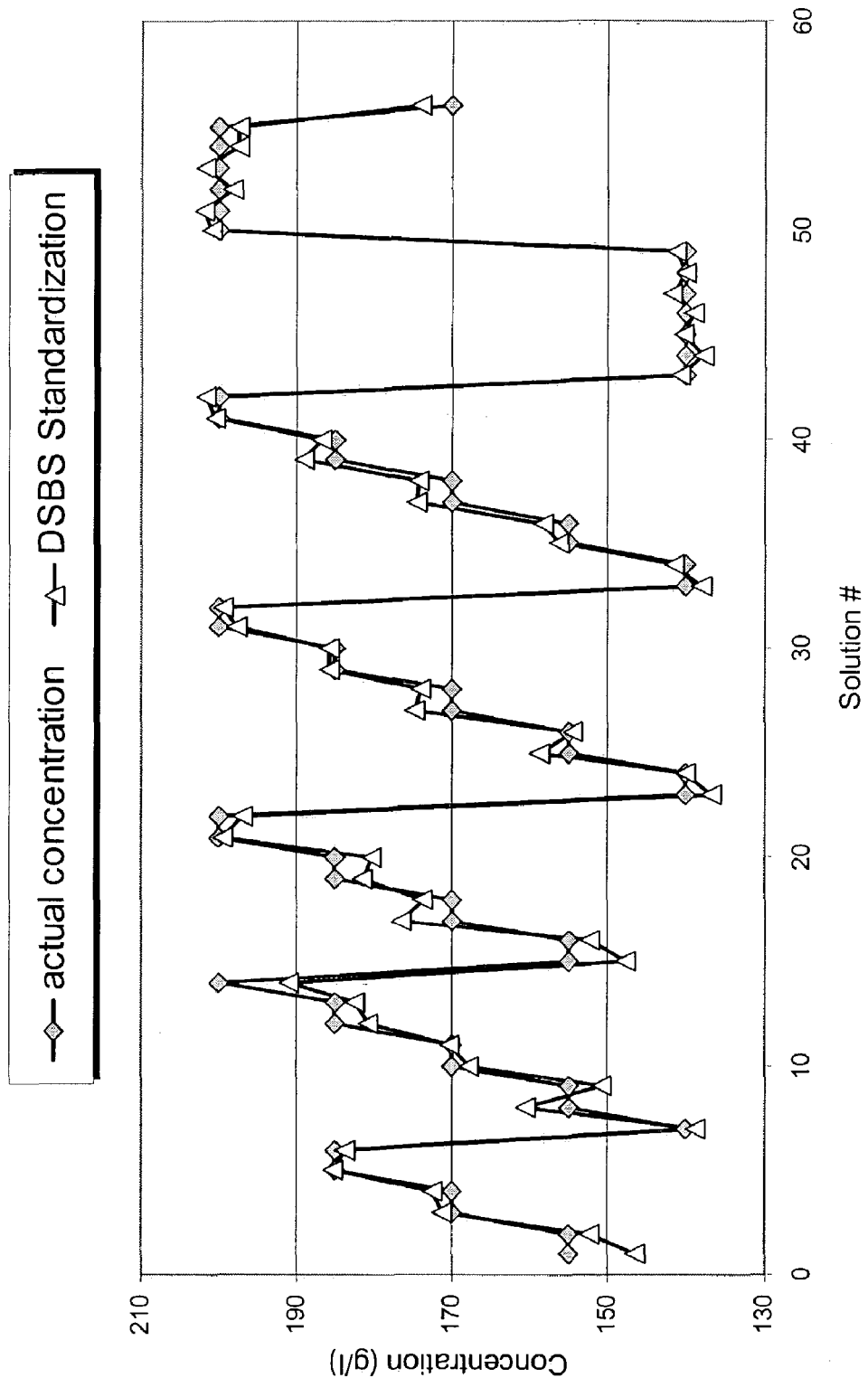
Figure 11g. Same as Figure 11b but standardized with DSBS.

METHOD AND APPARATUS FOR REAL TIME MONITORING OF INDUSTRIAL ELECTROLYTES

PRIORITY CLAIM

This application claims priority from commonly owned, copending U.S. Provisional Application Ser. No. 60/397,120, filed 19 Jul. 2002, the disclosure of which is hereby incorporated herein by reference.

FIELD OF THE INVENTION

The present invention relates generally to any electrolyte and methods for monitoring the constituents contained therein. More specifically, the present invention relates to plating baths and methods for monitoring the constituents contained therein based on chemometric analysis of voltammetric data obtained for these baths. More particularly, the method of the present invention relates to application of numerous chemometric techniques of modeling power, outlier detection, regression and calibration transfer for analysis of voltammetric data obtained for various plating baths.

DESCRIPTION OF RELATED ART

Methods for Analyzing Electroplating Baths

A typical plating bath solution comprises a combination of several distinct constituents which are broadly divided into major constituents and trace constituents. The major constituents typically make up about 2 to 50 percent of the total bath weight or volume. Trace constituents are present in smaller quantities, usually less than 1 percent of the total weight or volume. The techniques for the analysis of inorganic and organic constituents of plating baths usually appear separately in the literature. That is also the way they are briefly reviewed below.

Methods for Monitoring of Organic Constituents

Haak et al. [P1, P2] have developed a method known as cyclic stripping voltammetry (CVS). They employed the effect of inhibition of the rate of deposition caused by adsorption of additives on the surface of a platinum rotating disk electrode during cyclic electrodeposition. Such inhibition is quantified by measuring the decrease of the anodic charge involved in the CV stripping peak. A decrease in deposited charge is correlated with an increase in concentration of the additives. CVS is the most commonly used technique today [P3]. Despite claim that CVS can be used as a monitoring tool (and the availability of the commercial CVS instrument), many serious questions about the technique still arise. The CVS method is not an analytical procedure as the term is generally understood: it is not specific for a given chemical compound, and the relationship between measured charge and solution concentration is not direct. The method does not measure a quantity that can be directly related to the concentrations of components of a known solution. Additionally, one quantity, a charge, is used to estimate the solution concentration of a multicomponent additive. In addition, CVS measures the aggregate effects of all of the additive components. For CVS monitoring to be useful, the ratios of the components of the additive system must remain constant as the additive is consumed. Some effort has been made to use the technique to determine the individual components of a multi-component additive [P4], but it is questionable whether such a procedure can be the basis of plating solution control. CVS is not suitable for continuous analysis of some baths due to contaminant buildup formation at the working electrode which affects adsorption of additives.

Tench and White introduced a technique called Cyclic Pulse Voltammetric Stripping (CPVS) [P5]. This method involves sequentially pulsing the electrode between appropriate metal plating, metal stripping, cleaning, and equilibrium potentials whereby the electrode surface is maintained in a clean and reproducible state. This method overcomes the problem of contaminant buildup in the copper plating bath affecting the copper deposition rate which interferes with brightener analysis.

An improvement of CVS and CPVS method is found in [P6]. In accordance with the invention, in order to prevent contaminant buildup on the electrodes, a pause without applied potential is used following each completed cycle. During either this applied potential or the open circuit condition, contaminants are either eliminated from the electrode surface or fail to deposit on the surface.

Eliash [P7] demonstrated an in-situ method involving applying a brief voltammetric plating signal to a pretreated electrode, applying a rapid stripping signal to the plated electrode, and monitoring the resultant stripping signal response current whose characteristics indicate the particular trace constituent concentration level.

Sonnenberg et al. [P8] have developed a direct method of analyzing brighteners and levelers based on the differential adsorption of these additives on a working electrode during a sequence of steps prior to and during metal plating. The sensitivity of the method allows for the determination of both brightener and leveler in the same sample without cyclic processing.

Chang et al. [P9] have developed a cyclic voltammetric (CV) method for measuring the concentration of an unknown subcomponent in the additive mixtures in a plating solution. The performance of the method is demonstrated using the example of an acid copper plating bath. The method is based on measurements of cathodic copper plating charge for different volumes of added unknown mixture to the calibration solution which contains the component of interest in a known concentration near that which would be expected in the unknown. The slopes of the calibration standard curve and the unknown mixture curve are also compared.

All methods presented above require a rotating disk electrode and controlled bath hydrodynamics.

Chang et al. [P10] have developed a method for analyzing organic additives in methane sulfonic acid based solution for electroplating of Pb—Sn alloys. The method is based on standard addition measurements of the height of the peak of square wave voltammograms obtained at a hanging mercury drop electrode (HMDE). The major drawback of this method is the use of mercury electrodes, which create environmentally dangerous waste and need to be operated and maintained by highly qualified personnel.

Ludwig [P11] developed a method based on AC voltammetry by measuring AC current in relation of varying dc potential to express it as an AC current spectrum (or fingerprint). The spectra obtained contain fine structure and enable monitoring of minor plating bath constituents. AC voltammetry was utilized to monitor organic additives in-situ, without any sample preparation and/or utilization of standard solutions.

Bonivert et al. [P12, P13] have developed an in-situ electrochemical detection method, which employs a Tuned Frequency Impedance Probe (TFIP), to measure dilute concentrations of surfactants in plating solutions. Current due to a modulation voltage flows from the counter electrode through the increased resistance at the working electrode. The increased resistance at the working electrode causes the phase of the voltage applied to the inverting input of an amplifier to lag with respect to the phase of the modulation voltage. The phase of the output voltage from the amplifier is compared to the phase of modulation voltage using a lock-in amplifier. The result of the comparison, the phase difference, is output as a voltage signal from the amplifier to a utilization device. This voltage correlates directly to the surfactant concentration adsorbed on working electrode.

A quantitative analytical technique, chromatography, is available for some of the components of some electroplating solutions [P14]. HPLC has the potential advantage of being able to detect individual ionic components of the additive in the plating bath. However, analysis methods and separation columns are not available for many of the commercial additives on the market today. Also, some additives may require sample preparation before HPLC analysis can be performed. Additionally, the aggressiveness of the bath samples limits the lifetime of chromatographic columns to several hundred analysis increasing therefore maintenance costs.

Newton and Kaiser [P15] presented current developments on applications of liquid chromatography techniques for determination of additive concentrations and contaminant analysis. They also discussed increasing requirements (mostly setup by the semiconductor industry) for the purity, plating effectiveness and plating speed of electroplating bath chemicals.

Horkans and Dukovic [P16] conducted a comparative study on determination of concentration of SPS-based additives in copper plating baths using CVS and HPLC. They noticed that although CVS due to its convenience is more common than HPLC for integration with plating tools, it is not a selective technique (in contrast to HPLC) for suppressor concentration determination. All species (both these deliberately added and degradation products) similarly affecting Cu deposition kinetics are lumped together in the CVS determination of concentration. They also noticed that CVS and HPLC methods agree in SPS analysis only in standard solutions or in unused plating baths.

Methods for Monitoring of Inorganic Constituents

Techniques for monitoring the major constituents of plating baths typically involve removing a sample of the chemical solution from the plating tank for subsequent wet chemical analysis. Wet chemical analysis methods must usually be performed by highly skilled personnel. Specialized and costly chemical analysis equipment and supplies are required. Furthermore, the delay between drawing samples and receiving measurement results can be anywhere from several hours to several days. The slow response time of wet chemical analysis limits the extent to which a high quality and high-speed plating bath can be continuously maintained.

Another off-line method applied in the analysis of metals in the plating bath is X-ray fluorescence. This method is very precise and competitive to wet chemical techniques in terms of accuracy, especially for metals that lack reliable wet chemical methods. Unfortunately, X-ray fluorescence shares all the disadvantages of wet chemical methods discussed in the previous paragraph as well as the high cost of the equipment.

On-line methods for major constituents have been developed, and are routinely used despite their high cost and inconvenience in that often the solution must be pumped out of the plating tank into equipment of substantial size and complexity. Sometimes reagent solutions are automatically mixed with the pumped solution. Usually there is no room on a plating floor for close proximity of such equipment. Also, the complexity of the automatic solution mixing and preparatory analytical steps results in low reliability (due to, for instance, reagent instability and rinsing cross contamination) and high cost. In addition, and perhaps of paramount importance, is that the methods and equipment are not universal in application, and therefore cannot be used for all the plating tanks in the plating shop. Methods included in these real-time, but low practicality procedures are ion-chromatography, differential pulse polarography (DPP), cyclic linear sweep voltammetric stripping (CVS), optrodes, and UV fluorescence.

Eliash et al. [P17] have developed the method of monitoring in-situ and on-line metal ion content. The method involves applying a sweep signal to the pretreated working electrode, and measuring the DC voltammetric peak current of the resulting response signal. The DC voltammetric peak current is proportional to the metal ion content of the plating bath.

Phan et al. [P18] have developed a method based on DC-and-AC voltammetry for real-time in-situ monitoring of major constituents in plating baths. The concentration of major constituents is determined based on the peak current of DC-and-AC voltammograms.

Ludwig et al. [P19] have developed a method of monitoring acid concentration in plating baths. The AC response current provides an accurate indication of the acid concentration within the solution.

Application of Chemometric Techniques in Electrochemistry

Routine applications of chemometric methods abound in the literature of analytical chemistry, but only a small fraction of this literature has been devoted to the field of electrochemistry [L1]. Although the number of groups employing chemometric methods in electrochemistry has been limited, there has been some good progress made by them. A brief overview appears below of a selection of chemometric methods used in novel ways in the field of electroanalytical chemistry, which have appeared throughout the last ten years.

Calibration and Resolution

Calibration refers to the process of relating the analyte concentration or the measured value of a physical or chemical property to a measured response.

This section is also partially concerned with the mathematical resolution of mixtures. A mathematical resolution of mixtures is usually performed in far less time than a physical or chemical separation.

Henrion et al. [L2] reported application of Partial Least Squares (PLS) regression to resolve quantitatively overlapping responses obtained from differential pulse anodic stripping voltammetry (DPASV).

Ni et al. used PLS and Principal Component Regression (PCR) [L3] and iterative target transformation factor analysis (ITTFA) [L4] to resolve the overlapping polarograms of organic compounds, pyrazine and its methyl derivatives. Ni et al. also applied PLS and PCR [L5] and ITTFA [L6] to resolve the voltammograms of quaternary mixture of Amaranth, Sunset Yellow, Tartrazine and Ponceau 4R which present overlapped peaks. Ni et al. [L7] employed PLS and PCR to resolve overlapping linear sweep voltammetric (LSV) peaks of oxidation obtained for quaternary mixture of synthetic food antioxidants: butylated hydroxyanisole, butylated hydroxytoluene, propyl gallate and tert-butylhydroquinone at a glassy carbon electrode. Ni et al. [L8] also used the same chemometric techniques for interpretation of complex differential pulse stripping voltammograms of antipsychotic drugs: chlorpromazine hydrochloride and promethazine hydrochloride obtained at a glassy carbon electrode.

Alonso Lomillo et al. [L9] employed PLS regression for the resolution of the overlapping DPP signals from a ternary mixture of drugs: rifampicin, isoniazid and pyrazinamide. The authors applied genetic algorithm to select some of the predictor variables (potentials of the polarogram).

Allus and Brereton [L 10] used a chemometric approach to linear calibration to determine thallium in cement dust and sediment samples using anodic stripping voltammetry.

Reviejo et al. [L11] applied PLS regression to polarographic analysis of emulsified mixtures in any combination of four organochloride pesticides, using a calibration set of 35 samples, with current measurements at nine different potentials.

The study of Jagner et al. [L12] demonstrates that there are significant advantages to be gained by using multivariate calibration in electroanalysis of systems with several interfering components. They were able to determine arsenic by stripping analysis in the presence of multiple interfering species that, with the conventional univariate calibration methods used by most electrochemists, would have rendered the analysis useless. The abilities of the PLS in the resolution of binary and ternary mixtures of organic compounds by using their DPP signal were reported by Cabanillas et al. [L13, L14, L15]. The PLS-1 method was found by Guiberteau et al. [L16] to provide satisfactory calibration for indirect differential pulse voltammetric (DPV) determination of the carbonate pesticides: carbaryl and carbofuran. The same group used PLS to calibrate sampled direct current, DPV and cyclic voltammetric (CV) data for binary and ternary mixtures of phenolic antioxidants used in the food industry [L117]. The calibration was externally validated on packet soup samples. Guiberteau Cabanillas et al. [L18] utilized PLS and artificial neural networks to determine each component in the following binary mixtures: atrazine-simazine and terbutryn-prometryn based on their overlapping polarographic signals data. Lastres et al. [L19] and Chan et al. [L20] applied neural nets to calibration problems in solving interference caused by the formation of intermetallic compounds in anodic stripping.

Richards et al. [L21] demonstrated optimization of a neural network model for the calibration of dual pulse staircase voltammetric data for a ternary aliphatic mixture of ethanol, fructose and glucose. In order to reduce training time, the number of network inputs was reduced by application of PCA and data scores instead of original data were used as input.

Wehrens and van der Linden [L22] employed neural networks to calibrate a voltammetric sensor consisting of an array of modified microelectrodes. Linear calibration methods, like PCR, did not yield good results because of the inherent non-linear nature of the LSV data for mixtures of ortho-, meta-, and para-dinitrobenzene, and monosubstituted nitrobenzene. Matos et al. [L23] conducted flow injection amperometric quantification of ascorbic acid, dopamine, epinephrine and dipyrone in mixtures by using an array of modified microelectrodes. The experimental results were analyzed using multiple linear regression technique.

In numerous papers coming from Esteban's group, factor analysis techniques were applied to the electroanalytical study of metal ion interactions with macromolecular ligands such as polycarboxylates, yielding slow mobile complexes [L24], cysteine-containing peptides yielding very strong complexes with heavy metals [L25-L31], monomeric weak complexing agents, such as carboxylates, yielding consecutive labile complexes with low formation constants [L32], strong complexing ligands, such as nitrilotriacetic acid (NTA), which yield 1:1 metal complexes showing either labile or inert characteristics depending on the different time window of the technique used [L33]. The major part of these studies was performed by DPP, because of its high resolution, although DPASV and normal and reverse pulse polarographic techniques were also used. Metal-binding properties of the peptides were studied on the example of cadmium complexes analyzed with LSV [L34] and CV [L35] which are considered to be the most effective and versatile electroanalytical techniques. These, however, have a drawback connected with poor resolution of overlapping signals. DPP and direct current polarography techniques were employed in the study of three successive Zn-glycine complexes [L36], the first two being electrochemically labile and the third one being inert. In all cases discussed in this paragraph, multivariate curve resolution with alternating least squares (MCR-ALS) was used. Diaz-Cruz et al. [L37] demonstrated the potential usefulness of voltammetry in combination with hard- and soft-(MCR-ALS)-modeling data analysis for the study of peptide complexation equilibria of metal ions such as Zn which have neither relevant spectroscopic properties nor proper isotopes for NMR measurements. Fernandez et al. [L38] showed that a soft modeling approach for the voltammetric data analysis for labile $Cd^{2+}$- and $Pb^{2+}$-glycine complexes provides good estimations of the complexation parameters as verified by the classical DeFord-Hume method. Soft modeling proved also useful for analysis of complex polarographic data applied to the study of the copper-binding ability of tannic acid in the presence of simultaneously occurring phenomena such as electrodic adsorption, overlapping signals or stabilization of intermediate Cu(I) species [L39]. Esteban et al. [L40] presented a general overview of the application of the MCR-ALS method to metal complexation studies by voltammetric techniques, mostly by DPP. Diaz-Cruz et al. [L41] employed MCR-ALS for analysis of DPP signals measured for systems $Zn^{2+}$+glutathione and $Cd^{2+}$+1,10-phenanthroline. These systems, respectively, yield two and three successive and electroactive complexes, which are inert in the time scale of electrochemical experiment.

Berzas et al. [L42] compared the applicability of two multicomponent analysis methods, square wave voltammetry by PLS and adsorptive stripping square wave voltammetry by PLS, to the resolution of overlapping reduction peaks corresponding to the reduction processes of sulphamethoxypyridazine and its synergetic potentiator, trimethoprim to conclude that the stripping of adsorbed species proved to be more sensitive.

Saurina et al. [L43] employed PCR and PLS for calibration calculation of the CV data for a mixture of oxidizable amino acids (cysteine, tyrosine and tryptophan) at a graphite-methacrylate composite electrode obtaining satisfactory results for cysteine and tryptophan.

Herrero and Cruz Ortiz [L44] used the piecewise direct standardization (PDS) method for PLS calibration model transfer in order to incorporate the temporal changes of the system due to formation of numerous intermetallic compounds affecting the polarographic determination of copper, lead, cadmium and zinc. The same authors [L45] applied PLS regression to the simultaneous determination of thallium and lead by DPASV. In this paper Herrero and Cruz Ortiz [L45] used PDS in order to transfer the calibration model from one day to another. Herrero and Cruz Ortiz [L46] employed PLS regression to a calibration problem where, in addition to electrode reactions that give the DPP peaks, a coupled chemical reaction, dimerization, coexists. The investigated component was benzaldehyde. The same authors [L47] employed the PLS regression in order to solve the significant matrix interference caused by iron in the copper determination by DPASV. Application of two standardization procedures, PDS and global calibration transfer was also demonstrated in this paper [L47].

Herrero and Cruz Ortiz [L48] applied a genetic algorithm as a variable selection method in the multivariate analysis with PLS regression of several DPP and DPASV data sets, where various interferences are present (coupled reactions, formation of intermetallic compounds, overlapping signals and matrix effect).

Sanz et al. [L49] developed a procedure for determining the capability of discrimination and evaluated this procedure using PLS calibration of benzaldehyde calculated based on DPP data.

Signal Processing

Signal processing is a discipline of chemometrics that is concerned with manipulation of analytical data to make the information contained in the data more accessible.

Theoretical studies of the Fourier transform of voltammetric peaks, waves, and reversible LSV curves have been undertaken by Engholm [L50,L51]. Simons et al. [L52] employed Legendre polynomials for data reduction and noise filtering of amperometric signals. Four signal processing techniques: moving average smoothing, polynomial smoothing, rectangular low-pass filtering and exponential low-pass filtering were compared for use in potentiometric stripping analysis. Rectangular low-pass filtering was the most effective technique in enhancing the resolution of overlapping peaks [L53]. Stripping voltammetry data were subjected to signal processing such as background subtraction, ensemble averaging, digital filtering in the time and frequency domains, multiple scanning, and deconvolution [L54]. Signal processing methods: finite impulse response (FIR) and infinite impulse response (IIR) filters were employed for signal-to-noise ratio enhancement [L55]. The moving median filter was applied to potentiometric data. It removed the outliers without significant distortion of the signal while enhancing the signal-to-noise ratio [L56]. Zhou and Mo [L57] applied B-spline wavelet multifrequency channel decomposition for signal processing in the LSV. Zheng and Mo [L58] used B-spline wavelet coupled with Riemann-Liouville transform for signal processing in the staircase voltammetry. Chow et al. [L59] employed Fourier techniques for signal filtering of potentiometric stripping analysis data.

Expert Systems

Expert systems are a relatively large area of application of chemometric techniques in electrochemistry. An expert system is a method of classification which is a simple hierarchy of user-defined rules that are used to evaluate the data. An expert system translates a heuristic method into a decision tree that can be implemented to automate the analysis of data for a particular problem.

Palys et al. [L60-L63] applied knowledge-based system to the voltammetric elucidation of electrode reaction mechanism. The expert system designs experiments, controls the voltammetric or coulometric run, and collects data for each of the experiments used in the automated mechanism elucidation. Esteban and co-workers [L64-L69] developed an expert system for voltammetric determination of trace metals, which guides the user on choice of sample treatment and the best choice of voltammetric procedure. Provision is made for identification and resolution of overlapping peaks and quantification by means of the multiple standard addition method with statistical validation test. Garcia-Armada et al. [L70] developed a knowledge-based system for DPP. A database of information about possible constituents of the system to be studied can be processed to facilitate the best approach for simultaneous multielement analysis with maximum efficiency, interpret the resulting data, and identify the constituents of the sample.

SUMMARY OF THE INVENTION

The present invention relates to application of numerous chemometric techniques of design of experiment (DOE), modeling power, outlier detection, regression and calibration transfer for analysis of voltammetric responses obtained from various plating bathes. A novel parameter obtained by multiplying modeling power by squared least-squares regression coefficient proves to be a useful tool for determining the optimal part of a voltammogram taken for calibration calculations. Several methods were demonstrated for outlier detection within the training set to be applied prior regression calculation. The techniques for determining the optimal number of factors for regression calculation were presented. These techniques, while iteratively coupled with numerous discussed methods of outlier detection within the training set by regression calculation, can produce an outlier free training set to be used for final calibration calculations.

It has been demonstrated that multivariate regression methods can create a robust calibration model based on data that are virtually useless for univariate regression methods. It has been discovered that by combining into one data file data obtained using different techniques one may create a more accurate calibration model than that calculated for any single technique. The novel method is based on "gluing" parts of different voltammograms (but obtained for the same solution) prior decomposition and multivariate regression calculation. Powerful chemometric regression techniques provide robust, multivariate calibration that can be reliably transferred from the primary instrument to secondary instruments. Data sets passing outlier detection tests are being used for regression calculations. The information obtained about the concentration of deliberately added bath constituents can be used to maintain the desired constituent concentrations within limits in order to ensure optimal plating bath performance.

BRIEF DESCRIPTION OF THE DRAWINGS

FIG. 1 shows an example of a cyclic DC voltammogram scan dq21b26, ch2 for CUBATH® ViaForm™ (Enthone) copper plating bath.

FIG. 2 shows the squared correlation coefficients (Equation 7), $r^2$, for self-predicted, autoscaled tin concentrations obtained via least squares regression for each point of the voltammogram, variable j, (scan dq21x10, channel 2). The modeling power (Equation 11), R, calculated for same data.

FIG. 3a shows PRESS (Equation 25) calculated for various numbers of factors for self-predicted by PCR and PLS-1 brightener concentrations (scan dq21cu, channel 2, range 670-765).

FIG. 3b shows PRESS (Equation 25) calculated for various numbers of factors for self-predicted by PCR and PLS-1 carrier concentrations (scan dq21s4, ch 5, range 440-470).

FIG. 4a shows PRESS (Equation 25) calculated for various numbers of factors for cross-validated by PCR and PLS-1 brightener concentrations (scan dq21cu, channel 2, range 670-765).

FIG. 4b shows PRESS (Equation 25) calculated for various numbers of factors for cross-validated by PCR and PLS-1 carrier concentrations (scan dq21s4, ch 5, range 440-470).

FIG. 5 shows FPRESS (Equation 28) calculated for various numbers of factors for cross-validated brightener concentrations (scan dq21cu, channel 2, range 670-765) and carrier concentrations (scan dq21s4, ch 5, range 440-470).

FIG. 6a shows Exner $\Psi$ function (Equation 29) calculated for the same concentration data as that of FIG. 4a.

FIG. 6b shows Exner $\Psi$ function (Equation 29) calculated for the same concentration data as that of FIG. 4b.

FIG. 7 shows a plot of leverages versus externally Studentized concentration residuals for brightener (scan dq21ba2, channel 5, range 300-860, 4 factors)

FIG. 8 shows an example cyclic AC (X first harmonic) voltammogram scan dq21b26, ch3 for PC75 plating bath.

FIG. 9 shows actual (diamond) and cross validated by PCR (square) and by PLS-1 (triangle) acid concentration values for PC75 plating bath calibration; scan dq21b26, ch 3, range 4000-4800, 3 factors.

FIG. 10 shows the squared correlation coefficients (Equation 36), $(r^0)^2$, for self-predicted brightener concentrations. PC75 plating bath calibration obtained via least squares regression for part of the scan dq21ba2, channel 3, range 401-701 (first 301 points) glued with scan dq21ba2, channel 4, range (301-601) (last 301 points).

FIG. 11a shows prediction of acid concentration on the secondary instrument calculated employing regression equation from the primary instrument without any standardization (scan dq21b26, channel 3, 3600-4350, 4 factors).

FIG. 11b shows prediction of acid concentration on the secondary instrument calculated employing regression equation from the primary instrument standardized with DS (scan dq21b26, channel 3, 3600-4350, 4 factors).

FIG. 11c same as FIG. 11b but standardized with DSB.
FIG. 11d same as FIG. 11b but standardized with PDS.
FIG. 11e same as FIG. 11b but standardized with PDSB.
FIG. 11f same as FIG. 11b but standardized with DSS.
FIG. 11g same as FIG. 11b but standardized with DSBS.

DETAILED DESCRIPTION OF THE INVENTION

In accordance with the present invention, apparatus and a method for voltammetric analysis of the plating bath are provided. Analysis includes preliminary examination of the voltammograms for any disturbances in the bath performance and following quantitative determination of concentrations of all deliberately added bath components.

DC-AC Voltammetric techniques have been used for monitoring concentrations of bath constituents before, however the analysis of the voltammograms has been based on the single point usually corresponding to the peak current. This type of analysis is much less accurate and less reliable than chemometric analysis applying PCR or PLS methods which are used in the method described here. Several methods for qualifying the voltammograms prior to using them for prediction calculations of constituents' concentration are presented. These methods are able to detect changes in the shapes of voltammograms reflecting either changes in the bath composition (due to, for instance, contamination or concentrations of constituents being out of calibration range) or conditions under which the bath is running (for instance, a different temperature). All these reasons may impede the performance of the plating bath and therefore should be detected as soon as possible to enable the operator to stop plating and correct them before running further plating of, for instance, expensive materials like silicone wafers for the electronic industry.

The method of the present invention involves the steps of applying a changing in time potential to a working electrode in contact with the plating bath solution, and measuring the response signal. The characteristics of the response signal vary in accordance with the concentrations of constituents within the solution, and thereby provide an accurate real-time indication of concentrations of constituents.

In accordance with a preferred embodiment of the present invention, an AC signal superimposed on a DC sweep signal is applied to a working electrode which has been pretreated by a DC potential and is in contact with the plating bath solution. The DC sweep signal is varied at a selected sweep rate over a selected voltage range. An AC response current signal is thereby produced which includes peaks indicative of the concentration levels of constituents within the plating bath. The method establishes a set of optimal electrochemical parameters for an exemplary plating bath and its respective constituents.

As a feature of the present invention, the method eliminates the delay, expense and complexity typically associated with analysis methods requiring wet chemical analysis. Specialized chemical equipment and chemical analysis personnel are no longer required. The measurement results are available in real time, which facilitates continuous and efficient control of plating bath chemistry.

The above-discussed features and attendant advantages of the present invention will become better understood by reference to the detailed description of the preferred embodiment and the accompanying drawings.

Unless otherwise stated, computations were done using the Matlab Ver. 6.0 environment (The Math Works, Inc., Natick, Mass.) with the PLS_Toolbox Ver. 2.1.1 (Eigenvector Research, Inc., Manson, Wash.).

Experiment Design and Data Description

The plating bath consists of several components, both inorganic and organic, whose concentrations should be maintained within ranges recommended by the bath manufacturer in order to assure its satisfactory plating performance. The calibration of the probe for analyzing the plating bath should provide maximum information about the bath behavior for possibly many concentration combinations within specified ranges.

In order to assure possibly uniform distribution of concentration combinations within calibration ranges it was decided to apply linear orthogonal array for the experiment design. The chosen linear orthogonal array consists of 25 rows (which correspond to solutions of the training set) distributing concentrations of 5 or 6 bath components on 5 different levels. The example of linear orthogonal array designed for six-component Enthone CUBATH® ViaForm™ bath is shown in Table 1.

TABLE 1

Composition of calibration solutions for copper plating bath calculated as 5-level-6-component-25-row linear orthogonal array

| Solution # | Copper g/L | Acid g/L | Chloride ppm | Accelerator mL/L | Leveler mL/L | Suppressor mL/L |
|---|---|---|---|---|---|---|
| 1 | 14 | 140 | 20 | 1 | 0.5 | 5 |
| 2 | 14 | 155 | 33.75 | 1.6 | 1.1 | 6.3 |
| 3 | 14 | 170 | 47.5 | 2.3 | 1.75 | 7.5 |
| 4 | 14 | 185 | 61.25 | 2.9 | 2.4 | 8.8 |
| 5 | 14 | 200 | 75 | 3.5 | 3 | 10 |
| 6 | 15.5 | 140 | 33.75 | 2.9 | 3 | 7.5 |
| 7 | 15.5 | 155 | 47.5 | 3.5 | 0.5 | 8.8 |
| 8 | 15.5 | 170 | 61.25 | 1 | 1.1 | 10 |
| 9 | 15.5 | 185 | 75 | 1.6 | 1.75 | 5 |
| 10 | 15.5 | 200 | 20 | 2.3 | 2.4 | 6.3 |
| 11 | 17 | 140 | 47.5 | 1.6 | 2.4 | 10 |
| 12 | 17 | 155 | 61.25 | 2.3 | 3 | 5 |
| 13 | 17 | 170 | 75 | 2.9 | 0.5 | 6.3 |
| 14 | 17 | 185 | 20 | 3.5 | 1.1 | 7.5 |
| 15 | 17 | 200 | 33.75 | 1 | 1.75 | 8.8 |
| 16 | 18.5 | 140 | 61.25 | 3.5 | 1.75 | 6.3 |
| 17 | 18.5 | 155 | 75 | 1 | 2.4 | 7.5 |
| 18 | 18.5 | 170 | 20 | 1.6 | 3 | 8.8 |
| 19 | 18.5 | 185 | 33.75 | 2.3 | 0.5 | 10 |
| 20 | 18.5 | 200 | 47.5 | 2.9 | 1.1 | 5 |
| 21 | 20 | 140 | 75 | 2.3 | 1.1 | 8.8 |
| 22 | 20 | 155 | 20 | 2.9 | 1.75 | 10 |
| 23 | 20 | 170 | 33.75 | 3.5 | 2.4 | 5 |
| 24 | 20 | 185 | 47.5 | 1 | 3 | 6.3 |
| 25 | 20 | 200 | 61.25 | 1.6 | 0.5 | 7.5 |

The typical concentration ranges for copper, acid, chloride, accelerator, leveler and suppressor are 14-20 g/L, 140-200 g/L, 20-75 ppm, 1.0-3.5 mL/L, 0.5-3.0 mL/L and 5-10 mL/L, respectively. Prior to the calibration 25 solutions were prepared according to the concentration values in Table 1. Each of these solutions was electroanalyzed twice by recording a set of voltammograms.

The data of the training set consists of independent variables, voltammograms, and dependent variables, concentrations corresponding to the voltammograms. The number of independent variables, which corresponds to the chosen number of points of the voltammogram taken for the analysis, equals n. The number of dependent variables equals unity in the cases discussed below. The number of samples in the training set is m.

The original data consist of a matrix of independent variables, $X^O(m,n)$, and a vector of dependent variables, $c^O(m)$. The upper index "O" denotes original (means not transformed). In the example discussed in Table 1, m equals 50 (duplicate runs for 25 solutions).

According to the formalism employed herein, a bolded capital letter denotes a matrix. Some matrices are described by two bolded letters, the first of them is capital. A bolded small case letter(s) denotes a vector. The superscript "T" and the subscript "−1" denote a transposed matrix/vector and an inverse matrix, respectively. The subscript "u" denotes an unknown sample(s).

Data Preprocessing

Preprocessing refers to the transformation of the original data in order to enhance the information representation. After the transformation, a variable is referred to as a feature to distinguish it from the original variable.

The preprocessing method throughout these examples is autoscaling to unit variance [1,2], which refers to mean centering followed by dividing by the standard deviation, $s_j$, on a variable by variable basis:

$$x_{i,j} = \frac{x_{i,j}^O - x_j^\mu}{s_j} \quad (1)$$

where $$X_j^\mu = \frac{\sum_{i=1}^{m} X_{i,j}^O}{m} \quad (2)$$

and $$s_j = \sqrt{\frac{1}{m-1}\sum_{i=1}^{m}(X_{i,j}^O - X_j^\mu)^2} \quad (3)$$

Application of autoscaling transforms original variables $X^O$ and $c^O$ into features X and c, respectively.

Another method of data preprocessing occasionally applied is mean centering described by the following equation:

$$\bar{x}_{i,j} = x_{i,j}^O - x_j^\mu \quad (4)$$

If not otherwise stated, all features, both dependent (c) and independent (X), of the calculations presented below are assumed to be autoscaled to unit variance. Independent variables for prediction are transformed prior the calculations using scaling parameters of the training set. Predicted concentrations (dependent variables) are obtained via retransformation of predicted independent features using scaling parameters of the training set.

Traditional Methods of Calibration Calculation

Traditional methods of calibration calculation are based on univariate regression. Characteristic points to be regressed against concentrations in voltammetry are usually peak currents or peak charges (calculated by integration of peaks in time domain). FIG. 1 shows an example of a cyclic voltammogram recorded for CUBATH® ViaForm™ (Enthone) damascene copper plating bath. The first diffusion-controlled peak (range 1500-2000) corresponds to the copper ion reduction process. As potential reaches more negative values, the hydrogen ion reduction process (leading to the gaseous hydrogen evolution) starts to interfere with the copper ion reduction. The direction of potential change is reversed at point 2900 of the voltammogram. Starting from point 4355, one can observe the copper oxidation peak. In the CVS method this oxidation peak is considered to be correlated with the accelerator concentration in the plating bath. Least squares regression was applied in an attempt to correlate both oxidation peak height and peak surface (obtained via peak current integration) with the concentrations of all components present in the CUBATH® ViaForm™ plating bath.

The data for calibration was obtained by running twice each of 25 solutions of composition corresponding to that in the Table 1. Both independent and dependent variables were autoscaled prior regression calculation.

TABLE 2

Squared correlation coefficients for self prediction for concentrations of components of copper plating bath regressed by least-squares against integrated oxidation peak (columns 1, 3) and oxidation peak height (columns 2, 4), scan dq21b26, ch 2, range 4355-5150

| | Squared correlation coefficient ($r^2$) | | | |
|---|---|---|---|---|
| | 1 | 2 | 3 | 4 |
| Component | Full calibration integrated peak | Full calibration peak height | Limited calibration integrated peak | Limited calibration peak height |
| Copper | 0.807 | 0.653 | | |
| Acid | 0.0213 | 0.0881 | | |
| chloride | 0.109 | 0.169 | | |
| accelerator | 0.0404 | 0.0639 | 0.885 | 0.865 |
| leveler | 2.81E−04 | 7.60E−04 | 0.0212 | 0.0141 |
| suppressor | 5.28E−05 | 2.80E−03 | 0.0244 | 0.1059 |

The squared regression coefficients of self prediction are presented in Table 2, columns 1 and 2. One can notice that only copper concentration can be somehow (although not satisfactorily according to standards discussed further) correlated with peak height and peak surface. In order to find a CVS correlation between accelerator concentration and copper oxidation peak height/surface a limited calibration was conducted varying the concentrations of organic additives only. The composition of 9 solutions used for the limited calibration matrix is presented in Table 3.

TABLE 3

Composition of solutions for limited calibration (organic additives concentrations varied only) for copper plating bath calculated as 3-level-3-component-8-row linear orthogonal array plus the nominal solution (ninth row)

| Solution # | Copper g/l | Acid g/l | Chloride ppm | Accelerator ml/l | Leveler ml/l | Suppressor ml/l |
|---|---|---|---|---|---|---|
| 1 | 17.5 | 175 | 50 | 1 | 0.5 | 6 |
| 2 | 17.5 | 175 | 50 | 2 | 1.5 | 5 |
| 3 | 17.5 | 175 | 50 | 3 | 2.5 | 5 |
| 4 | 17.5 | 175 | 50 | 1 | 1.5 | 7.5 |
| 5 | 17.5 | 175 | 50 | 2 | 2.5 | 7.5 |
| 6 | 17.5 | 175 | 50 | 3 | 0.5 | 7.5 |
| 7 | 17.5 | 175 | 50 | 1 | 2.5 | 10 |
| 8 | 17.5 | 175 | 50 | 2 | 0.5 | 10 |
| 9 | 17.5 | 175 | 50 | 3 | 1.5 | 10 |

Concentrations of copper, acid and chloride were kept constant in all solutions and corresponding to the nominal values. The composition of the first eight solutions was calculated as a linear orthogonal array with two levels and three components (accelerator, leveler and suppressor). The ninth solution contains all components on their nominal level. The squared regression coefficients of self prediction are presented in Table 2, columns 3 and 4. One can observe a correlation between accelerator concentration and oxidation peak height/surface. However, even in these conditions the value of squared correlation coefficient is lower than that obtained by much more sophisticated chemometric regression techniques. Based on the analysis of results presented above, one can conclude that it is impossible to apply any approach analogous to CVS for on-line accelerator analysis in the plating bath due to the influence of the variable concentrations of inorganic additives. The accelerator is the fastest depleting component and the constant monitoring of its concentration is essential for proper maintenance of the plating bath.

Determination of the Calibration Range

In order to determine what part of the chosen voltammogram is the most promising to be used for calibration of any given component, two independent procedures should be conducted for each j-th point of DC/AC voltammogram:
  correlation calculation based on the least squares regression,
  SIMCA (Simple Modeling of Class Analogy) based calculation of modeling power [1].

The first method provides information on what range of the voltammogram shows the greatest correlation with the concentration of the component to be calibrated. It also determines the range where AC or DC current responses depend only on changes of concentration of the component of interest. Therefore each component requires its own specific range to be found. The other method gives information about signal to noise ratio for each point within the chosen range.

The optimal range to be chosen for calibration of a given component should have a good correlation, be possibly independent from concentration changes of constituents other than calibrated one, and have a high signal to noise ratio.

The algorithm for the correlation calculation based on the least squares regression is as follows:
  Both, independent and dependent variables are autoscaled.
  Regression is calculated for each point of the voltammogram. For j-th point of the scaled voltammogram (called also feature j) one can write the following regression equation:

$$c = x_j b_j \tag{5}$$

where regression coefficients is calculated via equation:

$$b_j = \frac{\sum_{i=1}^{m} x_{i,j} c_i}{\sum_{i=1}^{m} x_{i,j}^2} \tag{6}$$

Based on the regression coefficients, self-prediction is calculated for each point of the scaled voltammogram.

The squared correlation coefficients, $r^2$, are calculated for each j-th point of the scaled voltammogram:

$$r_j^2 = \frac{\left\{\sum_{i=1}^{m} c_i \hat{c}_{i,j} - \left(\sum_{i=1}^{m} c_i \sum_{i=1}^{m} \hat{c}_{i,j}\right)/m\right\}^2}{\left\{\sum_{i=1}^{m} c_i^2 - \left(\sum_{i=1}^{m} c_i\right)^2/m\right\}\left\{\sum_{i=1}^{m} \hat{c}_{i,j}^2 - \left(\sum_{i=1}^{m} \hat{c}_{i,j}\right)^2/m\right\}} \quad (7)$$

where $\hat{c}$ is the predicted scaled concentration.

The range corresponding to high values of $r^2$ (possibly close to unity) is picked up as a calibration range containing m points.

The SIMCA-based procedure for calculating the modeling power of the j-th point of scaled voltammogram (feature j) is as follows:

The autoscaled training set matrix X(m,n) is decomposed by PCA to principal components, S(m,a), and eigenvectors, V(n,a). The number of factors, a, is determined by cross validation (in the examples discussed later in the text the optimal number of factors usually equals 3 or 4).

The matrix of residuals for the training set is calculated from the expression:

$$E = X - SV^T \quad (8)$$

For each j-th point of the scaled voltammogram the residual variance of feature j, $rv_j^2$ (error), is computed from the following equation:

$$rv_j^2(\text{error}) = \sum_{i=1}^{m} \frac{e_{i,j}^2}{(m-a-1)} \quad (9)$$

where e is the element of the matrix E.

For each j-th point of the scaled voltammogram the meaningful variance in feature j, $rv_j^2(x)$, is given by:

$$rv_j^2(x) = \sum_{i=1}^{m} \frac{x_{i,j}^2}{(m-1)} \quad (10)$$

The modeling power of feature j, $R_j$, is defined to be:

$$R_j = 1 - \frac{rv_j(\text{error})}{rv_j(x)} \quad (11)$$

As $R_j$ approaches unity, the feature is highly relevant; conversely, at it approaches zero, the feature approaches zero utility in the model.

FIG. 2 presents an application example of both the squared correlation coefficient, $r_j^2$, (obtained via least squares regression) and the modeling power, $R_j$, as a criteria for determining the optimal calibration range of voltammogram. FIG. 2 is based on the analysis of CV voltammograms of tin redox electrode reactions in the tin/lead plating bath. Squared correlation coefficients, $r_j^2$, correlate the electroanalytical response with actual tin concentration in training set solutions for each, j-th point of the voltammogram. One can notice that neither $r_j^2$, nor $R_j$ is a sufficient criterion to determine whether a given feature j is an optimal one to be included into the calibration range. Only features j for which both $r_j^2$, and $R_j$ values are relatively high can be taken into calibration (like range 55-210 in FIG. 2). Therefore the analysis of combined parameter $R_j r_j^2$ is helpful for determining the optimal calibration range as demonstrated in FIG. 2. It should be mentioned that the analysis of the $R_j r_j^2$ parameter provides only an estimated calibration range. The optimal calibration range should finally be determined via cross validation methods by also checking empirically ranges slightly wider than that suggested by $R_j r_j^2$. However, the optimal range should contain, in most cases, the whole range corresponding to significant values of $R_j r_j^2$ parameter. It should be mentioned that the calibration range might be extended to include only points still having high modeling power value.

Outlier Detection within the Training Set Prior to Regression Calculation

The next step of the analysis is the examination of the training set in order to determine and eliminate possible outliers prior to calculation of regression. The Principal Component Analysis (PCA) [3,4] method is applied to decompose matrix X(m,n) into matrices being outer products of vectors called scores (S(m,a)) and loadings (V(n,a)). Four different methods were used to decompose the data matrix X. The first two methods, nonlinear iterative partial least squares (NIPALS) [2, 5] and successive average orthogonalization (SAO) [6], were pair-by-pair methods while Jacobi transformation [7,8] methods calculated all the principal components at once using the variance-covariance matrix. The results of all methods were practically identical. The PCA calculations were done in MS Visual Basic (VB) and were compared to results obtained with Matlab Singular Value Decomposition technique to reach full agreement. All computations discussed below connected with outlier detection were done in VB and in Matlab mostly in order to verify their correctness. In the case of VB programs the NIPALS method was chosen as optimal (based mostly on the time factor) for X matrix decomposition.

In order to determine outliers in the training set the Mahalanobis distance (MD) coupled with PCA (MD/PCA) was applied. One of the main reasons the Mahalanobis distance was chosen is that it is very sensitive to intervariable changes in the training set data. In addition, the distance is measured in terms of the standard deviation from the mean of the training samples. The difference between the classical Mahalanobis distance and Mahalanobis distance coupled with PCA methods is that in the latter S replaces X from the former in the analysis. Prior to the calculation of Mahalanobis distance it is necessary to calculate the Mahalanobis matrix (M) based on the scores of the whole training set:

$$M = S^T S/(m-1) \quad (12)$$

The square of the Mahalanobis distance corresponding to i-th sample in the training set is calculated from the following equation:

$$D_i^2 = s_i M^{-1} s_i^T \quad (13)$$

Samples having significantly larger values of D are eliminated from the training set as outliers. The remaining data is used to calculate the calibration.

A more reliable approach for elimination of outliers from the training set is the Mahalanobis distance based on the cross validation. In this method one checks the part of the training set based on the criterion of best predictive ability, as opposed to best fit (like the self prediction method presented above). The iterative procedure for cross validation using Mahahalobis distance method coupled with PCA is presented below:

Set the value of index k=1.

Extract k-th vector $x_k^O(n)$ from data matrix $X^O(m,n)$. The remaining matrix is called $X_k^O(m-1, n)$ and plays a role of the training set matrix in the k-th step.

Matrix $X_k^O$ is to be autoscaled to unit variance to obtain $X_k$.

The vector $x_k^O$ is scaled using scaling parameters of matrix $X_k^O$ to obtain $x_k$.

The matrix $X_k$ is decomposed for scores $S_k(m-1,a)$ and eigenvectors $V_k(n,a)$ using number of factors of a.

The Mahalanobis matrix is calculated by applying the following dependence:

$$M_k = S_k^T S_k/(m-2) \quad (14)$$

Scores are calculated for the vector $x_k$ using the equation:

$$s_k = x_k V_k \quad (15)$$

The square of the Mahalanobis distance corresponding to k-th sample is calculated from the following equation:

$$D_k^2 = s_k M_k^{-1} s_k^T \quad (16)$$

If k is less than m then increment k by one and return to the second step of this procedure.

Another method based on the Mahalanobis distance by principal component analysis employs not only scores but also residuals. The algorithm for the method called Mahalanobis distance by principal component analysis with residuals (MD/PCA/IR) [9] for cross-validation is presented below:

Set the value of index k=1.

Extract k-th vector $x_k^O(n)$ from data matrix $X^O(m,n)$. The remaining matrix is called $X_k^O(m-1, n)$ and plays a role of the training set matrix in the k-th step.

Matrix $X_k^O$ is to be autoscaled to unit variance to obtain $X_k$.

The vector $x_k^O$ is scaled using scaling parameters of matrix $X_k^O$ to obtain $x_k$.

The matrix $X_k$ is decomposed for scores $S_k(m-1,a)$ and eigenvectors $V_k(n,a)$ using number of factors of a.

The matrix of residuals for k-th training set matrix, $E_k(m-1,n)$, is calculated via following equation:

$$E_k = X_k - S_k V_k^T \quad (17)$$

The column vector of the squared sums of residuals, called also Q residuals, for the k-th training set, $rs_k(m-1)$, is computed employing following dependence:

$$rs_k = \sum_{j=1}^{n} (e_{i,j})^2 \quad (18)$$

where $e_{i,j}$ is the element of the matrix $E_k$.

The column vector $rs_k$ is being added as the a+1$^{st}$ column to the matrix of scores $S_k(m-1,a)$. This creates a residual augmented scores matrix, $T_k(m-1,a+1)$.

The Mahalanobis matrix is calculated from the residual augmented scores by applying the following dependence:

$$Mr_k = T_k^T T_k/(m-2) \quad (19)$$

Scores, $s_k$, for the vector $x_k$ are calculated using Equation 15.

The predicted row vector of residuals, $ep_k(n)$, for vector $x_k$ is calculated using the following equation:

$$ep_k = x_k(I - V_k V_k^T) \quad (20)$$

where I(n,n) is an identity matrix. The identity matrix is always square and contains ones on the diagonal and zeros everywhere else.

The predicted residual sum of squares, $rp_k$, for $x_k$ vector is computed employing the expression:

$$rp_k = \sum_{j=1}^{n} ep_{k,j}^2 \quad (21)$$

The scalar $rp_k$ is being appended as the a+1$^{st}$ value to the row vector $s_k(a)$. This creates a residual augmented scores vector, $t_k(a+1)$.

The value of square Mahalanobis distance is predicted for the unknown sample by applying the following expression:

$$Dr_k^2 = t_k Mr_k^{-1} t_k^T \quad (22)$$

If index k is less than n then increment k by one and return to the second step of this procedure.

TABLE 4

MD/PCA self prediction and cross-validation, and MD/PCA/R cross-validation calculated for s4 scan, range 200-250, and channels 4 and 5. Columns 1, 2, 3, 7, 8 and 9 are computed for the whole training set (prior removal of outliers). Columns 4, 5, 6, 10, 11 and 12 are calculated for the training set after removal of outliers.

| # | 1 selfpred | 2 X val | 3 XV Res | 4 selfpred | 5 X val | 6 XV Res | 7 selfpred | 8 X val | 9 XV Res | 10 selfpred | 11 X val | 12 XV Res |
|---|---|---|---|---|---|---|---|---|---|---|---|---|
| 1 | 3.13 | 3.53 | 3.83 | 3.29 | 3.77 | 3.86 | 2.98 | 3.33 | 3.34 | 3.27 | 3.75 | 3.81 |
| 2 | 2.68 | 2.93 | 2.97 | 2.70 | 2.97 | 3.03 | 2.90 | 3.22 | 3.39 | 2.89 | 3.22 | 3.23 |
| 3 | 2.44 | 2.62 | 2.66 | 2.49 | 2.70 | 2.75 | 2.94 | 3.24 | 3.46 | 3.13 | 3.54 | 3.54 |
| 4 | 3.30 | 3.77 | 3.85 | 3.33 | 3.84 | 3.94 | 2.80 | 3.03 | 3.67 | 3.03 | 3.39 | 4.03 |
| 5 | 3.33 | 3.82 | 3.89 | 3.38 | 3.91 | 4.17 | 2.59 | 2.69 | 6.56 | 3.09 | 3.48 | 5.52 |
| 6 | 2.87 | 3.17 | 3.37 | 2.86 | 3.17 | 3.49 | 2.22 | 2.33 | 3.41 | 2.86 | 3.17 | 3.24 |
| 7 | 2.40 | 2.58 | 3.50 | 2.72 | 2.98 | 3.16 | 2.24 | 2.39 | 2.43 | 2.75 | 3.02 | 3.02 |
| 8 | 2.49 | 2.69 | 2.71 | 2.55 | 2.77 | 2.80 | 2.47 | 2.66 | 2.77 | 2.48 | 2.68 | 3.40 |
| 9 | 2.79 | 3.08 | 3.37 | 2.77 | 3.05 | 3.74 | 2.65 | 2.88 | 2.93 | 2.64 | 2.89 | 3.75 |
| 10 | 2.87 | 3.18 | 3.20 | 2.84 | 3.15 | 3.18 | 2.74 | 3.00 | 3.02 | 2.93 | 3.27 | 3.27 |

TABLE 4-continued

MD/PCA self prediction and cross-validation, and MD/PCA/R cross-validation calculated for s4 scan, range 200-250, and channels 4 and 5. Columns 1, 2, 3, 7, 8 and 9 are computed for the whole training set (prior removal of outliers). Columns 4, 5, 6, 10, 11 and 12 are calculated for the training set after removal of outliers.

| # | 1 selfpred | 2 X val | 3 XV Res | 4 selfpred | 5 X val | 6 XV Res | 7 selfpred | 8 X val | 9 XV Res | 10 selfpred | 11 X val | 12 XV Res |
|---|---|---|---|---|---|---|---|---|---|---|---|---|
| 11 | 2.96 | 3.29 | 3.31 | 3.02 | 3.39 | 3.60 | 2.68 | 2.92 | 3.07 | 3.21 | 3.65 | 4.22 |
| 12 | 3.08 | 3.46 | 3.57 | 3.10 | 3.50 | 3.60 | 2.80 | 3.08 | 4.03 | 3.29 | 3.78 | 3.80 |
| 13 | 1.08 | 1.11 | 1.68 | 1.57 | 1.63 | 1.66 | 1.94 | 2.01 | 2.67 | 2.00 | 2.11 | 2.29 |
| 14 | 0.93 | 0.95 | 4.93 | 1.83 | 1.90 | 3.61 | 2.25 | 2.38 | 2.81 | 2.26 | 2.41 | 2.65 |
| 15 | 0.85 | 0.87 | 2.77 | 1.71 | 1.77 | 2.11 | 2.17 | 2.29 | 2.58 | 2.16 | 2.30 | 2.37 |
| 16 | 0.89 | 0.90 | 1.07 | 1.99 | 2.09 | 2.14 | 1.31 | 1.35 | 1.47 | 1.34 | 1.38 | 1.65 |
| 17 | 1.09 | 1.11 | 1.16 | 2.44 | 2.63 | 2.66 | 1.51 | 1.56 | 1.68 | 1.51 | 1.56 | 2.66 |
| 18 | 1.80 | 1.87 | 3.81 | 1.97 | 2.06 | 3.78 | 1.66 | 1.71 | 2.07 | 2.00 | 2.11 | 2.20 |
| 19 | 1.32 | 1.36 | 1.36 | 1.30 | 1.34 | 1.35 | 0.84 | 0.85 | 1.39 | 1.34 | 1.38 | 1.43 |
| 20 | 1.47 | 1.52 | 1.52 | 1.78 | 1.86 | 2.14 | 0.94 | 0.96 | 1.45 | 0.99 | 1.01 | 3.11 |
| 21 | 1.55 | 1.61 | 1.61 | 1.69 | 1.76 | 1.86 | 0.98 | 1.00 | 1.60 | 1.82 | 1.90 | 1.96 |
| 22 | 1.37 | 1.41 | 2.14 | 1.34 | 1.38 | 3.06 | 1.36 | 1.37 | 1.86 | 1.46 | 1.49 | 4.45 |
| 23 | 1.53 | 1.59 | 2.15 | 2.45 | 2.64 | 2.84 | 1.86 | 1.86 | 2.66 | 2.55 | 2.77 | 2.79 |
| 24 | 1.74 | 1.81 | 1.87 | 2.11 | 2.24 | 2.30 | 1.53 | 1.54 | 2.09 | 2.19 | 2.33 | 2.35 |
| 25 | 1.16 | 1.19 | 1.20 | 1.20 | 1.23 | 1.23 | 1.09 | 1.11 | 1.62 | 1.27 | 1.30 | 1.32 |
| 26 | 1.09 | 1.12 | 1.12 | 1.09 | 1.11 | 1.11 | 0.99 | 1.01 | 1.41 | 1.08 | 1.11 | 1.19 |
| 27 | 0.85 | 0.87 | 0.88 | 0.83 | 0.85 | 0.87 | 1.10 | 1.13 | 1.40 | 1.10 | 1.13 | 1.38 |
| 28 | 0.65 | 0.66 | 0.67 | 0.65 | 0.65 | 0.68 | 0.68 | 0.69 | 0.81 | 0.66 | 0.67 | 0.73 |
| 29 | 0.79 | 0.80 | 1.14 | 0.78 | 0.79 | 1.57 | 0.65 | 0.66 | 0.78 | 0.68 | 0.69 | 0.80 |
| 30 | 0.69 | 0.70 | 0.70 | 1.01 | 1.03 | 1.07 | 0.65 | 0.66 | 0.77 | 0.76 | 0.77 | 1.36 |
| 31 | 0.63 | 0.64 | 0.69 | 0.83 | 0.84 | 0.92 | 0.63 | 0.63 | 0.72 | 0.76 | 0.77 | 0.81 |
| 32 | 0.61 | 0.61 | 0.97 | 1.60 | 1.66 | 1.77 | 0.90 | 0.91 | 1.06 | 1.36 | 1.40 | 1.46 |
| 33 | 1.03 | 1.05 | 1.06 | 1.35 | 1.39 | 1.46 | 0.65 | 0.66 | 1.00 | 1.21 | 1.24 | 1.28 |
| 34 | 0.76 | 0.78 | 1.74 | 1.50 | 1.55 | 2.08 | 1.36 | 1.37 | 1.60 | 1.70 | 1.77 | 1.79 |
| 35 | 1.41 | 1.46 | 1.46 | 1.93 | 2.03 | 2.26 | 1.15 | 1.15 | 1.60 | 1.82 | 1.91 | 1.94 |
| 36 | 1.16 | 1.19 | 1.40 | 1.18 | 1.20 | 2.00 | 1.03 | 1.04 | 1.27 | 1.09 | 1.11 | 2.97 |
| 37 | 1.08 | 1.10 | 1.32 | 1.14 | 1.17 | 1.86 | 1.02 | 1.04 | 1.51 | 1.06 | 1.08 | 1.58 |
| 38 | 1.47 | 1.52 | 1.53 | 1.45 | 1.50 | 1.50 | 1.10 | 1.12 | 1.84 | 1.33 | 1.37 | 1.43 |
| 39 | 1.95 | 2.05 | 2.67 | 2.31 | 2.47 | 5.61 | 1.13 | 1.16 | 2.33 | 2.18 | 2.32 | 2.59 |
| 40 | 1.11 | 1.13 | 1.15 | 1.26 | 1.30 | 1.37 | 0.99 | 1.00 | 1.26 | 1.02 | 1.05 | 1.17 |
| 41 | 1.12 | 1.15 | 1.17 | 1.35 | 1.39 | 1.44 | 1.00 | 1.02 | 1.18 | 1.00 | 1.02 | 1.14 |
| 42 | 0.91 | 0.92 | 1.18 | 1.46 | 1.51 | 2.03 | 1.25 | 1.28 | 1.34 | 1.22 | 1.25 | 1.42 |
| 43 | 0.85 | 0.86 | 0.88 | 1.23 | 1.26 | 1.41 | 1.09 | 1.11 | 1.15 | 1.06 | 1.09 | 1.14 |
| 44 | 0.96 | 0.98 | 1.17 | 1.40 | 1.44 | 1.54 | 1.49 | 1.54 | 1.54 | 1.48 | 1.53 | 1.54 |
| 45 | 6.87 | 34.35 | 349.84 | | | | 6.92 | 40.89 | 5560.16 | | | |
| 46 | 1.66 | 1.72 | 2.63 | 2.00 | 2.11 | 2.73 | 2.30 | 2.44 | 2.47 | 2.38 | 2.56 | 2.56 |
| 47 | 1.17 | 1.20 | 1.21 | 1.25 | 1.28 | 1.31 | 1.73 | 1.80 | 1.85 | 1.82 | 1.90 | 1.91 |
| 48 | 1.37 | 1.41 | 1.49 | 1.78 | 1.86 | 1.95 | 1.97 | 2.06 | 2.09 | 1.98 | 2.08 | 2.09 |
| 49 | 0.94 | 0.96 | 0.97 | 10.94 | 0.96 | 0.98 | 0.90 | 0.92 | 1.09 | 1.06 | 1.09 | 1.11 |
| 50 | 1.27 | 1.31 | 1.49 | 2.03 | 2.14 | 2.49 | 0.94 | 0.96 | 1.39 | 1.57 | 1.62 | 2.02 |
| 51 | 0.91 | 0.93 | 1.16 | 0.89 | 0.90 | 1.39 | 0.86 | 0.88 | 1.14 | 0.85 | 0.87 | 1.60 |

MD/PCA self-prediction and cross-validation, and MD/PCA/R cross-validation calculated for two data sets are presented in Table 4. Both data sets were obtained for the same training set of solutions. However, they differ from each other in the manner by which some experimental parameters were obtained. As expected, MD/PCA/R values for cross-validation are slightly larger than that for cross-validation, which are larger than that for self-prediction (Table 4, column is 1,2,3 and 7,8,9). However, the sensitivity of outlier detection performance is definitely the largest for MD/PCA/R as demonstrated by the example of sample #45. After removing of the outliers from the training set, the self-prediction and cross-validation MD/PCA and MD/PCA/R were recalculated and presented in columns 4, 5, 6 and 10, 11, 12 respectively.

Another powerful method for outlier detection is called SIMCA [1]. In order to check whether the whole training set consists of one class (in other words, whether there are no outliers within the training set) cross validation can be applied. The algorithm for SIMCA cross validation is following:

Set the value of index k=1.

Extract k-th vector $x_k^O(n)$ from data matrix $X^O(m,n)$. The remaining matrix is called $X_k^O$ (m−1, n) and plays a role of the training set matrix in the k-th step.

Matrix $X_k^O$ is to be autoscaled to unit variance to obtain $X_k$.

The vector $x_k^O$ is scaled using scaling parameters of matrix $X_k^O$ to obtain $x_k$.

The matrix $X_k$ is decomposed for scores $S_k(m−1,a)$ and eigenvectors $V_k(n,a)$ using number of factors of a.

The matrix of residuals for k-th training set matrix, $E_k(m−1,n)$, is calculated via Equation 17.

The residual variance for the k-th training set $X_k$ is calculated from the equation:

$$rv_{0,k}^2 = \sum_{i=1}^{m-1} \sum_{j=1}^{n} \frac{e_{i,j}^2}{(m-a-2)(n-a)} \qquad (23)$$

The row vector of predicted residuals for vector $x_k$, $ep_k$, is calculated using Equation 20.

The predicted residual variance for vector $x_k$ normalized with respect to $rv_{0,k}^2$ is computed using the following expression:

$$rv_k^2 = \sum_{j=1}^{n} \frac{ep_{k,j}^2}{(n-a)rv_{0,k}^2} \qquad (24)$$

If index k is less than m then increment k by one and return to the second step of this procedure.

For the sake of comparison of performance between MD-based methods and SIMCA cross-validation the same experimental data from Table 4 was used for SIMCA calculations presented in Table 5.

TABLE 5

Predicted residual variances (Equation 24) normalized with respect to residual variance for training subsets (Equation 23) for s4 scan, range 200-250, and channels 4 and 5. Columns 1 and 2 are computed for the whole training set. Columns 3 and 4 are calculated for the training set after outlier removal.

| #  | 1     | 2      | 3    | 4    |
|----|-------|--------|------|------|
| 1  | 1.74  | 1.82   | 1.32 | 0.51 |
| 2  | 0.86  | 0.23   | 0.98 | 0.26 |
| 3  | 0.91  | 1.91   | 0.97 | 0.18 |
| 4  | 0.62  | 5.29   | 0.58 | 4.62 |
| 5  | 0.51  | 9.73   | 1.18 | 7.44 |
| 6  | 0.90  | 4.99   | 1.30 | 0.78 |
| 7  | 2.53  | 1.51   | 1.57 | 1.35 |
| 8  | 0.19  | 0.10   | 0.71 | 3.36 |
| 9  | 1.57  | 1.48   | 2.53 | 3.36 |
| 10 | 0.43  | 1.11   | 0.56 | 0.31 |
| 11 | 0.42  | 1.82   | 1.10 | 2.32 |
| 12 | 1.05  | 3.58   | 0.93 | 0.38 |
| 13 | 1.70  | 0.97   | 0.89 | 1.00 |
| 14 | 6.21  | 0.59   | 4.29 | 1.21 |
| 15 | 3.69  | 0.31   | 2.03 | 0.54 |
| 16 | 0.98  | 0.03   | 0.34 | 1.10 |
| 17 | 0.73  | 0.12   | 0.60 | 2.75 |
| 18 | 4.61  | 0.83   | 4.16 | 0.40 |
| 19 | 0.25  | 1.19   | 0.36 | 0.20 |
| 20 | 0.48  | 1.34   | 1.74 | 3.86 |
| 21 | 0.36  | 1.69   | 0.58 | 0.28 |
| 22 | 2.32  | 2.00   | 3.30 | 5.32 |
| 23 | 2.10  | 2.88   | 0.64 | 0.24 |
| 24 | 0.89  | 2.30   | 0.30 | 0.16 |
| 25 | 0.16  | 0.64   | 0.21 | 0.23 |
| 26 | 0.10  | 0.46   | 0.16 | 0.44 |
| 27 | 0.21  | 0.24   | 0.27 | 0.83 |
| 28 | 0.16  | 0.03   | 0.25 | 0.18 |
| 29 | 1.24  | 0.04   | 1.72 | 0.26 |
| 30 | 0.26  | 0.04   | 0.70 | 1.47 |
| 31 | 0.46  | 0.28   | 0.34 | 0.12 |
| 32 | 1.08  | 0.69   | 0.30 | 0.22 |
| 33 | 0.42  | 0.91   | 0.34 | 0.13 |
| 34 | 2.16  | 1.31   | 1.25 | 0.22 |
| 35 | 0.42  | 1.62   | 0.80 | 0.13 |
| 36 | 1.21  | 1.16   | 2.12 | 3.67 |
| 37 | 0.95  | 0.56   | 1.62 | 1.33 |
| 38 | 0.13  | 0.94   | 0.17 | 0.44 |
| 39 | 2.11  | 1.63   | 5.99 | 1.74 |
| 40 | 0.27  | 0.39   | 0.36 | 0.56 |
| 41 | 0.25  | 0.24   | 0.20 | 0.50 |
| 42 | 0.96  | 0.16   | 1.26 | 0.71 |
| 43 | 0.25  | 0.04   | 0.47 | 0.28 |
| 44 | 0.81  | 0.04   | 0.33 | 0.12 |
| 45 | 411.12| 7442.55|      |      |
| 46 | 2.42  | 0.43   | 1.63 | 0.36 |
| 47 | 0.13  | 0.35   | 0.21 | 0.21 |
| 48 | 0.57  | 0.30   | 0.29 | 0.26 |
| 49 | 0.26  | 0.23   | 0.35 | 0.22 |
| 50 | 0.97  | 0.56   | 2.21 | 1.71 |
| 51 | 0.93  | 0.24   | 1.31 | 1.53 |

Based on our experience, the percentage of outliers in the training set is not larger than 5% for systems, setups and voltammetric methods worked with. A relatively low number of outliers in the training set is connected with very stable conditions (including fully controlled composition of solutions for calibration) the calibration is performed in. Also the waveform of applied voltammograms are chosen to be as possibly reproducible and stable as possible.

A relatively low number of outliers in the training set allows us to assume that Mahalanobis distance and SIMCA methods are reliable in our conditions. The disadvantage of MD method, which fortunately was not encountered, is producing of inaccurate results if there are multiple outliers (usually several tens of percent of the training set) in the data. Methods for dealing with multiple outliers are: MCD (minimum covariance determinant) [10], RHM (resampling by half-means) [11] and (SHV (smallest half-volume) [11]. These methods require determining the maximal percentage of outliers in the training set. Based on this information the best training subset is selected and used for calibration. In that paper [11], the authors suggest removal of up to 50% of original training set. Such a treatment would lead, in our case, to the uncompensated loss of good calibration data containing mostly files corresponding to concentrations close to the lower and upper limits. This would narrow the concentration range of the training set and impede predicting the performance of the regression equation.

Determination of the Optimal Number of Factors for Calibration

One of the most effective methods that can be used to aid in determining the optimal number of factors for calibration is called PRESS (Prediction residual error sum of squares) [1,4,12]. This method is based on the calculation of concentration residuals for different numbers of factors. The self-predicted and/or cross-validated concentrations are obtained using both principal component regression (PCR) [12,13,14] and partial least-squares (PLS-1) [1,2,12,13,14,15] regression. Both regression methods are commonly used and their algorithms are described in the literature in great detail.

If the number of dependent features equals unity then the expression for PRESS is following:

$$\text{PRESS} = \sum_{i=1}^{m} (ec_i^O)^2 \qquad (25)$$

where $ec_i^O$ is the concentration residual of the i-th sample calculated for its original (not autoscaled) actual concentration and the retransformed (rescaled) self-predicted/cross validated concentration via the following dependence:

$$ec_i^O = c_i^O - \hat{c}_i^O \qquad (26)$$

where $\hat{c}_i^O$ denotes retransformed (resealed) concentration predicted via selfprediction/cross validation.

FIGS. 3a and 3b present the calculated values of self-predicted PRESS using PCR and PLS-1 for brightener and carrier, respectively. The self-predicted PRESS is the simplest and fastest method for testing a calibration model. The problem with this approach is that the model vectors are calculated from these same voltammograms. Therefore, all the vectors calculated exist in all the training voltammograms. This was not very problematic in the case of Mahalanobis distance calculations, but here the PRESS plot will continue to fall as new factors are added to the model and will never rise. It is possible to select the number of factors as the place where the plot starts to "flatten out". One can notice that plots in FIGS. 3a and 3b (for PCR) start to "flatten out" at a factor number of four. However, this is an inexact measure, and gives no indication of the true optimum number of factors for the model when predicting unknown samples. One can obtain much more reliable data while using cross-validation PRESS for all the samples in the training set. Each sample, in turn, is omitted from the training set and a model is calculated with the remaining samples. This model predicts the concentration for the omitted sample. The squared error between predicted and actual values is calculated to form a single PRESS value. The sample is then returned to the training set, the next sample is omitted, and the cycle repeated to calculate another PRESS value. The procedure is repeated until all the samples have been treated. The PRESS values are summed and this constitutes the PRESS value for the model. The values of PRESS calculated using cross validation PCR and PLS-1 for brightener and carrier are displayed in FIGS. 4a and 4b, respectively. In FIGS. 4a and 4b, one can notice that from 1 to 4 factors the prediction error (PRESS) decreases as each new factor is added to the model. This indicates that the model is underfit and there are not enough factors to account completely for the constituents of interest. On both FIGS. 4a and 4b the PRESS plots reach a minimum and start to ascend again (corresponding to number of factors of 4). At this point the model is beginning to add factors that contain uncorrelated noise which is not related to the constituents of interest. The factor number corresponding to the minimum value of PRESS indicates the optimal number of factors. Although cross-validation PRESS calculations are much more time consuming that self-prediction PRESS calculations the former are recommended for optimal factor number determination. In order to determine the number of factors corresponding to the local minimum of PRESS calculated for the smallest possible number of factors, the R ratio of successive prediction sum of squares is being employed [1,4]:

$$R(a) = \frac{\text{PRESS}(a+1)}{\text{PRESS}(a)} > 1 \qquad (27)$$

Starting with number of factors, a=1, if the R is less than one, then the increased factor space yields better predictions; hence the procedure is repeated with j=2, etc. until the ratio is greater than one, indicating that the added factor does not improve the predictions. R ratio calculated for the data of both FIGS. 4a and 4b indicates the optimal number of factors of a=4 for both regression methods, PCR and PLS-1.

The F statistic, based on PRESS [15], can also be used to aid in the comparison of the prediction abilities of the two different calibration methods, PCR and PLS-1. Let us define the F-ratio for two different calibration methods as:

$$F_{PRESS} = \frac{\text{PRESS}(PCR)}{\text{PRESS}(PLS)} \qquad (28)$$

To illustrate the performance of the $F_{PRESS}$ parameter, the data from FIGS. 4a and 4b were recalculated and presented in FIG. 5. For the optimal number of factors, a, one should expect similar performance of PCR and PLS-1, which means the $F_{PRESS}$ ratio should be close to unity. One can notice that in FIG. 5 $F_{PRESS}$ is closest to one for brightener for a=4, which confirms the conclusion based on R-ratio analysis. However, the data for carrier in FIG. 5 does not provide us a conclusive answer as the $F_{PRESS}$ ratio is close to unity both for a=3 and 4.

The other method that can be helpful for determining the optimal number of factors for calibration is based on the Exner psi ($\psi$) function [4,16,17] given by:

$$\psi(a) = \left( \frac{\sum_{i=1}^{m} \left( c_i^O - \hat{c}_i^O(a) \right)^2}{\sum_{i=1}^{m} \left( c_i^O - \frac{\sum_{i=1}^{m} \hat{c}_i^O(a)}{m} \right)^2} \times \frac{m}{m-a} \right)^{1/2} \qquad (29)$$

The values of the Exner $\psi$ function calculated for the same concentration data as used for PRESS calculation in FIGS. 4a and 4b are presented in FIGS. 6a and 6b, respectively. One can easily notice that the Exner $\psi$ function curves in FIGS. 6a and 6b are qualitatively analogous to those of PRESS in FIGS. 4a and 4b, respectively. In a manner similar to PRESS, the local minimum of the Exner $\psi$ function corresponding to the smallest possible number of components indicates the optimal number of factors. Additionally, the analysis of the absolute value of the Exner $\psi$ function provides information about the accuracy of the calibration model. A value of the Exner $\psi$ function equal to 1.0 is the upper limit of physical significance, because this means that one has not done any better than simply guessing that each point has the same value of the grand mean of the experimental data. Exner [17] proposed that 0.5 should be considered the largest acceptable $\psi$ value, because it means that the fit is twice as good as guessing the grand mean for each point.

Outlier Detection within the Training Set by Regression Calculation

Apart from the Mahalanobis distance and SIMCA methods described above there are other powerful tools for outlier detection: F-ratio method based on concentration residuals, $F^c$-ratio, and plot of Studentized concentration residuals versus leverages. However, in contrast to Mahalanobis distance and SIMCA methods, these employ regression calculations. When the optimum number of factors for the model has been determined, the concentration residuals are calculated using Equation 26. In the $F^c$-ratio method for cross-validation, the training sample square residual is expressed with respect to the rest of the training set by following equation [15]:

$$F_i^c = \frac{(m-1)(ec_i^O)^2}{\sum_{j \neq i} (ec_j^O)^2} \qquad (30)$$

Another useful tool for identifying outliers within the training set is a plot of the internally or externally Studentized concentration residuals versus the leverage value for each sample [18]. The leverage value gives a measure of how important an individual training sample is to the overall model. The Studentized residual give an indication of how well the sample's predicted concentration is in line with the leverage. Both, leverages and Studentized residuals can be calculated by means of self-prediction or cross-validation. The approach based on cross-validation has a higher resolution than that for self-prediction and therefore has our preference. The algorithm presented below calculates cross-validated leverages:

Set the value of index k=1.

Extract k-th vector $x_k^O(n)$ from data matrix $X^O(m,n)$. The remaining matrix is called $X_k^O(m-1,n)$ and plays a role of the training set matrix in the k-th step.

Matrix $X_k^O$ is to be autoscaled to unit variance to obtain $X_k$.

The vector $x_k^O$ is scaled using scaling parameters of matrix $X_k^O$ to obtain $x_k$.

The matrix $X_k$ is decomposed for scores $S_k(m-1,a)$ and eigenvectors $V_k(n,a)$ using number of factors of a.

Scores are calculated for the vector $x_k$ using Equation 15.

The vector $s_k$ is appended as the k-th row into the matrix, S, of scores predicted by cross validation.

If index k is less than m then k is incremented by one and returned to the second step of this procedure.

The matrix of scores, S, is being used to calculate the square "hat" matrix, H(m,m) according to the equation:

$$H = S(S^T S)^{-1} S^T \qquad (31)$$

The diagonal elements of the "hat" matrix, $h_{k,k}$, constitute leverages. The k-th leverage corresponds to k-th sample of the training set.

The procedure for internally and externally Studentized concentration residuals starts with the calculation of the column vector of concentration residuals, $ec^O$ (Equation 26). The predicted concentrations for residuals are calculated by PCR or PLS-1 cross-validation for the number of factors of a. The number of factors must be the same as that for the "hat" matrix. The internally Studentized residual for the k-th sample of the training set is computed employing following dependence [18]:

$$\tilde{s}_k = \frac{ec_k^O}{\tilde{s}(1-h_{k,k})^{1/2}} \qquad (32)$$

where $\tilde{s}$ is the residual mean, whose square is defined by the equation:

$$\tilde{s}^2 = \frac{(ec^O)^T ec^O}{m-a} \qquad (33)$$

The externally Studentized residual for k-th sample of the training set is calculated using the following equation [18]:

$$\tilde{t}_k = \frac{ec_k^O}{\tilde{s}(k)(1-h_{k,k})^{1/2}} \qquad (34)$$

where $\tilde{s}(k)$ is defined by the expression:

$$\tilde{s}^2(k) = \frac{(m-a)\tilde{s}^2 - (ec_k^O)^2 / (1-h_{k,k})}{m-a-1} \qquad (35)$$

An example plot of externally Studentized concentration residuals versus leverages calculated by cross-validation for the training set is shown in FIG. 7 (ba2, ch5, 300-860). There are three obvious outliers shown in FIG. 7. However, for one of them only the value of externally Studentized concentration residual (−4.74) is outlying, while its leverage value (0.0153) is within the training set. In contrast, the other sample has the highest outlying value of leverage (0.513) while the externally Studentized concentration residual exceeds the training set cluster values only slightly. The third outlier is determined by both leverage (0.421) and externally Studentized concentration residual (3.59). Based on the above, one can conclude that only coupling of leverages and Studentized concentration residuals gives a reliable approach for outlier detection within the training set.

Calibration Calculation

It is recommended to perform calculations aiming to obtain the optimal number of factors (by PRESS and/or Exner ψ function) and eliminating outliers by regression calculation from the training set (methods based on concentration residuals: F-ratio and Studentized concentration residuals versus leverages plot) in an iterative sequence. Iteration should stop when the optimal number of factors is calculated and there are no outliers in the training set.

Having determined the correct number of factors and the outlier-free training set, one can perform the final regression calculation using PLS-1 or PCR method. As an example calibration, the acid calibration in the five-component (copper, 14-24 g/L; acid, 140-220 g/L; chloride, 30-80 ppm; brightener, 2-9 mL/L; carrier, 3-8 mL/L) PC 75 copper plating bath (Technic, Inc.) is presented below. The calibration was performed based on a 25-solutions matrix analogous to that of Table 1 but having five components instead of six. The scan chosen for the calibration was b26, channel 3 (see FIG. 8) for the range of 4000-4800 with the optimal number of factors of 3. It is clearly demonstrated that PCR and PLS-1 methods are capable of creating an accurate calibration model from the range of the scan that contains no characteristic or significant points for univariate regression. The calibration is examined based on values of squared regression coefficients calculated from original actual concentrations and rescaled predicted concentrations:

$$(r^O)^2 = \frac{\left\{\sum_{i=1}^{m} c_i^O \hat{c}_i^O - \left(\sum_{i=1}^{m} c_i^O \sum_{i=1}^{m} \hat{c}_i^O\right)/m\right\}^2}{\left\{\sum_{i=1}^{m} (c_i^O)^2 - \left(\sum_{i=1}^{m} c_i^O\right)^2/m\right\}\left\{\sum_{i=1}^{m} (\hat{c}_i^O)^2 - \left(\sum_{i=1}^{m} \hat{c}_i^O\right)^2/m\right\}} \quad (36)$$

and PRESS (Equation 25) for self prediction and cross validation methods for internal validation for both regression methods, PCR and PLS-1 (Table 6). Both regression methods, PCR and PLS-1, perform very similarly which is also apparent in FIG. 9 presenting actual and cross validated acid concentrations If the $(r^O)^2$ is greater than about 0.95, the training set is validated. If the $(r^O)^2$ is less than about 0.95, the steps for cross validation should be repeated until an $(r^O)^2$ greater than about 0.95 is calculated.

TABLE 6

Squared correlation coefficients, $(r^O)^2$, (Equation 36) and PRESS Equation 25) calculated by PCR and PLS-1 as self prediction and cross validation for acid calibration for PC75 plating bath (scan dq21b26, ch 3, range 4000-4800, 3 factors)

|  | PCR | | PLS-1 | |
| --- | --- | --- | --- | --- |
|  | selfpred | Xval | selfpred | Xval |
| r^2 | 0.9769 | 0.9724 | 0.9771 | 0.9729 |
| PRESS | 925.8 | 1103.2 | 914 | 1082.8 |

The level of accuracy presented in Table 6 and FIG. 9 is more than satisfactory for our purposes as it consists a small fraction of the acid concentration range for PC 75 (Technic, Inc.) copper plating bath. Usually, a plating bath is designed to perform satisfactorily as long as the concentrations of all bath constituents are maintained within certain ranges that define calibration ranges.

A very important advantage of multivariate regression methods in comparison to univariate regression methods is the ability of the multivariate techniques to utilize simultaneously the information coming from different sources. This collective information can be used as a base for a calibration producing a more accurate and less biased model than multivariate calibrations but based on the data coming from single source. In order to generate an example collective data set, portions of two different voltammograms (bath PC75, ba2, ch 3, 401-701 and ch 4, 301-601) were "glued" together and regressed against brightener concentration. The modeling power corresponding to these ranges was satisfactorily high. This calibration is based on the same training set as was used for the previous example of acid calibration in a PC75 bath. Both scans used for brightener calibration do not present much value for the univariate regression as they do not contain any characteristic single points (like peaks etc.). Additionally, the least squares regression calculation conducted for each j-th point of autoscaled AC voltammograms (procedure steps 1.1-1.5) does not produce regression coefficients satisfactory for purposes discussed in this text (FIG. 10).

TABLE 7

Squared correlation coefficients, $(r^O)^2$ (Equation 36) calculated by PCR and PLS-1 as self prediction and cross validation (methods for internal validation) for number of factors 2 and 3 for brightener calibration for scan dq21ba2, channels: 3 (range 401-701), 4 (range 301-601) and "glued"data for channels 3 (range 401-701) and 4 (range 301-601)

| | PCR | | | | | | PLS-1 | | | | | |
| --- | --- | --- | --- | --- | --- | --- | --- | --- | --- | --- | --- | --- |
| # of factors | ch3 selfpred | ch3 Xval | ch4 selfpred | ch4 Xval | ch3 + ch4 selfpred | ch3 + ch4 Xval | ch3 selfpred | ch3 Xval | ch4 selfpred | ch4 Xval | ch3 + ch4 selfpred | ch3 + ch4 Xval |
| 2 | 0.7098 | 0.6903 | 0.9221 | 0.9175 | 0.9406 | 0.9372 | 0.7200 | 0.7009 | 0.9229 | 0.9183 | 0.9408 | 0.9372 |
| 3 | 0.7536 | 0.7243 | 0.9317 | 0.9250 | 0.9407 | 0.9360 | 0.9123 | 0.8985 | 0.9371 | 0.9311 | 0.9469 | 0.9414 |

Table 7 shows squared regression coefficients for brightener calibration calculated by employing Equation 36 for channel 3 only, channel 4 only and "glued" data for channels 3 and 4. One can notice that the "glued" data set produces higher $(r^O)^2$'s for both self prediction and cross validation for PCR and PLS-1. One can also notice that the range chosen for brightener calibration from ba2, ch4, 301-601 partially corresponds to the very low values of $r^2$ calculated by LSR. However, as was checked by cross validation, such an empirically extended range gives higher $(r^O)^2$ for PCR- and PLS-1-based regression than the narrower range determined purely using the $R_j r_j^2$ parameter.

Comparing data from Table 6 to that of FIG. 10, one can also notice that the squared regression coefficients calculated with multivariate techniques, PCR and PLS-1, for ba2, channel 4 data results in much higher values than that calculated with least-squares regression.

Calibration Transfer

The calibration transfer procedure is intended to overcome three major problems, which impede prediction performance of originally calculated regression equations. The first problem occurs when a calibration model developed on one instrument is transported to another instrument. A second problem is observed when the instrumental responses measured on a single instrument over a period of time change for any reason (electronic drift). Finally, a third problem is caused by the differences between samples coming from different production batches. All these three problems involve a calibration on a primary instrument and an attempt to use the calibration model on a secondary instrument that produces responses that differ in some way. These problems have been encountered quite often in our experimental practice. To deal with them, several calibration transfer techniques were applied. To the best of our knowledge calibration transfer coupled with data decomposition techniques have never been applied previously for calibration transfer of any electrochemical data. The following techniques are presented below: Direct Standardization [19] using either raw data (DS) or scores (DSS), Piecewise Direct Standardization [19] using raw data (PDS) [19], Direct Standardization with Additive Background Correction [20] using either raw data (DSB) or scores (DSBS), Piecewise Direct Standardization with Additive Background Correction [20] using raw data (PDSB) [20]. These techniques are well described in literature, apart from DSS and DSBS. Therefore it has been decided to present the DSS and DSBS methods in detail.

The procedure for DSS is as follows:
The original full calibration data set for primary instrument, $X_1^O(m, n)$, is decomposed by PCA for scores, $S_1(m,a)$, and eigenvectors, $V_1(n,a)$. The lower index "1" denotes primary instrument.

Scores $S_1$ and corresponding concentrations $c_1^O(m)$ are mean-centered (Equation 4) to obtain $\bar{S}_1$ and $\bar{c}_1$, respectively. They constitute the following regression equation:

$$\bar{c}_1 = \bar{S}_1 \beta \quad (37)$$

where $\beta(a,1)$ is a column vector of regression coefficients.
The regression coefficients are calculated employing the expression:

$$\hat{\beta} = (\bar{S}_1)^+ \bar{c}_1 \quad (38)$$

where $(\bar{S}_1)^+$ is the pseudoinverse of matrix $\bar{S}_1$ calculated via the following equation:

$$(\bar{S}_1)^+ = (\bar{S}_1^T \bar{S}_1)^{-1} \bar{S}_1^T \quad (39)$$

The scores for the original calibration data subset for primary, $X_1^{O,s}(m_s, n)$, and secondary, $X_2^{O,s}(m_s, n)$, instrument are calculated using Equations 40 and 41, respectively:

$$S_1^s = X_1^{O,s} V_1 \quad (40)$$

$$S_2^s = X_2^{O,s} V_1 \quad (41)$$

The indexes: lower "2" and upper "s" denote a secondary instrument and calibration subset, respectively.
The transformation matrix is calculated as:

$$F = (S_2^s)^+ S_1^s \quad (42)$$

Scores are calculated for a voltammogram obtained on the secondary instrument for an unknown sample, $x_{2,u}^O(1, n)$ employing the following expression:

$$S_{2,u} = x_{2,u}^O V_1 \quad (43)$$

Scores for an unknown sample from a secondary instrument are multiplied by the transformation matrix:

$$S_{2,u}^f = S_{2,u} F \quad (44)$$

The vector $s_{2,u}^f$ is centered using the grand mean for primary calibration to obtain $\bar{s}_{2,u}^f$. This vector is then used in the regression equation to obtain the mean-centered concentration of the unknown sample:

$$\bar{c}_{2,u} = \hat{\beta} \bar{s}_{2,u}^f \quad (45)$$

Finally, the mean centered concentration of the unknown sample from the secondary instrument is resealed employing parameters from concentrations of the training set resulting in value of the predicted concentration: $\hat{c}_{2,u}$.

The initial five steps of the procedure for DSBS are identical to the initial steps of the procedure for DSS. However, before applying the regression equation, several additional coefficients should be calculated. The procedure for DSBS is as follows:

The original full calibration data set for primary instrument, $X_1^O(m, n)$, is decomposed by PCA for scores, $S_1(m,a)$, and eigenvectors, $V_1(n,a)$. The lower index "1" denotes primary instrument.

Scores $S_1$ and corresponding concentrations $c_1^O(m)$ are mean-centered (Equation 4) to obtain $\bar{S}_1$ and $\bar{c}_1$, respectively. They constitute the regression Equation 37.

The regression coefficients are calculated employing Equation 38.

The scores for the original calibration data subset for primary, $X_1^{O,s}(m_s, n)$, and secondary, $X_2^{O,s}(m_s, n)$, instrument are calculated using Equations 40 and 41, respectively.

The transformation matrix is calculated according to Equation 42.

An estimate of the regression vector for full calibration for the primary instrument is calculated employing the expression:

$$b_1 = c_1^\mu - s_1^\mu \hat{\beta} \quad (46)$$

where $c_1^\mu$ and $s_1^\mu$ contain mean column values of $c_1$ and $S_1$, respectively, and $\hat{\beta}$ is calculated using Equation 38.

The background vector $b_g(1, a)$, introduced to accommodate the additive background difference between the instruments, is calculated by applying following equation:

$$b_g = s_1^{s,\mu} - s_2^{s,\mu} F \quad (47)$$

where vectors $s_1^{s,\mu}$ and $s_2^{s,\mu}$ contain mean column values of matrices $S_1^s$ and $S_2^s$, respectively.

Scores are calculated for a voltammogram obtained on the secondary instrument for an unknown sample, $x_{2,u}^O(1, n)$ employing Equation 43.

Scores for an unknown sample from a secondary instrument are multiplied by the transformation matrix (Equation 44).

Finally, the following equation is used to predict the concentration of the unknown sample analyzed with the secondary instrument:

$$\hat{c}_{2,u} = (s_{2,u}^f + b_g)\hat{\beta} + b_1 \quad (48)$$

where $s_{2,u}^f$, $b_g$, $\hat{\beta}$ and $b_1$ are computed from Equations 44, 47, 38 and 46, respectively.

All calibration transfer techniques were implemented in the MATLAB environment.

Procedures for DSS and DSBS were written following exactly the algorithms presented above. Remaining standardization procedures were implemented using the PLS Toolbox.

TABLE 8

Squared regression coefficient, $(r^O)^2$, (Equation 36) and PRESS (Equation 25) calculated using predicted acid (scan dq21b26, channel 3, range 3600-4350, 4 factors) concentrations for a secondary instrument employing regression equations obtained via various standardization methods: no standardization, DS, DSB, PDS, PDSB, DSS and DSBS.

| Method of standardization | $r^2$ | PRESS | ref. |
| --- | --- | --- | --- |
| no standardization | 0.97592 | 393020 | FIG. 9a |
| DS | 0.96003 | 1309.1 | FIG. 9b |

TABLE 8-continued

Squared regression coefficient, $(r^O)^2$, (Equation 36) and PRESS (Equation 25) calculated using predicted acid (scan dq21b26, channel 3, range 3600-4350, 4 factors) concentrations for a secondary instrument employing regression equations obtained via various standardization methods: no standardization, DS, DSB, PDS, PDSB, DSS and DSBS.

| Method of standardization | $r^2$ | PRESS | ref. |
|---|---|---|---|
| DSB | 0.96737 | 930.5 | FIG. 9c |
| PDS | 0.97592 | 929 | FIG. 9d |
| PDSB | 0.97613 | 663.1 | FIG. 9e |
| DSS | 0.9707 | 1015.7 | FIG. 9f |
| DSBS | 0.97756 | 611.1 | FIG. 9g |

The performance of DS, DSB, PDS, PDSB, DSS and DSBS is compared in FIG. 11 and in Table 8 for the example of sulfuric acid calibration for PC 75 copper plating bath (Technic, Inc.). The regression equation calculated for the calibration of the primary instrument was used to predict concentration based on the voltammograms obtained on the secondary instrument. The predicted concentrations calculated using various calibration transfer techniques are presented in comparison to actual concentrations. In FIG. 11a, no calibration transfer techniques were applied and the data from the secondary instrument was directly predicted with the primary instrument regression equation. Analyzing data in Table 8, one can notice that squared correlation coefficient (Equation 36) is not a sufficient parameter for measuring the performance of calibration transfer techniques. Therefore, the performance was also analyzed based on PRESS (Equation 25) values. The techniques with additive background correction have resulted in lower values of PRESS than by corresponding techniques without additive background correction suggesting existence of a structured, nonlinear background. The DSS is performing more accurately and much faster than regular DS. DSBS gives the most accurate prediction. Although, the performances of PDSB and DSBS are very similar to each other, DSBS is preferred because of a much shorter time is required for its computations.

REFERENCES

The following background documents are cited herein. To the extent necessary for a full and complete understanding of this invention, the disclosure of these documents is hereby incorporated herein by reference:

P1 R. Haak, C. Ogden and D. Tench Plating and Surface Finishing, 68 (4) (1981) 52.
P2 R. Haak, C. Ogden and D. Tench Plating and Surface Finishing, 69 (3) (1982) 62.
P3 L. Graham, ECS Meeting Honolulu, 1999, Abstract #729.
P4 W. O. Freitag, C. Ogden, D. Tench and J. White Plating and Surface Finishing, 70 (10) (1983) 55.
P5 D. Tench and J. White J. Electrochem. Soc, 132 (4) (1985) 831.
P6 Fisher U.S. Pat. No. 4,917,774.
P7 B. M. Eliash U.S. Pat. No. 5,298,129.
P8 W. Sonnenberg, R. Bernards, P. Houle and G. Fisher U.S. Pat. No. 5,223,118.
P9 I. H. Chang and W. J. Horkans U.S. Pat. No. 5,192,403.
P10 I. H. Chang and W. J. Horkans U.S. Pat. No. 5,196,096.
P11 F. A. Ludwig U.S. Pat. No. 4,631,116.
P12 W. D. Bonivert, J. C. Farmer and J. T. Hachman U.S. Pat. No. 4,812,210.
P13 J. S. Krafcik, Jr., W. D. Bonivert, J. T. Hachman and J. C. Farmer Proceedings of the World Congress on Metal Finishing, Interfinish 92, International Union of Surface Finishing, Brasil, October 1992.
P14 S. S. Heberling, D. Campbell and S. Carson, PC Fab, 12 (8) (1989) 72.
P15 B. Newton and E. Kaiser, ECS Meeting Toronto, 1999, Abstract #327.
P16 J. Horkans and J. O. Dukovic, ECS Meeting Toronto, 1999, Abstract #360.
P17 B. M. Eliash, F. A. Ludwig, N. H. Phan and V. N. Reddy U.S. Pat. No. 5,298,131.
P18 N. H. Phan, V. N. R. K. Reddy, F. A. Ludwig and B. M. Eliash U.S. Pat. No. 5,336,380.
P19 F. A. Ludwig, C. Manger and K. Wikiel U.S. Pat. No. 5,755,954.
L1 Brown, S. D.; Bear, Jr., R. S. CRC Crit. Rev. Anal. Chem. 24, 1993, 99.
L2 Henrion, A.; Henrion, R.; Henrion, G.; Scholz, F. Electroanalysis 2, 1990, 309.
L3 Ni, Y.; Kokot, S.; Selby, M.; Hodgkinson, M. Electroanalysis 4, 1992, 713.
L4 Ni, Y.; Kokot, S.; Selby, M.; Hodgkinson, M. Anal. Chim. Acta 316, 1995, 233.
L5 Ni, Y.; Bai, J.; Jin, L. Anal. Chim. Acta 329 (1996) 65.
L6 Ni, Y.; Bai, J.; Jin, L. Anal. Lett. 30, 1997, 1761.
L7 Ni, Y.; Wang, L.; Kokot, S. Anal. Chim. Acta 412, 2000, 185.
L8 Ni, Y.; Wang, L; Kokot, S. Anal. Chim. Acta 439, 2001, 159.
L9 Alonso Lomillo, M. A.; Dominguez Renedo, O.; Arcos Martinez, M. J. Anal. Chim. Acta 449, 2001, 167.
L10 Allus, M. A.; Brereton, R. G. Analyst 117, 1992, 1075.
L11 Reviejo, A. J.; Buyo, F. J.; Pingarron, J. M.; Peral, J. L. Electroanalysis 5, 1993, 303.
L12 Jagner, D.; Renman, L.; Stefansdottir, S. H. Electroanalysis 6, 1994, 201.
L13 Cabanillas, A. G.; Diaz, T. G.; Espinosa-Mansilla, A.; Lopez, F. S. Talanta, 41, 1994, 1821.
L14 Cabanillas, A. G.; Diaz, T. G.; Espinosa-Mansilla, A.; Lopez-de-Alba, P. L.; Lopez, F. S. Anal. Chim. Acta 302, 1995, 9.
L15 Galeano Diaz, T.; Guiberteau Cabanillas, A.; Acedo Valenzuela, M. I.; Salinas F. Analyst 121, 1996, 547.
L16 Guiberteau, A.; Galeano Diaz, T.; Salinas, F.; Ortiz, J. M. Anal. Chim. Acta. 305, 1995, 219.
L17 Galeano Diaz, T.; Guiberteau Cabanillas, A.; Alexandre Franco, M. F.; Salinas, F.; Vire, J.-C. Electroanalysis 10, 1998, 497.
L18 Guiberteau Cabanillas, A.; Galeano Diaz, T.; Mora Diez, N. M.; Salinas, F.; Ortiz Burguillos, J. M.; Vire J.-C. Analyst, 125, 2000, 909.
L19 Lastres, E.; De Armas, G.; Catasus, M.; Alpizar, J.; Garcia, L.; Cerda, V. Electroanalysis 9, 1997, 251.
L20 Chan. H.; Butler, A.; Falck, D. M.; Freund, M. S. Anal. Chem. 69, 1997, 2373.
L21 Richards, E.; Bessant, C.; Saini, S. Chemom. Intell. Lab. Syst. 61, 2002, 35.
L22 Wehrens, R.; van der Linden, W. E. Anal. Chim. Acta 334, 1996, 93.
L23 Matos, R. C.; Angnes, L.; Araujo, M. C. U.; Saldanha, T. C. B. Analyst, 125, 2000, 2011.
L24 Diaz-Cruz, J. M.; Tauler, R.; Grabaric, B. S.; Esteban, M.; Casassas, E. J. Electroanal. Chem. 393, 1995, 7.

L25 Mendieta, J.; Diaz-Cruz, M. S.; Tauler, R.; Esteban, M. Anal. Biochem. 240, 1996, 134.

L26 Diaz-Cruz, M. S.; Mendieta, J.; Tauler, R.; Esteban, M. J. Inorg. Biochem. 66, 1997, 29.

L27 Diaz-Cruz, M. S.; Mendieta, J.; Monjonell, A.; Tauler, R.; Esteban, M. J. Inorg. Biochem. 70, 1998, 91.

L28 Diaz-Cruz, M. S.; Mendieta, J.; Monjonell, A.; Tauler, R.; Esteban, M. Anal. Chim. Acta 385, 1999, 353.

L29 Diaz-Cruz, M. S.; Mendieta, J.; Monjonell, A.; Tauler, R.; Esteban, M. Anal. Chim. Acta 390, 1999, 15.

L30 Cruz, B. H.; Diaz-Cruz, J. M.; Diaz-Cruz, M. S.; Ariño, C.; Esteban, M.; Tauler, R.; J. Electroanal. Chem. 516, 2001, 10.

L31 Cruz-Vasquez, B. H.; Diaz-Cruz, J. M.; Ariño, C.; Esteban, M.; Tauler, R. Analyst, 127, 2002, 401.

L32 Grabaric, B. S.; Grabaric, Z.; Tauler, R.; Esteban, M.; Casassas, E. Anal. Chim. Acta 341, 1997, 105.

L33 Torres, M.; Diaz-Cruz, J. M.; Ariño, C.; Grabaric, B.S.; Tauler, R.; Esteban, M. Anal. Chim. Acta 371, 1998, 23.

L34 Esteban, M.; Harlyk, C.; Rodriguez, A. R. J. Electroanal. Chem. 468, 1999, 202.

L35 Diaz-Cruz, M. S.; Mendieta, J.; Tauler, R.; Esteban, M. Anal. Chem. 71, 1999, 4629.

L36 Fernandez, M.; Ariño, C.; Diaz-Cruz, J. M.; Tauler, R.; Esteban, M. Electroanalysis 13, 2001, 1405.

L37 Diaz-Cruz, M. S.; Diaz-Cruz, J. M.; Mendieta, J.; Tauler, R.; Esteban, M. Anal. Biochem. 279, 2000, 189.

L38 Fernandez, M.; Ariño, C.; Diaz-Cruz, J. M.; Tauler, R.; Esteban, M.; J. Electroanal. Chem. 505, 2001, 44.

L39 Cruz, B. H.; Diaz-Cruz, J. M.; Ariño, C.; Tauler, R.; Esteban, M. Anal. Chim. Acta 424, 2000, 203.

L40 Esteban, M.; Ariño, C.; Diaz-Cruz, J. M.; Diaz-Cruz, M. S.; Tauler, R. Trends Anal. Chem. 19, 2000, 49.

L41 Diaz-Cruz, J. M.; Agullo, J.; Diaz-Cruz, M. S.; Ariño, C.; Esteban, M.; Tauler, R. Analyst 126, 2001, 371.

L42 Berzas, J. J.; Rodriguez, J.; Castañeda, G. Anal. Chim. Acta. 349, 1997, 303.

L43 Saurina, J.; Hemandez-Cassou, S.; Fabregas, E.; Alegret, S. Anal. Chim. Acta 405, 2000, 153.

L44 Herrero, A.; Cruz Ortiz, M. Anal. Chim. Acta. 348, 1997, 51.

L45 Herrero, A.; Cruz Ortiz, M. Talanta 46, 1998, 129.

L46 Herrero, A.; Cruz Ortiz, M. J. Electroanal. Chem. 432, 1997, 223.

L47 Herrero, A.; Cruz Ortiz, M. Talanta 49, 1999, 801.

L48 Herrero, A.; Cruz Ortiz, M. Anal. Chim. Acta 378, 1999, 245.

L49 Sanz, M. B.; Sarabia, L. A.; Herrero, A.; Cruz Ortiz, M. Anal. Chim. Acta 446, 2001, 297.

L50 Engholm, S. O. Anal. Chem. 64, 1992, 2530.

L51 Engholm, S. O. J. Electroanal. Chem. 332, 1992, 73.

L52 Simons, J.; Bos, M.; van der Linden, W. E. Analyst 120, 1995, 1009.

L53 Chow, C. W. K.; Davey, D. E.; Mulcahy, D. E.; Yeow, T. C. W. Anal. Chim. Acta 307, 1995, 15.

L54 Economou, A.; Fielden, P. R.; Gaydecki, P. A.; Packham, A. J. Analyst 119, 1994, 847.

L55 Economou, A.; Fielden, P. R. Anal. Chim. Acta 305, 1995, 165.

L56 Do Lago, C. L.; Juliano, V. F.; Kascheres, C. Anal. Chim. Acta 310, 1995, 281.

L57 Zou, X.; Mo, J. Anal. Chim. Acta 340,1997, 115.

L58 Zheng, X.-P.; Mo, J.-Y. Chemom. Intell. Lab. Syst. 45, 1999, 157.

L59 Chow, C. W. K.; Davey, D. E.; Mulcahy, D. E. Anal. Chim. Acta, 338, 1997, 167.

L60 Palys, M.; Bos, M.; van der Linden, W. E. Anal. Chim. Acta 231, 1990, 59.

L61 Palys, M.; Bos, M.; van der Linden, W. E. Anal. Chim. Acta 248, 1991, 429.

L62 Palys, M. J.; Bos, M.; van der Linden, W. E. Anal. Chim. Acta 283, 1993, 811.

L63 Palys, M. J.; Bos, M.; van der Linden, W. E. Anal. Chim. Acta 284, 1993,107.

L64 Ruisanchez, I.; Larrechi, M. S.; Rius, F. X.; Esteban, M. Trends Anal. Chem. 11, 1992, 135.

L65 Esteban, M.; Ruisanchez, I.; Larrechi, M. S.; Rius, F. X. Anal. Chim. Acta 268, 1992, 95.

L66 Esteban, M.; Ruisanchez, I.; Larrechi, M. S.; Rius, F. X. Anal. Chim. Acta 268, 1992, 107.

L67 Esteban, M.; Ariño, C.; Ruisanchez, I.; Larrechi, M. S.; Rius, F. X. Anal. Chim. Acta 284, 1993, 435.

L68 Esteban, M.; Ariño, C.; Ruisanchez, I.; Larrechi, M. S.; Rius, F. X. Anal. Chim. Acta 285, 1994, 193.

L69 Esteban, M.; Ariño, C.; Ruisanchez, I.; Larrechi, M. S.; Rius, F. X. Anal. Chim. Acta 285, 1994, 377.

L70 Garcia-Armada, M. P.; Losada, J.; de Vicente-Perez, S. Anal. Chim. Acta 316, 1995, 47.

[1] Sharaf, M. H.; Illman, D. L. and Kowalski, B. R. Chemometrics, Wiley, New York, 1986.

[2] Geladi, P. and Kowalski, B. R. Anal. Chim. Acta 185 (1986) 1.

[3] Davis, J. C. Statistics and Data Analysis in Geology, Wiley, New York, 1986.

[4] Malinowski, E. R. Factor Analysis in Chemistry, $2^{nd}$ Ed., Wiley, New York, 1991.

[5] Wold, S.; Esbensen, K. and Geladi, P. Chemom. and Intell. Lab. Syst. 2 (1987) 37.

[6] Donahue, S. M. and Brown, C. W. Anal. Chem. 63 (1991) 980.

[7] Press, W. H.; Teukolsky, S. A.; Vetterling, W. T. and Flannery, B. P. Numerical Recipes in C. The Art of Scientific Computing, $2^{nd}$ Ed., Cambridge University Press, Cambridge, 1992.

[8] Sprott, J. H. Numerical Recipes. Routines and Examples in BASIC, Cambridge University Press, Cambridge, 1991.

[9] Gemperline, P. J.; Shah, N. K. Anal. Chem. 62 (1990) 465.

[10] Rousseeuw, P. J. and Van Driessen, K. Technometrics 41 (1999) 212.

[11] Egan, W. J. and Morgan, S. L. Anal. Chem. 70 (1998) 2372.

[12] Kramer, R. Chemometric Techniques for Quantitative Analysis, Dekker, New York, 1998.

[13] Martens, H. and Naes, T. Multivariate Calibration, Wiley, New York, 1989.

[14] Höskuldsson, A. Prediction Methods in Science and Technology, Thor Publishing, Denmark, 1996.

[15] Haaland, D. M. and Thomas, E. V. Anal. Chem. 60 (1988) 1193.

[16] Kindsvater, J. H.; Weiner, P. H. and Klingen, T. J. Anal. Chem. 46 (1974) 982.

[17] Exner, O. Collect. Czech. Chem. Commun. 37 (1966) 3222.

[18] Draper, N. R. and Smith, H. Applied Regression Analysis, $3^{rd}$ Ed., Wiley, New York, 1998.

[19] Wang, Y.; Veltkamp, D. J.; Kowalski, B. R. Anal. Chem. 63 (1991) 2750.

[20] Wang, Z.; Dean, T.; Kowalski, B. R. Anal. Chem. 67 (1995) 2379.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A process to produce a predictive data set which can be used to predict the amount of target constituent in an electrolyte solution, said process comprising:
   (a) providing a multi-component electrolyte solution comprising constituents which possess significantly different electrochemical properties,
      said constituents being present in the electrolyte solution at concentrations significantly different from each other,
      said constituents interacting electrochemically with each other in the electrolyte solution;
   (b) obtaining a sample set, wherein each sample of the sample set comprises an electrolyte solution of step (a) with known composition;
   (c) obtaining an electroanalytical response for each said sample to produce a electroanalytical response data set, wherein said electroanalytical response comprises a combination of one or more portions of independent electroanalytical responses;
   (d) obtaining a training set that comprises said sample set and the corresponding said electroanalytical response data set;
   (e) analyzing said training set using decomposition and multivariate regression method to produce a regression data set; and
   (f) validating said training data set to produce said predictive data set for a predictive calibration model.

2. A process according to claim 1, wherein said electrolyte solution is an electroplating bath.

3. A process of claim 2, wherein said electroplating bath comprises a plating bath of one or more metals selected from the group consisting of Cu, Sn, Pb, Zn, Ni, Ag, Cd, Co, Cr, and/or their alloys.

4. A process according to claim 1, wherein said electrolyte solution is an electroless plating bath.

5. A process of claim 4, wherein said electroless plating bath comprises an autocatalytic plating bath of one or more metals selected from the group consisting of Cu, Sn, Pb, Ni, Ag, Au, and/or their alloys.

6. A process of claim 4, wherein said electroless plating bath comprises an immersion plating bath of one or more metals selected from the group consisting of Cu, Sn, Pb, Ni, Ag, Au and/or their alloys.

7. A process according to claim 1, wherein said electrolyte solution is an electrowinning bath.

8. A process of claim 7, wherein said electrowinning bath comprises a plating bath of one or more metals selected from the group consisting of Cu, Sn, Pb, Zn, Ni, Ag, Cd, Co, Cr, and/or their alloys.

9. A process according to claim 1, wherein said electrolyte solution is an electrorefining bath.

10. A process of claim 9, wherein said electrorefining bath comprises a plating bath of one or more metals selected from the group consisting of Cu, Sn, Pb, Zn, Ni, Ag, Cd, Co, Cr, and/or their alloys.

11. A process according to claim 1, wherein said electrolyte solution is an electroforming bath.

12. A process of claim 11, wherein said electroforming bath comprises a plating bath of one or more metals selected from the group consisting of Cu, Sn, Pb, Zn, Ni, Ag, Cd, Co, Cr, and/or their alloys.

13. A process according to claim 1, wherein said electrolyte solution is an electromicromachining bath.

14. A process of claim 13, wherein said electromicromachining bath comprises a plating bath of one or more metals selected from the group consisting of Cu, Sn, Pb, Zn, Ni, Ag, Cd, Co, Cr, and/or their alloys.

15. A process according to claim 1, wherein said electrolyte solution is an electropolishing bath.

16. A process according to claim 1, wherein said sample data set of step (b) is obtained by design of experiment (DOE) routines.

17. A process according to claim 16, wherein said DOE routine is multicomponent multilevel linear orthogonal array.

18. A process according to claim 16, wherein said DOE routine is multicomponent multilevel fractional factorial.

19. A process according to claim 1, wherein the electroanalytical response of step (c) is obtained by DC Voltammetry selected from the group consisting of:
   DC cyclic Voltammetry;
   DC Linear Scan Voltammetry;
   DC Anodic Stripping Voltammetry;
   DC Cathodic Stripping Voltammetry;
   DC Adsorptive Stripping Voltammetry;
   DC Cyclic Voltammetric Stripping technique;
   DC Staircase Voltammetry;
   and combinations thereof.

20. A process according to claim 1, wherein the electroanalytical response of step (c) is obtained by a technique selected from the group consisting of:
   Normal Pulse Voltammetry;
   Reverse Pulse Voltammetry;
   Differential Pulse Voltammetry;
   Square Wave Voltammetry;
   AC Voltammetry;
   Chronoamperometry;
   Chronopotentiometry;
   Electrochemical Impedance Spectroscopy technique;
   Polarographic techniques;
   and combinations thereof.

21. A process according to claim 1, wherein said electroanalytical response of step (c) comprises a plurality of data points.

22. A process according to claim 1, wherein said regression data set of step (e) is obtained by a technique selected from the group consisting of:
   sequential decomposition followed by a multivariate regression (PCR);
   simultaneous decomposition and regression (PLS);
   internal validation;
   external validation;
   and combinations thereof.

23. A process according to claim 22, wherein said internal validation uses cross validation comprising the following steps:
   (a) omitting a single sample from said training set, thereby creating a new training set;
   (b) analyzing said new training said using decomposition and multivariate regression method to produce a new regression data set;
   (c) predicting said omitted sample target component concentration using said new regression data set;
   (d) returning sample to the training set;
   (e) repeating steps (1) through (4) until all individual samples were treated;
   (f) determining an $R^2$ value for said predicted samples based on said predicted and said known concentrations;

(g) validating said training data set if said $R^2$ value is above about 0.95; and repeating steps (a) to (f) if said $R^2$ value is less than about 0.95.

24. A process according to claim 23, wherein said internal validation uses cross validation comprising the following steps:
(a) obtaining a second sample set comprises an electrolyte solution of known composition;
(b) obtaining an electroanalytical response for each sample of said second sample set;
(c) predicting said target component concentration for each sample of said second sample set using said predictive calibration model;
(d) determining an $R^2$ value for all samples of said second sample set based on said predicted and said known concentrations;
(e) validating said predictive calibration model if said $R^2$ value is above about 0.95; and repeating steps (a) to (e) if said $R^2$ value is less than about 0.95.

25. A process to produce a predictive data set which can be used to predict the amount of target constituent in an electrolyte solution, said process comprising:
(a) providing a multi-component electrolyte solution comprising constituents which possess significantly different electrochemical properties,
said constituents being present in the electrolyte solution at concentrations significantly different from each other,
said constituents interacting electrochemically with each other in the electrolyte solution
(b) obtaining a sample set, wherein each sample of the sample set comprises an electrolyte solution of step (a) with known composition;
(c) obtaining an electroanalytical response for each said sample to produce a electroanalytical response data set;
(d) obtaining a training set that comprises said sample set and the corresponding said electroanalytical response data set;
(e) analyzing said training set using decomposition and multivariate regression method to produce a regression data set; and
(f) validating said training data set to produce said predictive data set for a predictive calibration model;
wherein said electroanalytical response of step (c) is obtained by:
(1) obtaining a first electroanalytical response for each said sample using a first electroanalytical technique,
(2) obtaining a second electroanalytical response for each said sample using a second electroanalytical technique,
(3) independently determining optimal portions for calibration of said first and second electroanalytical responses,
(4) combining the optimal portions of said first and second electroanalytical responses.

26. A process of producing a calibration data set to predict the amount of a target constituent in electrolyte solution, the process comprising:
(a) providing a multi-component electrolyte solution comprising constituents which possess different electrochemical properties,
said constituents being present in the electrolyte solution at concentrations significantly different from each other,
said constituents interacting electrochemically with each other in the electrolyte solution;
(b) obtaining a sample set, wherein each sample of the sample set comprises an electrolyte solution of step (a) with known composition;
(c) obtaining an electroanalytical response for each said sample to produce an electroanalytical response data set, wherein said electroanalytical response comprises a combination of one or more portions of independent electroanalytical responses;
(d) obtaining a training set that comprises said sample set and corresponding said electroanalytical response data set;
(e) preprocessing of training set;
(f) determining the calibration range;
(g) detecting and eliminating outliers from the response data set;
(h) determining the optimal number of factors;
(i) detecting and eliminating outliers within training set;
(j) analyzing training set using multivariate regression to produce a regression set;
(k) validating said regression set to produce a predictive set for a predictive calibration model.

27. A process according to claim 26, wherein said electrolyte solution is selected from the group consisting of:
an electroplating bath;
an electroless plating bath;
an electrowinning bath;
an electrorefining bath;
an electroforming bath;
an electromicromachining bath; or
an electropolishing bath.

28. A process according to claim 26, wherein said sample data set of step (b) is obtained by design of experiment (DOE) routines.

29. A process according to claim 28, wherein said DOE routine is multi-component multilevel linear orthogonal array.

30. A process according to claim 28, wherein said DOE routine is multicomponent multilevel fractional factorial.

31. A process according to claim 28, wherein the electroanalytical response of step (c) is obtained by DC Voltammetry.

32. A process of claim 31, wherein the DC Voltammetry technique is selected from the group consisting of:
DC Cyclic Voltammetry;
DC Linear Scan Voltammetry;
DC Anodic Stripping Voltammetry;
DC Cathodic Stripping Voltammetry;
DC Adsorptive Stripping Voltammetry;
DC Cyclic Voltammetric Stripping technique;
or combinations thereof.

33. A process according to claim 26, wherein the electroanalytical response of step (c) is obtained by a technique selected from the group consisting of:
DC Staircase Voltammetry;
Normal Pulse Voltammetry;
Reverse Pulse Voltammetry;
Differential Pulse Voltammetry;
Square Wave Voltammetry;
AC Voltammetry;
Chronoamperometry;
Chronopotentiometry;
Electrochemical Impedance Spectroscopy technique;
Polarographic techniques;
or combinations thereof.

34. A process according to claim 26, wherein said electroanalytical response of step (c) comprises a plurality of data points.

35. A process according to claim 26, wherein said electroanalytical response of step (c) is a combination of one or more portions of a complete electroanalytical response.

36. A process according to claim 26, wherein said electroanalytical response of step (c) comprises a combination of one or more portions of independent electroanalytical responses.

37. The method of claim 26, wherein step (e) comprises autoscaling the data to unit variance.

38. The method of claim 37, wherein autoscaling the data to unit variance comprises the steps of:
performing mean centering; and
dividing by the standard deviation.

39. The method of claim 26, wherein step (f) comprises the steps of:
1) analyzing the data using correlation coefficient calculations based on the least squares regression;
2) analyzing the data using SIMCA based calculations of modeling power; and
3) analyzing the data using a product of said correlation coefficient and said modeling power.

40. The method of claim 26, wherein step (g) comprises analyzing the data using a technique selected from the group consisting of:
principle component analysis;
Mahalanobis distance;
Mahalanobis distance coupled with principal component analysis;
Mahalanobis distance coupled with principal component analysis with Q residuals;
SIMCA;
or further combinations thereof.

41. The method of claim 26, wherein step (h) comprises analyzing the data using PRESS analysis.

42. The method of claim 41, wherein said PRESS analysis is based on PCR calculations.

43. The method of claim 41, wherein said PRESS analysis is based on PLS calculations.

44. The method of claim 26, wherein step (g) comprises analyzing the data using Exner psi function calculations.

45. The method of claim 44, wherein said Exner psi function analysis is based on PCR calculations.

46. The method of claim 44, wherein said Exner psi function analysis is based on PLS calculations.

47. The method of claim 26, wherein step (i) comprises analyzing the data using a technique selected from the group consisting of:
$F^C$-ratio analysis;
Studentized concentration residuals analysis;
leverages analysis; and
coupled Studentized concentration residuals analysis and leverages analysis.

48. The method of claim 26, wherein step (j) comprises analyzing the data using a technique selected from the group consisting of PLS and PCR.

49. A process according to claim 26, wherein said validation step (k) is accomplished through internal validation and external validation.

50. A process according to claim 49, wherein said internal validation uses cross validation comprising the following steps:
(1) omitting a single sample from said training set, thereby creating a new training set;
(2) analyzing said new training said using decomposition and multivariate regression method to produce a new regression data set;
(3) predicting said omitted sample target component concentration using said new regression data set;
(4) returning sample to the training set;
(5) repeating steps (1) through (4) until all individual samples were treated;
(6) determining an $R^2$ value for said predicted samples based on said predicted and said known concentrations; and
(7) validating said training data set if said $R^2$ value is above about 0.95; and repeating steps (a) to (k) if said $R^2$ value is less than about 0.95.

51. A process according to claim 49, wherein said internal validation uses cross validation comprising the following steps:
obtaining a second sample set comprises an electrolyte solution of known composition;
obtaining an electroanalytical response for each sample of said second sample set; predicting said target component concentration for each sample of said second sample set using said predictive calibration model;
determining an $R^2$ value for all samples of said second sample set based on said predicted and said known concentrations;
validating said predictive calibration model if said $R^2$ value is above about 0.95; and repeating steps (a) to (k) if said $R^2$ value is less than about 0.95.

52. A process to predict the concentration of target constituent in an electrolyte solution, said process comprising:
(a) producing a predictive data set, the predictive data set generated by:
(a1) providing a multi-component electrolyte solution comprising constituents which possess different electrochemical properties,
said constituents being present in the electrolyte solution at concentrations significantly different from each other,
said constituents interacting electrochemically with each other in the electrolyte solution;
(a2) obtaining a sample set, wherein each sample of the sample set comprises an electrolyte solution of step (a1) with known composition;
(a3) obtaining an electroanalytical response for each said sample to produce an electroanalytical response data set, wherein said electroanalytical response comprises a combination of one or more portions of independent electroanalytical responses;
(a4) obtaining a training set that comprises said sample set and corresponding said electroanalytical response data set;
(a5) analyzing said training set using decomposition and multivariate regression method to produce a regression data set:
(a6) validating said training data set to produce said predictive data set for a predictive calibration model.
(b) using said predictive data set to predict the concentration of target constituent, said concentration predicted by:
(b1) obtaining an unknown sample set, wherein each unknown sample in said unknown sample set contains an electrolyte solution of step (a1);
(b2) obtaining an electroanalytical response for each said unknown sample to produce an electroanalytical response data set;
(b3) preprocessing of said electroanalytical response data set; and (b4) applying said predictive calibration model to predict concentration of target component in each said sample.

53. A process to create a predictive data set, which can be employed to the other systems to predict the amount of a target constituent in an electrolyte solution, said process comprising:
(a) producing a predictive data set on a primary system by:
(a1) providing a multi-component electrolyte solution comprising constituents which possess different electrochemical properties,
said constituents being present in the electrolyte solution at concentrations significantly different from each other,
said constituents interacting electrochemically with each other in the electrolyte solution;
(a2) obtaining a primary sample set, wherein each sample comprises an electrolyte solution of step (a1) with known composition;
(a3) obtaining a primary electroanalytical response for each said sample to produce an electroanalytical response data set, wherein said primary electroanalytical response comprises a combination of one or more portions of independent electroanalytical responses;
(a4) obtaining a primary training set that comprises said primary sample set and corresponding said primary electroanalytical response data set;
(a5) preprocessing the primary training set;
(a6) determining the calibration range;
(a7) detecting and eliminating outliers from the primary response data set;
(a8) determining the optimal number of factors;
(a9) detecting an eliminating outliers within said primary training;
(a10) analyzing primary training set using multivariate regression to produce a regression set;
(a11) validating said primary training set to produce a predictive set for a predictive calibration model.

(b) producing a transformation data set for a secondary system, said process comprising:
(b1) obtaining a secondary sample set that is a subset of said primary sample set;
(b2) obtaining an electroanalytical response for each said secondary sample to produce an electroanalytical secondary response data set, wherein said secondary electroanalytical response comprises a combination of one or more portions of independent electroanalytical responses;
(b3) obtaining secondary-to-primary transformation data set.
(c) using said transformation data set and primary predictive data set to predict the concentration of target constituent for a secondary system said process comprising:
(c1) obtaining an unknown sample set, wherein each unknown sample in said unknown sample set contains an electrolyte solution of step (a1);
(c2) obtaining an electroanalytical response for each said unknown sample by the secondary system to produce an electroanalytical response data set;
(c3) applying said transformation data set and primary predictive data set to predict a concentration of target constituent in each said sample.

54. The method of claim 53, wherein step (b3) is selected from the group consisting of:
Direct Standardization technique;
Direct Standardization coupled with PCA technique;
Piecewise Direct Standardization technique;
Direct Standardization with Additive Background Correction technique;
Direct Standardization with Additive Background Correction coupled with PCA technique;
Piecewise Direct Standardization with Additive.

* * * * *

UNITED STATES PATENT AND TRADEMARK OFFICE
CERTIFICATE OF CORRECTION

PATENT NO. : 7,270,733 B2
APPLICATION NO. : 10/621247
DATED : September 18, 2007
INVENTOR(S) : Kazimierz J. Wikiel et al.

It is certified that error appears in the above-identified patent and that said Letters Patent is hereby corrected as shown below:

On the title page under item (56) OTHER PUBLICATIONS on page 1, third and fourth citations, kindly replace the publication title "Tench Plating and Surface Finishing" with --Tech Plating and Surface Finishing--.

In the OTHER PUBLICATIONS item (56) on page 2, left-hand column, 15th citation, kindly insert --Journal of-- before the publication title "Electroanal. Chem."

In the OTHER PUBLICATIONS item (56) on page 2, right-hand column, in the fifth citation, kindly replace the word "Resolutin" with --Resolution--; in the sixth citation, kindly replace the word "Compleses" with --Complexes--; in the ninth citation, kindly replace the word "Mutivariate" with --Multivariate--; in the 13th citation, kindly replace the word "Polargraphic" with --Polarographic--; in the 17th citation, kindly replace the word "Polargraphy" with --Polarography--; in the 19th and 20th citations, kindly replace the author's name "Engbolm" with --Engholm--.

In the OTHER PUBLICATIONS item (56) on page 3, left-hand column, in the first citation, kindly replace the word "Digial" with --Digital--; in the third citation, kindly replace the work "Sepctrometry" with --Spectrometry--; in the fourth citation, kindly replace the word "Volatmmetric" with --Voltammetric--; in the eighth citation, kindly replace the word "Polarograpic" with --Polarographic--; in the ninth citation, kindly replace the word "Polargraphic" with --Polarographic--.

Under item (56) OTHER PUBLICATIONS on page 3, right-hand column, in the first citation, kindly replace the author's name "Knowalski" with --Kowalski--; in the seventh citation, kindly replace the word "Carborances" with --Carboranes--; in the tenth citation, kindly replace the word "Standarization" with --Standardization--; in the 13th citation, kindly replace the word "Radioistope" with --Radioisotope--.

UNITED STATES PATENT AND TRADEMARK OFFICE
CERTIFICATE OF CORRECTION

PATENT NO. : 7,270,733 B2
APPLICATION NO. : 10/621247
DATED : September 18, 2007
INVENTOR(S) : Kazimierz J. Wikiel et al.

It is certified that error appears in the above-identified patent and that said Letters Patent is hereby corrected as shown below:

At column 12, lines 10-15, kindly replace the equation " $X_j^\mu = \frac{\sum_{i=1}^{m} X_{i,j}^o}{m}$ " with -- $x_j^\mu = \frac{\sum_{i=1}^{m} x_{i,j}^o}{m}$ --; at lines 17-23, kindly replace the equation " $S_j = \sqrt{\frac{1}{m-1}\sum_{i=1}^{m}(X_{i,j}^o - X_j^\mu)^2}$ " with -- $s_j = \sqrt{\frac{1}{m-1}\sum_{i=1}^{m}(x_{i,j}^o - x_j^\mu)^2}$ --.

At column 17, line 25, kindly replace the equation " $D_k^2 = s_k M_k^{-1} S_k^T$ " with -- $D_k^2 = s_k M_k^{-1} s_k^T$ --; at line 32, kindly replace the term "(MD/PCA/IR)" with --(MD/PCA/R)--.

At column 22, line 66, kindly replace the equation " $ec_i^o = c^{iO} - \hat{c}_i^o$ " with -- $ec_i^o = c_i^o - \hat{c}_i^o$ --.

At column 29, line 60, kindly replace the equation " $\overline{c}2,u = \hat{\beta s}_{2,u}^f$ " with -- $\overline{c}_{2,u} = \hat{\beta s}_{2,u}^f$ --.

Signed and Sealed this

Fifteenth Day of April, 2008

JON W. DUDAS
*Director of the United States Patent and Trademark Office*